(12) United States Patent
Zhan et al.

(10) Patent No.: US 11,667,686 B2
(45) Date of Patent: Jun. 6, 2023

(54) ERYTHROPOIETIN AND ANALOGS FOR VETERINARY USE

(71) Applicant: Kindred Biosciences, Inc., Burlingame, CA (US)

(72) Inventors: Hangjun Zhan, Foster City, CA (US); Lam Nguyen, Union City, CA (US); Yongzhong Li, Burlingame, CA (US); Qingyi Chu, Burlingame, CA (US); Estela Garcia-Murillo, Burlingame, CA (US); Victoria Leitman, Burlingame, CA (US); Stephen Sundlof, Burlingame, CA (US); Richard Chin, San Francisco, CA (US); Shyr Jiann Li, Millbrae, CA (US)

(73) Assignee: Kindred Biosciences, Inc., Burlingame, CA (US)

(*) Notice: Subject to any disclaimer, the term of this patent is extended or adjusted under 35 U.S.C. 154(b) by 287 days.

(21) Appl. No.: 16/617,380

(22) PCT Filed: Jun. 5, 2018

(86) PCT No.: PCT/US2018/036133
§ 371 (c)(1),
(2) Date: Nov. 26, 2019

(87) PCT Pub. No.: WO2018/226747
PCT Pub. Date: Dec. 13, 2018

(65) Prior Publication Data
US 2021/0032305 A1 Feb. 4, 2021

Related U.S. Application Data

(60) Provisional application No. 62/559,104, filed on Sep. 15, 2017, provisional application No. 62/516,642, filed on Jun. 7, 2017, provisional application No. 62/516,092, filed on Jun. 6, 2017.

(51) Int. Cl.
| | | |
|---|---|---|
| *C07K 14/505* | (2006.01) | |
| *A61K 47/60* | (2017.01) | |
| *A61K 47/26* | (2006.01) | |
| *A61P 7/06* | (2006.01) | |
| *A61K 38/00* | (2006.01) | |

(52) U.S. Cl.
CPC ............ *C07K 14/505* (2013.01); *A61K 47/26* (2013.01); *A61K 47/60* (2017.08); *A61P 7/06* (2018.01); *A61K 38/00* (2013.01)

(58) Field of Classification Search
CPC ...... C07K 14/505; A61K 47/60; A61K 47/26; A61K 38/00; A61P 7/06
See application file for complete search history.

(56) References Cited

U.S. PATENT DOCUMENTS

| | | |
|---|---|---|
| 5,856,298 A | 1/1999 | Strickland |
| 9,624,485 B2 | 4/2017 | Liu et al. |
| 10,287,336 B2 | 5/2019 | Lu et al. |
| 2004/0248797 A1 | 12/2004 | Cheung et al. |
| 2010/0297117 A1* | 11/2010 | Sloey ............... A61K 39/3955 424/130.1 |
| 2016/0024166 A1 | 1/2016 | Tian et al. |
| 2016/0083444 A1 | 3/2016 | Lu et al. |

FOREIGN PATENT DOCUMENTS

| | | |
|---|---|---|
| EP | 0640619 B1 | 7/1997 |
| WO | 2006081430 A2 | 8/2006 |
| WO | 2010036964 A2 | 4/2010 |
| WO | 2016044676 A2 | 3/2016 |
| WO | 2019209716 A9 | 10/2019 |

OTHER PUBLICATIONS

Bork et al., "Enhanced sialylation of EPO by overexpression of UDP-GlcNAc 2-epimerase/ManAc kinase continuing a sialuria mutation in CHO cells," FEBS Letters, 2007, vol. 581, pp. 4195-4198, 4 pages.
Breitling et al., "N-Linked Protein Glycosylation in the Endoplasmic Reticulum," Cold Spring Harb Perspect Biol, 2013, 5(8):a013359, pp. 1-15.
English translation of Office Action received in Russian Application No. 2019143664, dated Feb. 14, 2022, 7 pages.
International Search Report and Written Opinion for PCT/US2019/066052, dated Apr. 28, 2020, 15 pages.
Jonsson et al., "Introducing a biosensor based technology for real-time biospecific interaction analysis," Ann. Biol. Clin., 1993, 51(1):19-26, Abstract.
Kitamura et al., "Identification and Analysis of Human Erythropoietin Receptors on a Factor-Dependent Cell Line, TF-1," Blood, 1989, vol. 73, No. 2, pp. 375-380.
Markely "High-Throughput Quantification of Glycoprotein Sialylation," 2011, Submitted to the Department of Chemical Engineering on Apr. 18, 2011 In Partial Fulfillment of the Requirements for the Degree of Doctor of Philosophy in Chemical Engineering, 105 pages.

(Continued)

*Primary Examiner* — Li N Komatsu
(74) *Attorney, Agent, or Firm* — Barnes & Thornburg LLP

(57) ABSTRACT

Provided are various embodiments relating to feline erythropoietin (EPO) polypeptide analogs with one or more additional glycosylation sites and methods of producing and using the same to treat anemia in companion animals. Also provided are various embodiments relating to EPO polypeptides having a mutation in the second binding site, polypeptides comprising an extracellular domain of EPO receptor, and methods of using the same for treating polycythemia in mammals.

10 Claims, 17 Drawing Sheets
Specification includes a Sequence Listing.

(56) References Cited

OTHER PUBLICATIONS

Millipore Sigma, "TF1 Cell Line human Erythroleukemic cell line from blood., 93022307," Sigma-Aldrich, Product Description, 2022, 7 pages.

Philo et al., "Dimerization of the extracellular domain of the erythropoietin (EPO) receptor by EPO: one high-affinity and one low-affinity interaction," Biochemistry. 1996, 35(5):1681-91.

Randolph et al., "Expression, bioactivity, and clinical assessment of recombinant feline erythropoietin," AJVR, 2004, vol. 65, No. 10, pp. 1355-1366.

Abdiche, et al., "Determining kinetics and affinities of protein interactions using a parallel real-time label-free biosensor, the Octet," Anal Biochem. 377(2):209-17 (2008).

Caval et al., "Direct quality control of glycoengineered erythropoietin variants," Nat Commun. 9(1):3342 (2018), 8 pages.

Egrie et al., "Development and characterization of novel erythropoiesis stimulating protein (NESP)," Br J Cancer. 84 (Suppl. 1):3-10 (2001).

Elliott et al., "Structural Requirements for Additional N-Linked Carbohydrate on Recombinant Human Erythropoietin," J Biol Chem. 279(16):16854-16862 (2004).

International Search Report and Written Opinion for PCT/US2018/036133, dated Oct. 18, 2018 (14 pages).

Li et al., "0.9% saline is neither normal nor physiological", J Zhejiang Univ-Sci B (Biomed & Biotechnol), 17(3):181-187, 2016.

Locatelli et al., "Optimizing the management of renal anemia: challenges and new opportunities," Kidney Intl. 74 (Suppl 111):S33-S37 (2008).

Mauldin, et al., "Exfoliative cutaneous lupus erythematosus in German shorthaired pointer dogs: disease development, progression and evaluation of three immunomodulatory drugs (ciclosporin, hydroxychloroquine, and adalimumab) in a controlled environment," Vet Dermatol. 21(4):373-382 (2010), author manuscript version, 18 pages.

Savinova, et al., "The efficiency of fatty acids, N-acetyl-D-mannosamine, and N-acetylneuraminic acid for a change in the sialylation profile of recombinant darbepoetin alfa in CHO cell culture," Applied Biochem & Microbiol. 51(8):827-833 (2015).

Zhan et al., "Engineering a soluble extracellular erythropoietin receptor (EPObp) in Pichia pastoris to eliminate microheterogeneity, and its complex with erythropoietin," Protein Engineering. 12(6):505-513 (1999).

Extended European Search Report received in European Application No. 18813400.1, dated Jan. 22, 2021, 7 pages.

\* cited by examiner

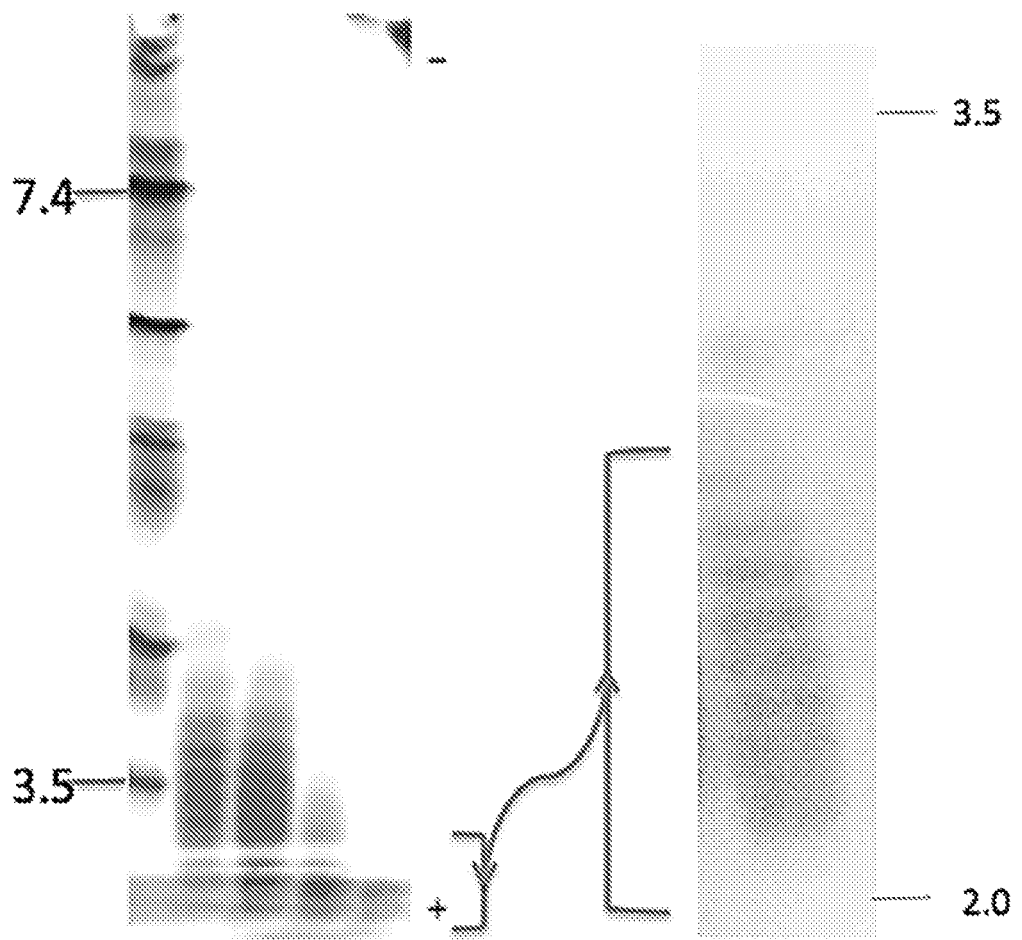
*Fig. 2A*  *Fig. 2B*

| Parameter (IM) | Avg n=3 |
|---|---|
| AUC (0-168) (ng*hr/mL) | 602 |
| Cmax (ng) | 14.2 |
| Tmax (hr) | 8 |
| t ½ (hr) | 24 |
| Bioavailability (%) | 51 |

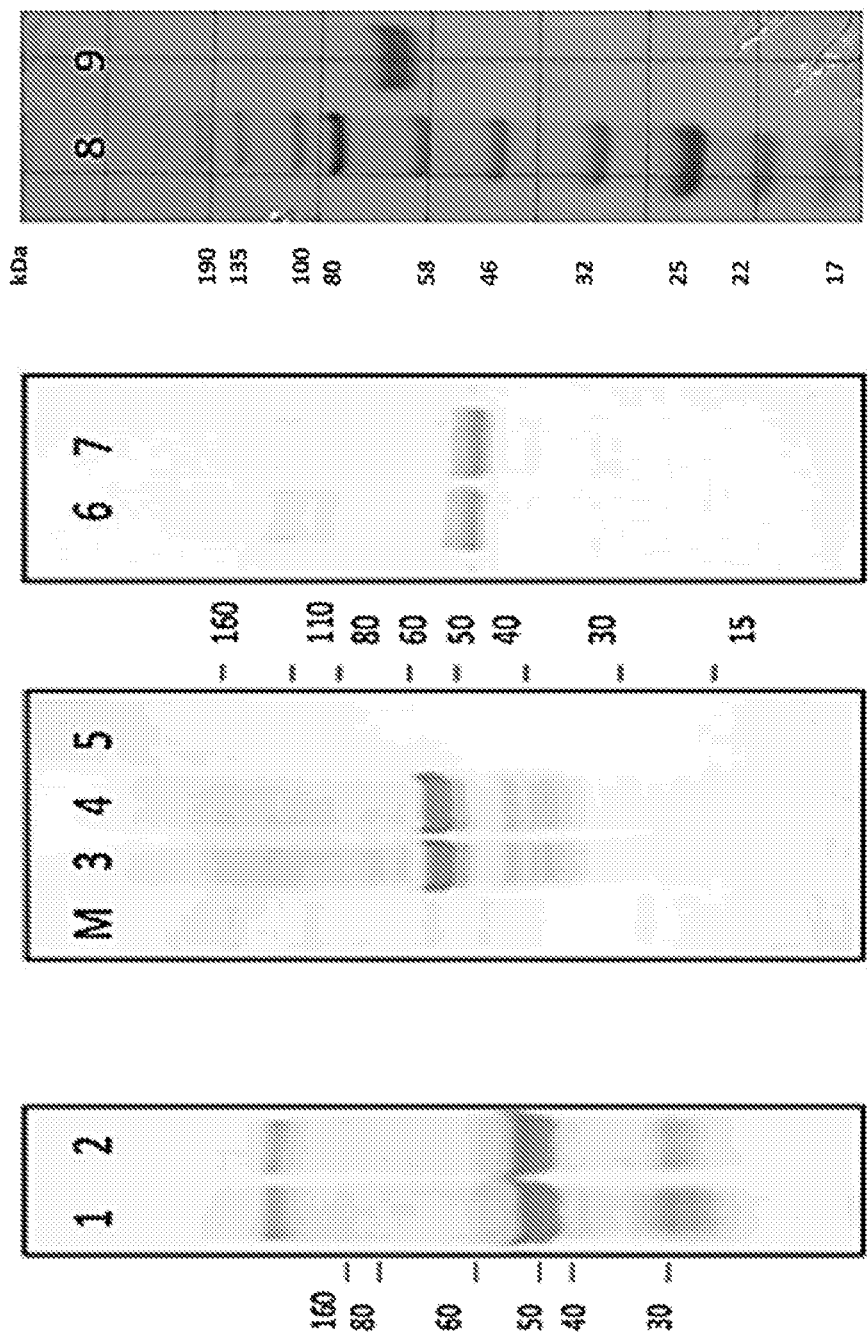

SEQUENCE LISTING

<160> NUMBER OF SEQ ID NOS: 32

<210> SEQ ID NO 1
<211> LENGTH: 192
<212> TYPE: PRT
<213> ORGANISM: Felis catus

<400> SEQUENCE: 1

Met Gly Ser Cys Glu Cys Pro Ala Leu Leu Leu Leu Leu Ser Leu Leu
1               5                   10                  15

Leu Leu Pro Leu Gly Leu Pro Val Leu Gly Ala Pro Pro Arg Leu Ile
            20                  25                  30

Cys Asp Ser Arg Val Leu Glu Arg Tyr Ile Leu Gly Ala Arg Glu Ala
        35                  40                  45

Glu Asn Val Thr Met Gly Cys Ala Glu Gly Cys Ser Phe Ser Glu Asn
    50                  55                  60

Ile Thr Val Pro Asp Thr Lys Val Asn Phe Tyr Thr Trp Lys Arg Met

```
            65                  70                  75                  80
Asp Val Gly Gln Gln Ala Val Glu Val Trp Gln Gly Leu Ala Leu Leu
                    85                  90                  95

Ser Glu Ala Ile Leu Arg Gly Gln Ala Leu Leu Ala Asn Ser Ser Gln
                100                 105                 110

Pro Ser Glu Thr Leu Gln Leu His Val Asp Lys Ala Val Ser Ser Leu
                115                 120                 125

Arg Ser Leu Thr Ser Leu Leu Arg Ala Leu Gly Ala Gln Lys Glu Ala
            130                 135                 140

Thr Ser Leu Pro Glu Ala Thr Ser Ala Ala Pro Leu Arg Thr Phe Thr
145                 150                 155                 160

Val Asp Thr Leu Cys Lys Leu Phe Arg Ile Tyr Ser Asn Phe Leu Arg
                    165                 170                 175

Gly Lys Leu Thr Leu Tyr Thr Gly Glu Ala Cys Arg Arg Gly Asp Arg
                180                 185                 190
```

<210> SEQ ID NO 2
<211> LENGTH: 192
<212> TYPE: PRT
<213> ORGANISM: Felis catus

<400> SEQUENCE: 2

```
Met Gly Ser Cys Glu Cys Pro Ala Leu Leu Leu Leu Leu Ser Leu Leu
1               5                   10                  15

Leu Leu Pro Leu Gly Leu Pro Val Leu Gly Ala Pro Pro Arg Leu Ile
                20                  25                  30

Cys Asp Ser Arg Val Leu Glu Arg Tyr Ile Leu Glu Ala Arg Glu Ala
            35                  40                  45

Glu Asn Val Thr Met Gly Cys Ala Glu Gly Cys Ser Phe Ser Glu Asn
        50                  55                  60

Ile Thr Val Pro Asp Thr Lys Val Asn Phe Tyr Thr Trp Lys Arg Met
65                  70                  75                  80

Asp Val Gly Gln Gln Ala Val Glu Val Trp Gln Gly Leu Ala Leu Leu
                    85                  90                  95

Ser Glu Ala Ile Leu Arg Gly Gln Ala Leu Leu Ala Asn Ser Ser Gln
                100                 105                 110

Pro Ser Glu Thr Leu Gln Leu His Val Asp Lys Ala Val Ser Ser Leu
                115                 120                 125

Arg Ser Leu Thr Ser Leu Leu Arg Ala Leu Gly Ala Gln Lys Glu Ala
            130                 135                 140

Thr Ser Leu Pro Glu Ala Thr Ser Ala Ala Pro Leu Arg Thr Phe Thr
145                 150                 155                 160

Val Asp Thr Leu Cys Lys Leu Phe Arg Ile Tyr Ser Asn Phe Leu Arg
                    165                 170                 175

Gly Lys Leu Thr Leu Tyr Thr Gly Glu Ala Cys Arg Arg Gly Asp Arg
                180                 185                 190
```

<210> SEQ ID NO 3
<211> LENGTH: 192
<212> TYPE: PRT
<213> ORGANISM: Artificial Sequence
<220> FEATURE:
<223> OTHER INFORMATION: Feline EPO Analog 6-30 G44V113 precursor form
      or "Analog 6-30 GV Prec

```
            1               5                   10                  15
Leu Leu Pro Leu Gly Leu Pro Val Leu Gly Ala Pro Pro Arg Leu Ile
            20                  25                  30

Cys Asp Ser Arg Val Leu Glu Arg Tyr Ile Leu Gly Ala Arg Glu Ala
            35                  40                  45

Glu Asn Val Thr Met Gly Cys Asn Glu Thr Cys Ser Phe Ser Glu Asn
            50                  55                  60

Ile Thr Val Pro Asp Thr Lys Val Asn Phe Tyr Thr Trp Lys Arg Met
65                  70                  75                  80

Asp Val Gly Gln Gln Ala Val Glu Val Trp Gln Gly Leu Ala Leu Leu
                85                  90                  95

Ser Glu Ala Ile Leu Arg Gly Gln Ala Leu Leu Ala Asn Ser Ser Gln
                100                 105                 110

Val Asn Glu Thr Leu Gln Leu His Val Asp Lys Ala Val Ser Ser Leu
                115                 120                 125

Arg Ser Leu Thr Ser Leu Leu Arg Ala Leu Gly Ala Gln Lys Glu Ala
        130                 135                 140

Thr Ser Leu Pro Glu Ala Thr Ser Ala Ala Pro Leu Arg Thr Phe Thr
145                 150                 155                 160

Val Asp Thr Leu Cys Lys Leu Phe Arg Ile Tyr Ser Asn Phe Leu Arg
                165                 170                 175

Gly Lys Leu Thr Leu Tyr Thr Gly Glu Ala Cys Arg Arg Gly Asp Arg
                180                 185                 190

<210> SEQ ID NO 4
<211> LENGTH: 192
<212> TYPE: PRT
<213> ORGANISM: Artificial Sequence
<220> FEATURE:
<223> OTHER INFORMATION: Feline EPO Analog 6-30 E44V113 precursor form
      or "Analog 6-30 EV Precursor"

<400> SEQUENCE: 4

Met Gly Ser Cys Glu Cys Pro Ala Leu Leu Leu Leu Ser Leu Leu
1               5                   10                  15

Leu Leu Pro Leu Gly Leu Pro Val Leu Gly Ala Pro Pro Arg Leu Ile
            20                  25                  30

Cys Asp Ser Arg Val Leu Glu Arg Tyr Ile Leu Glu Ala Arg Glu Ala
            35                  40                  45

Glu Asn Val Thr Met Gly Cys Asn Glu Thr Cys Ser Phe Ser Glu Asn
            50                  55                  60

Ile Thr Val Pro Asp Thr Lys Val Asn Phe Tyr Thr Trp Lys Arg Met
65                  70                  75                  80

Asp Val Gly Gln Gln Ala Val Glu Val Trp Gln Gly Leu Ala Leu Leu
                85                  90                  95

Ser Glu Ala Ile Leu Arg Gly Gln Ala Leu Leu Ala Asn Ser Ser Gln
                100                 105                 110

Val Asn Glu Thr Leu Gln Leu His Val Asp Lys Ala Val Ser Ser Leu
                115                 120                 125

Arg Ser Leu Thr Ser Leu Leu Arg Ala Leu Gly Ala Gln Lys Glu Ala
        130                 135                 140

Thr Ser Leu Pro Glu Ala Thr Ser Ala Ala Pro Leu Arg Thr Phe Thr
145                 150                 155                 160

Val Asp Thr Leu Cys Lys Leu Phe Arg Ile Tyr Ser Asn Phe Leu Arg
                165                 170                 175
```

```
Gly Lys Leu Thr Leu Tyr Thr Gly Glu Ala Cys Arg Arg Gly Asp Arg
            180                 185                 190

<210> SEQ ID NO 5
<211> LENGTH: 522
<212> TYPE: PRT
<213> ORGANISM: Artificial Sequence
<220> FEATURE:
<223> OTHER INFORMATION: Flag_feline EPOR201_full-length
      (fEPOR201-N-flag)

<400> SEQUENCE: 5

Met Asp His Leu Trp Ala Pro Leu Trp Pro Gly Val Gly Ser Leu Cys
1               5                   10                  15

Leu Leu Leu Ala Gly Ala Ala Trp Ala Met Asp Tyr Lys Asp Asp Asp
            20                  25                  30

Asp Lys Ala Pro Pro Pro Asn Pro Leu Asp Pro Lys Phe Glu Ser Lys
            35                  40                  45

Val Asn Met Val Cys Met Arg Ala Pro Glu Ala Ser Ala Cys Gly Ser
50                  55                  60

Ser Glu Arg Leu Glu Asp Leu Val Cys Phe Trp Glu Glu Ala Ala Ser
65                  70                  75                  80

Ala Gly Val Gly Pro Asp Asn Tyr Ser Phe Phe Tyr Gln Leu Glu Gly
            85                  90                  95

Glu Pro Trp Lys Pro Cys Ser Leu His Gln Ala Pro Thr Ala Arg Gly
            100                 105                 110

Ala Val Arg Phe Trp Cys Ser Leu Pro Thr Ala Asp Ala Ser Ser Phe
            115                 120                 125

Val Pro Leu Glu Leu Arg Val Thr Ala Val Ser Ser Gly Ala Pro Arg
130                 135                 140

Tyr His Arg Ile Ile His Ile Asn Glu Val Val Leu Leu Asp Pro Pro
145                 150                 155                 160

Ala Gly Leu Leu Ala Arg Arg Ala Asp Glu Gly Gly His Val Val Leu
            165                 170                 175

Arg Trp Leu Pro Pro Pro Gly Ala Pro Val Ala Ser Leu Ile Arg Tyr
            180                 185                 190

Glu Val Asn Ile Ser Ser Gly Asn Val Ala Gly Gly Ala Gln Lys Val
            195                 200                 205

Glu Ile Leu Asp Gly Arg Thr Glu Cys Ala Leu Ser Asn Leu Arg Gly
            210                 215                 220

Arg Thr Arg Tyr Thr Phe Met Val Arg Ala Arg Met Ala Glu Pro Ser
225                 230                 235                 240

Phe Gly Gly Phe Trp Ser Ala Trp Ser Glu Pro Ala Ser Leu Leu Thr
            245                 250                 255

Ala Ser Asp Leu Asp Pro Leu Ile Leu Thr Leu Ser Leu Ile Leu Val
            260                 265                 270

Leu Ile Leu Leu Leu Leu Ala Val Leu Ala Leu Leu Ser His Arg Arg
            275                 280                 285

Phe Thr Arg Thr Leu Lys Gln Lys Ile Trp Pro Gly Ile Pro Ser Pro
            290                 295                 300

Glu Ser Glu Phe Glu Gly Leu Phe Thr Thr His Lys Gly Asn Phe Gln
305                 310                 315                 320

Leu Trp Leu Tyr Gln Asn Glu Gly Cys Leu Trp Trp Ser Pro Cys Ala
            325                 330                 335

Pro Phe Ala Glu Asp Pro Pro Ser Pro Leu Glu Val Leu Ser Glu Arg
            340                 345                 350
```

```
Cys Trp Gly Ala Thr Gln Ala Ala Glu Pro Gly Ala Glu Glu Gly Pro
            355                 360                 365

Leu Leu Glu Pro Leu Gly Ser Glu His Thr Gln Asp Thr Tyr Leu Val
    370                 375                 380

Leu Asp Lys Trp Leu Leu Pro Arg Asn Pro Pro Ser Glu Asp Leu Pro
385                 390                 395                 400

Arg Pro Asp Gly Ser Leu Asp Met Val Ala Met His Lys Gly Ser Glu
                405                 410                 415

Ala Ser Ser Cys Ser Ser Ala Leu Ser Leu Lys Pro Gly Pro Glu Gly
            420                 425                 430

Ala Leu Gly Ala Ser Phe Glu Tyr Thr Ile Leu Asp Pro Ser Ser Gln
            435                 440                 445

Leu Leu Arg Pro Arg Ala Leu Pro Pro Glu Leu Pro Pro Thr Pro Pro
    450                 455                 460

His Ile Lys Tyr Leu Tyr Leu Met Val Ser Asp Ser Gly Ile Ser Thr
465                 470                 475                 480

Asp Tyr Ser Ser Gly Gly Ser Gln Glu Ala Gln Gly Asp Ser Ser Thr
                485                 490                 495

Gly Pro Tyr Leu Asn Pro Tyr Glu Asn Ser Leu Ile Pro Ala Thr Glu
            500                 505                 510

Thr Ser Pro Pro Ser Tyr Val Ala Cys Ser
            515                 520

<210> SEQ ID NO 6
<211> LENGTH: 521
<212> TYPE: PRT
<213> ORGANISM: Artificial Sequence
<220> FEATURE:
<223> OTHER INFORMATION: Flag_feline EPOR202_full-length
      (fEPOR202-N-flag)

<400> SEQUENCE: 6

Met Asp His Leu Trp Ala Pro Leu Trp Pro Gly Val Gly Ser Leu Cys
1               5                   10                  15

Leu Leu Leu Ala Gly Ala Ala Trp Ala Met Asp Tyr Lys Asp Asp Asp
            20                  25                  30

Asp Lys Ala Pro Pro Pro Asn Pro Leu Asp Pro Lys Phe Glu Ser Lys
        35                  40                  45

Gly Lys Asp Gly Ser Val Cys Arg Pro Pro Gln Trp Phe Leu Glu Gly
    50                  55                  60

Asn Ala Glu Glu Arg Leu Glu Asp Leu Val Cys Phe Trp Glu Glu Ala
65                  70                  75                  80

Ala Ser Ala Gly Val Gly Pro Asp Asn Tyr Ser Phe Phe Tyr Gln Leu
                85                  90                  95

Glu Gly Glu Pro Trp Lys Pro Cys Ser Leu His Gln Ala Pro Thr Ala
            100                 105                 110

Arg Gly Ala Val Arg Phe Trp Cys Ser Leu Pro Thr Ala Asp Ala Ser
        115                 120                 125

Ser Phe Val Pro Leu Glu Leu Arg Val Thr Ala Val Ser Ser Gly Ala
    130                 135                 140

Pro Arg Tyr His Arg Ile Ile His Ile Asn Glu Val Val Leu Leu Asp
145                 150                 155                 160

Pro Pro Ala Gly Leu Leu Ala Arg Arg Ala Asp Glu Gly Gly His Val
                165                 170                 175

Val Leu Arg Trp Leu Pro Pro Pro Gly Ala Pro Val Ala Ser Leu Ile
```

```
                180             185             190
Arg Tyr Glu Val Asn Ile Ser Ser Gly Asn Val Ala Gly Gly Ala Gln
            195             200             205

Lys Val Glu Ile Leu Asp Gly Arg Thr Glu Cys Ala Leu Ser Asn Leu
        210             215             220

Arg Gly Arg Thr Arg Tyr Thr Phe Met Val Arg Ala Arg Met Ala Glu
225             230             235             240

Pro Ser Phe Gly Gly Phe Trp Ser Ala Trp Ser Glu Pro Ala Ser Leu
            245             250             255

Leu Thr Ala Ser Asp Leu Asp Pro Leu Ile Leu Thr Leu Ser Leu Ile
        260             265             270

Leu Val Leu Ile Leu Leu Leu Ala Val Leu Ala Leu Leu Ser His
        275             280             285

Arg Arg Thr Leu Lys Gln Lys Ile Trp Pro Gly Ile Pro Ser Pro Glu
        290             295             300

Ser Glu Phe Glu Gly Leu Phe Thr Thr His Lys Gly Asn Phe Gln Leu
305             310             315             320

Trp Leu Tyr Gln Asn Glu Gly Cys Leu Trp Trp Ser Pro Cys Ala Pro
            325             330             335

Phe Ala Glu Asp Pro Pro Ser Pro Leu Glu Val Leu Ser Glu Arg Cys
            340             345             350

Trp Gly Ala Thr Gln Ala Ala Glu Pro Gly Ala Glu Glu Gly Pro Leu
            355             360             365

Leu Glu Pro Leu Gly Ser Glu His Thr Gln Asp Thr Tyr Leu Val Leu
        370             375             380

Asp Lys Trp Leu Leu Pro Arg Asn Pro Pro Ser Glu Asp Leu Pro Arg
385             390             395             400

Pro Asp Gly Ser Leu Asp Met Val Ala Met His Lys Gly Ser Glu Ala
            405             410             415

Ser Ser Cys Ser Ser Ala Leu Ser Leu Lys Pro Gly Pro Glu Gly Ala
            420             425             430

Leu Gly Ala Ser Phe Glu Tyr Thr Ile Leu Asp Pro Ser Ser Gln Leu
        435             440             445

Leu Arg Pro Arg Ala Leu Pro Pro Glu Leu Pro Pro Thr Pro Pro His
        450             455             460

Ile Lys Tyr Leu Tyr Leu Met Val Ser Asp Ser Gly Ile Ser Thr Asp
465             470             475             480

Tyr Ser Ser Gly Gly Ser Gln Glu Ala Gln Gly Asp Ser Ser Thr Gly
            485             490             495

Pro Tyr Leu Asn Pro Tyr Glu Asn Ser Leu Ile Pro Ala Thr Glu Thr
            500             505             510

Ser Pro Pro Ser Tyr Val Ala Cys Ser
            515             520

<210> SEQ ID NO 7
<211> LENGTH: 488
<212> TYPE: PRT
<213> ORGANISM: Artificial Sequence
<220> FEATURE:
<223> OTHER INFORMATION: Feline EPOR201_ECD_human Fc

<400> SEQUENCE: 7

Met Asp His Leu Trp Ala Pro Leu Trp Pro Gly Val Gly Ser Leu Cys
1               5               10              15

Leu Leu Leu Ala Gly Ala Ala Trp Ala Pro Pro Pro Asn Pro Leu Asp
```

-continued

```
            20                  25                  30
Pro Lys Phe Glu Ser Lys Val Asn Met Val Cys Met Arg Ala Pro Glu
        35                  40                  45

Ala Ser Ala Cys Gly Ser Ser Glu Arg Leu Glu Asp Leu Val Cys Phe
 50                  55                  60

Trp Glu Glu Ala Ala Ser Ala Gly Val Gly Pro Asp Asn Tyr Ser Phe
 65                  70                  75                  80

Phe Tyr Gln Leu Glu Gly Glu Pro Trp Lys Pro Cys Ser Leu His Gln
                85                  90                  95

Ala Pro Thr Ala Arg Gly Ala Val Arg Phe Trp Cys Ser Leu Pro Thr
            100                 105                 110

Ala Asp Ala Ser Ser Phe Val Pro Leu Glu Leu Arg Val Thr Ala Val
        115                 120                 125

Ser Ser Gly Ala Pro Arg Tyr His Arg Ile Ile His Ile Asn Glu Val
 130                 135                 140

Val Leu Leu Asp Pro Pro Ala Gly Leu Leu Ala Arg Arg Ala Asp Glu
145                 150                 155                 160

Gly Gly His Val Val Leu Arg Trp Leu Pro Pro Pro Gly Ala Pro Val
                165                 170                 175

Ala Ser Leu Ile Arg Tyr Glu Val Asn Ile Ser Ser Gly Asn Val Ala
            180                 185                 190

Gly Gly Ala Gln Lys Val Glu Ile Leu Asp Gly Arg Thr Glu Cys Ala
        195                 200                 205

Leu Ser Asn Leu Arg Gly Arg Thr Arg Tyr Thr Phe Met Val Arg Ala
 210                 215                 220

Arg Met Ala Glu Pro Ser Phe Gly Gly Phe Trp Ser Ala Trp Ser Glu
225                 230                 235                 240

Pro Ala Ser Leu Leu Thr Ala Ser Asp Leu Asp Ile Glu Gly Arg Met
                245                 250                 255

Asp Pro Lys Ser Cys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
 290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
 370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445
```

```
Ser Lys Leu Thr Val Asp Lys Ser Arg Trp Gln Gln Gly Asn Val Phe
    450                 455                 460
Ser Cys Ser Val Met His Glu Ala Leu His Asn His Tyr Thr Gln Lys
465                 470                 475                 480
Ser Leu Ser Leu Ser Pro Gly Lys
                485

<210> SEQ ID NO 8
<211> LENGTH: 490
<212> TYPE: PRT
<213> ORGANISM: Artificial Sequence
<220> FEATURE:
<223> OTHER INFORMATION: Feline EPOR202_ECD_human Fc

<400> SEQUENCE: 8

Met Asp His Leu Trp Ala Pro Leu Trp Pro Gly Val Gly Ser Leu Cys
1               5                   10                  15
Leu Leu Leu Ala Gly Ala Ala Trp Ala Pro Pro Asn Pro Leu Asp
            20                  25                  30
Pro Lys Phe Glu Ser Lys Gly Lys Asp Gly Ser Val Cys Arg Pro Pro
        35                  40                  45
Gln Trp Phe Leu Glu Gly Asn Ala Glu Glu Arg Leu Glu Asp Leu Val
    50                  55                  60
Cys Phe Trp Glu Ala Ala Ser Ala Gly Val Gly Pro Asp Asn Tyr
65                  70                  75                  80
Ser Phe Phe Tyr Gln Leu Glu Gly Glu Pro Trp Lys Pro Cys Ser Leu
                85                  90                  95
His Gln Ala Pro Thr Ala Arg Gly Ala Val Arg Phe Trp Cys Ser Leu
            100                 105                 110
Pro Thr Ala Asp Ala Ser Ser Phe Val Pro Leu Glu Leu Arg Val Thr
        115                 120                 125
Ala Val Ser Ser Gly Ala Pro Arg Tyr His Arg Ile Ile His Ile Asn
    130                 135                 140
Glu Val Val Leu Leu Asp Pro Pro Ala Gly Leu Leu Ala Arg Arg Ala
145                 150                 155                 160
Asp Glu Gly Gly His Val Val Leu Arg Trp Leu Pro Pro Pro Gly Ala
                165                 170                 175
Pro Val Ala Ser Leu Ile Arg Tyr Glu Val Asn Ile Ser Ser Gly Asn
            180                 185                 190
Val Ala Gly Gly Ala Gln Lys Val Glu Ile Leu Asp Gly Arg Thr Glu
        195                 200                 205
Cys Ala Leu Ser Asn Leu Arg Gly Arg Thr Arg Tyr Thr Phe Met Val
    210                 215                 220
Arg Ala Arg Met Ala Glu Pro Ser Phe Gly Gly Phe Trp Ser Ala Trp
225                 230                 235                 240
Ser Glu Pro Ala Ser Leu Leu Thr Ala Ser Asp Leu Asp Ile Glu Gly
                245                 250                 255
Arg Met Asp Pro Lys Ser Cys Asp Lys Thr His Thr Cys Pro Pro Cys
            260                 265                 270
Pro Ala Pro Glu Leu Leu Gly Gly Pro Ser Val Phe Leu Phe Pro Pro
        275                 280                 285
Lys Pro Lys Asp Thr Leu Met Ile Ser Arg Thr Pro Glu Val Thr Cys
    290                 295                 300
Val Val Val Asp Val Ser His Glu Asp Pro Glu Val Lys Phe Asn Trp
305                 310                 315                 320
```

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Asp Glu
385                 390                 395                 400

Leu Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Met His Glu Ala Leu His Asn His Tyr Thr
465                 470                 475                 480

Gln Lys Ser Leu Ser Leu Ser Pro Gly Lys
                485                 490

<210> SEQ ID NO 9
<211> LENGTH: 166
<212> TYPE: PRT
<213> ORGANISM: Homo sapiens

<400> SEQUENCE: 9

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 10
<211> LENGTH: 166
<212> TYPE: PRT

<213> ORGANISM: Canis lupus

<400> SEQUENCE: 10

Ala Pro Pro Arg Leu Ile Cys Asp Ser Arg Val Leu Glu Arg Tyr Ile
1               5                   10                  15

Leu Glu Ala Arg Glu Ala Glu Asn Val Thr Met Gly Cys Ala Gln Gly
            20                  25                  30

Cys Ser Phe Ser Glu Asn Ile Thr Val Pro Asp Thr Lys Val Asn Phe
        35                  40                  45

Tyr Thr Trp Lys Arg Met Asp Val Gly Gln Gln Ala Leu Glu Val Trp
50                  55                  60

Gln Gly Leu Ala Leu Leu Ser Glu Ala Ile Leu Arg Gly Gln Ala Leu
65                  70                  75                  80

Leu Ala Asn Ala Ser Gln Pro Ser Glu Thr Pro Gln Leu His Val Asp
                85                  90                  95

Lys Ala Val Ser Ser Leu Arg Ser Leu Thr Ser Leu Leu Arg Ala Leu
            100                 105                 110

Gly Ala Gln Lys Glu Ala Met Ser Leu Pro Glu Glu Ala Ser Pro Ala
        115                 120                 125

Pro Leu Arg Thr Phe Thr Val Asp Thr Leu Cys Lys Leu Phe Arg Ile
130                 135                 140

Tyr Ser Asn Phe Leu Arg Gly Lys Leu Thr Leu Tyr Thr Gly Glu Ala
145                 150                 155                 160

Cys Arg Arg Gly Asp Arg
                165

<210> SEQ ID NO 11
<211> LENGTH: 166
<212> TYPE: PRT
<213> ORGANISM: Equus caballus

<400> SEQUENCE: 11

Ala Pro Pro Arg Leu Ile Cys Asp Ser Arg Val Leu Glu Arg Tyr Ile
1               5                   10                  15

Leu Glu Ala Arg Glu Ala Glu Asn Val Thr Met Gly Cys Ala Glu Gly
            20                  25                  30

Cys Ser Phe Gly Glu Asn Val Thr Val Pro Asp Thr Lys Val Asn Phe
        35                  40                  45

Tyr Ser Trp Lys Arg Met Glu Val Gly Gln Gln Ala Val Glu Val Trp
50                  55                  60

Gln Gly Leu Ala Leu Leu Ser Glu Ala Ile Leu Gln Gly Gln Ala Leu
65                  70                  75                  80

Leu Ala Asn Ser Ser Gln Pro Ser Glu Thr Leu Arg Leu His Val Asp
                85                  90                  95

Lys Ala Val Ser Ser Leu Arg Ser Leu Thr Ser Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Phe Ala Val Asp Thr Leu Cys Lys Leu Phe Arg Ile
130                 135                 140

Tyr Ser Asn Phe Leu Arg Gly Lys Leu Lys Leu Tyr Thr Gly Glu Ala
145                 150                 155                 160

Cys Arg Arg Gly Asp Arg
                165

```
<210> SEQ ID NO 12
<211> LENGTH: 166
<212> TYPE: PRT
<213> ORGANISM: Felis catus

<400> SEQUENCE: 12

Ala Pro Pro Arg Leu Ile Cys Asp Ser Arg Val Leu Glu Arg Tyr Ile
1               5                   10                  15

Leu Gly Ala Arg Glu Ala Glu Asn Val Thr Met Gly Cys Ala Glu Gly
            20                  25                  30

Cys Ser Phe Ser Glu Asn Ile Thr Val Pro Asp Thr Lys Val Asn Phe
        35                  40                  45

Tyr Thr Trp Lys Arg Met Asp Val Gly Gln Gln Ala Val Glu Val Trp
    50                  55                  60

Gln Gly Leu Ala Leu Leu Ser Glu Ala Ile Leu Arg Gly Gln Ala Leu
65                  70                  75                  80

Leu Ala Asn Ser Ser Gln Pro Ser Glu Thr Leu Gln Leu His Val Asp
                85                  90                  95

Lys Ala Val Ser Ser Leu Arg Ser Leu Thr Ser Leu Leu Arg Ala Leu
            100                 105                 110

Gly Ala Gln Lys Glu Ala Thr Ser Leu Pro Glu Ala Thr Ser Ala Ala
        115                 120                 125

Pro Leu Arg Thr Phe Thr Val Asp Thr Leu Cys Lys Leu Phe Arg Ile
    130                 135                 140

Tyr Ser Asn Phe Leu Arg Gly Lys Leu Thr Leu Tyr Thr Gly Glu Ala
145                 150                 155                 160

Cys Arg Arg Gly Asp Arg
                165

<210> SEQ ID NO 13
<211> LENGTH: 166
<212> TYPE: PRT
<213> ORGANISM: Felis catus

<400> SEQUENCE: 13

Ala Pro Pro Arg Leu Ile Cys Asp Ser Arg Val Leu Glu Arg Tyr Ile
1               5                   10                  15

Leu Glu Ala Arg Glu Ala Glu Asn Val Thr Met Gly Cys Ala Glu Gly
            20                  25                  30

Cys Ser Phe Ser Glu Asn Ile Thr Val Pro Asp Thr Lys Val Asn Phe
        35                  40                  45

Tyr Thr Trp Lys Arg Met Asp Val Gly Gln Gln Ala Val Glu Val Trp
    50                  55                  60

Gln Gly Leu Ala Leu Leu Ser Glu Ala Ile Leu Arg Gly Gln Ala Leu
65                  70                  75                  80

Leu Ala Asn Ser Ser Gln Pro Ser Glu Thr Leu Gln Leu His Val Asp
                85                  90                  95

Lys Ala Val Ser Ser Leu Arg Ser Leu Thr Ser Leu Leu Arg Ala Leu
            100                 105                 110

Gly Ala Gln Lys Glu Ala Thr Ser Leu Pro Glu Ala Thr Ser Ala Ala
        115                 120                 125

Pro Leu Arg Thr Phe Thr Val Asp Thr Leu Cys Lys Leu Phe Arg Ile
    130                 135                 140

Tyr Ser Asn Phe Leu Arg Gly Lys Leu Thr Leu Tyr Thr Gly Glu Ala
145                 150                 155                 160

Cys Arg Arg Gly Asp Arg
```

<210> SEQ ID NO 14
<211> LENGTH: 166
<212> TYPE: PRT
<213> ORGANISM: Artificial Sequence
<220> FEATURE:
<223> OTHER INFORMATION: Feline EPO Analog 6-30 G18V87 mature form or
      "Analog 6-30 GV Mature"

<400> SEQUENCE: 14

Ala Pro Pro Arg Leu Ile Cys Asp Ser Arg Val Leu Glu Arg Tyr Ile
1               5                   10                  15

Leu Gly Ala Arg Glu Ala Glu Asn Val Thr Met Gly Cys Asn Glu Thr
            20                  25                  30

Cys Ser Phe Ser Glu Asn Ile Thr Val Pro Asp Thr Lys Val Asn Phe
        35                  40                  45

Tyr Thr Trp Lys Arg Met Asp Val Gly Gln Gln Ala Val Glu Val Trp
    50                  55                  60

Gln Gly Leu Ala Leu Leu Ser Glu Ala Ile Leu Arg Gly Gln Ala Leu
65                  70                  75                  80

Leu Ala Asn Ser Ser Gln Val Asn Glu Thr Leu Gln Leu His Val Asp
                85                  90                  95

Lys Ala Val Ser Ser Leu Arg Ser Leu Thr Ser Leu Leu Arg Ala Leu
            100                 105                 110

Gly Ala Gln Lys Glu Ala Thr Ser Leu Pro Glu Ala Thr Ser Ala Ala
        115                 120                 125

Pro Leu Arg Thr Phe Thr Val Asp Thr Leu Cys Lys Leu Phe Arg Ile
    130                 135                 140

Tyr Ser Asn Phe Leu Arg Gly Lys Leu Thr Leu Tyr Thr Gly Glu Ala
145                 150                 155                 160

Cys Arg Arg Gly Asp Arg
                165

<210> SEQ ID NO 15
<211> LENGTH: 166
<212> TYPE: PRT
<213> ORGANISM: Artificial Sequence
<220> FEATURE:
<223> OTHER INFORMATION: Feline EPO Analog 6-30 E18V87 mature form or
      "Analog 6-30 EV Mature"

<400> SEQUENCE: 15

Ala Pro Pro Arg Leu Ile Cys Asp Ser Arg Val Leu Glu Arg Tyr Ile
1               5                   10                  15

Leu Glu Ala Arg Glu Ala Glu Asn Val Thr Met Gly Cys Asn Glu Thr
            20                  25                  30

Cys Ser Phe Ser Glu Asn Ile Thr Val Pro Asp Thr Lys Val Asn Phe
        35                  40                  45

Tyr Thr Trp Lys Arg Met Asp Val Gly Gln Gln Ala Val Glu Val Trp
    50                  55                  60

Gln Gly Leu Ala Leu Leu Ser Glu Ala Ile Leu Arg Gly Gln Ala Leu
65                  70                  75                  80

Leu Ala Asn Ser Ser Gln Val Asn Glu Thr Leu Gln Leu His Val Asp
                85                  90                  95

Lys Ala Val Ser Ser Leu Arg Ser Leu Thr Ser Leu Leu Arg Ala Leu
            100                 105                 110

Gly Ala Gln Lys Glu Ala Thr Ser Leu Pro Glu Ala Thr Ser Ala Ala

```
            115                 120                 125
Pro Leu Arg Thr Phe Thr Val Asp Thr Leu Cys Lys Leu Phe Arg Ile
        130                 135                 140
Tyr Ser Asn Phe Leu Arg Gly Lys Leu Thr Tyr Thr Gly Glu Ala
145                 150                 155                 160
Cys Arg Arg Gly Asp Arg
                165

<210> SEQ ID NO 16
<211> LENGTH: 166
<212> TYPE: PRT
<213> ORGANISM: Artificial Sequence
<220> FEATURE:
<223> OTHER INFORMATION: Human erythropoietin second site mutation R103A

<400> SEQUENCE: 16

Ala Pro Pro Arg Leu Ile Cys Asp Ser Arg Val Leu Glu Arg Tyr Leu
1               5                   10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
65                  70                  75                  80
Leu Val Asn Ser Ser Gln Pro Trp Glu Pro Leu Gln Leu His Val Asp
                85                  90                  95
Lys Ala Val Ser Gly Leu Ala Ser Leu Thr Thr Leu Leu Arg Ala Leu
            100                 105                 110
Gly Ala Gln Lys Glu Ala Ile Ser Pro Pro Asp Ala Ala Ser Ala Ala
        115                 120                 125
Pro Leu Arg Thr Ile Thr Ala Asp Thr Phe Arg Lys Leu Phe Arg Val
    130                 135                 140
Tyr Ser Asn Phe Leu Arg Gly Lys Leu Lys Leu Tyr Thr Gly Glu Ala
145                 150                 155                 160
Cys Arg Thr Gly Asp Arg
                165

<210> SEQ ID NO 17
<211> LENGTH: 166
<212> TYPE: PRT
<213> ORGANISM: Artificial Sequence
<220> FEATURE:
<223> OTHER INFORMATION: Felis catus Erythropoietin second site mutation
      R103A

<400> SEQUENCE: 17

Ala Pro Pro Arg Leu Ile Cys Asp Ser Arg Val Leu Glu Arg Tyr Ile
1               5                   10                  15
Leu Glu Ala Arg Glu Ala Glu Asn Val Thr Met Gly Cys Ala Glu Gly
            20                  25                  30
Cys Ser Phe Ser Glu Asn Ile Thr Val Pro Asp Thr Lys Val Asn Phe
        35                  40                  45
Tyr Thr Trp Lys Arg Met Asp Val Gly Gln Gln Ala Val Glu Val Trp
    50                  55                  60
Gln Gly Leu Ala Leu Leu Ser Glu Ala Ile Leu Arg Gly Gln Ala Leu
65                  70                  75                  80
```

```
Leu Ala Asn Ser Ser Gln Pro Ser Glu Thr Leu Gln Leu His Val Asp
                85                  90                  95

Lys Ala Val Ser Ser Leu Ala Ser Leu Thr Ser Leu Leu Arg Ala Leu
            100                 105                 110

Gly Ala Gln Lys Glu Ala Thr Ser Leu Pro Glu Ala Thr Ser Ala Ala
        115                 120                 125

Pro Leu Arg Thr Phe Thr Val Asp Thr Leu Cys Lys Leu Phe Arg Ile
    130                 135                 140

Tyr Ser Asn Phe Leu Arg Gly Lys Leu Thr Leu Tyr Thr Gly Glu Ala
145                 150                 155                 160

Cys Arg Arg Gly Asp Arg
                165

<210> SEQ ID NO 18
<211> LENGTH: 166
<212> TYPE: PRT
<213> ORGANISM: Artificial Sequence
<220> FEATURE:
<223> OTHER INFORMATION: Canis lupus erythropoietin second site mutation
      R103A

<400> SEQUENCE: 18

Ala Pro Pro Arg Leu Ile Cys Asp Ser Arg Val Leu Glu Arg Tyr Ile
1               5                   10                  15

Leu Glu Ala Arg Glu Ala Glu Asn Val Thr Met Gly Cys Ala Gln Gly
            20                  25                  30

Cys Ser Phe Ser Glu Asn Ile Thr Val Pro Asp Thr Lys Val Asn Phe
        35                  40                  45

Tyr Thr Trp Lys Arg Met Asp Val Gly Gln Gln Ala Leu Glu Val Trp
    50                  55                  60

Gln Gly Leu Ala Leu Leu Ser Glu Ala Ile Leu Arg Gly Gln Ala Leu
65                  70                  75                  80

Leu Ala Asn Ala Ser Gln Pro Ser Glu Thr Pro Gln Leu His Val Asp
                85                  90                  95

Lys Ala Val Ser Ser Leu Ala Ser Leu Thr Ser Leu Leu Arg Ala Leu
            100                 105                 110

Gly Ala Gln Lys Glu Ala Met Ser Leu Pro Glu Glu Ala Ser Pro Ala
        115                 120                 125

Pro Leu Arg Thr Phe Thr Val Asp Thr Leu Cys Lys Leu Phe Arg Ile
    130                 135                 140

Tyr Ser Asn Phe Leu Arg Gly Lys Leu Thr Leu Tyr Thr Gly Glu Ala
145                 150                 155                 160

Cys Arg Arg Gly Asp Arg
                165

<210> SEQ ID NO 19
<211> LENGTH: 166
<212> TYPE: PRT
<213> ORGANISM: Artificial Sequence
<220> FEATURE:
<223> OTHER INFORMATION: Equus caballus erythropoietin second site
      mutation R103A

<400> SEQUENCE: 19

Ala Pro Pro Arg Leu Ile Cys Asp Ser Arg Val Leu Glu Arg Tyr Ile
1               5                   10                  15

Leu Glu Ala Arg Glu Ala Glu Asn Val Thr Met Gly Cys Ala Glu Gly
            20                  25                  30
```

```
Cys Ser Phe Gly Glu Asn Val Thr Val Pro Asp Thr Lys Val Asn Phe
        35                  40                  45

Tyr Ser Trp Lys Arg Met Glu Val Glu Gln Gln Ala Val Glu Val Trp
 50                  55                  60

Gln Gly Leu Ala Leu Leu Ser Glu Ala Ile Leu Gln Gly Gln Ala Leu
 65                  70                  75                  80

Leu Ala Asn Ser Ser Gln Pro Ser Glu Thr Leu Arg Leu His Val Asp
                85                  90                  95

Lys Ala Val Ser Ser Leu Ala Ser Leu Thr Ser Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Phe Ala Val Asp Thr Leu Cys Lys Leu Phe Arg Ile
        130                 135                 140

Tyr Ser Asn Phe Leu Arg Gly Lys Leu Lys Tyr Thr Gly Glu Ala
145                 150                 155                 160

Cys Arg Arg Gly Asp Arg
                165

<210> SEQ ID NO 20
<211> LENGTH: 508
<212> TYPE: PRT
<213> ORGANISM: Felis catus
<220> FEATURE:
<221> NAME/KEY: misc_feature
<222> LOCATION: (39)..(39)
<223> OTHER INFORMATION: Xaa can be any naturally occurring amino acid

<400> SEQUENCE: 20

Met Asp His Leu Trp Ala Pro Leu Trp Pro Gly Val Gly Ser Leu Cys
 1                   5                  10                  15

Leu Leu Leu Ala Gly Ala Ala Trp Ala Pro Pro Asn Pro Leu Asp
                20                  25                  30

Pro Lys Phe Glu Ser Lys Xaa Ala Leu Leu Ala Ala Arg Gly Pro Glu
             35                  40                  45

Glu Leu Leu Cys Phe Thr Glu Arg Leu Glu Asp Leu Val Cys Phe Trp
 50                  55                  60

Glu Glu Ala Ala Ser Ala Gly Val Gly Pro Asp Asn Tyr Ser Phe Phe
 65                  70                  75                  80

Tyr Gln Leu Glu Gly Glu Pro Trp Lys Pro Cys Ser Leu His Gln Ala
                85                  90                  95

Pro Thr Ala Arg Gly Ala Val Arg Phe Trp Cys Ser Leu Pro Thr Ala
            100                 105                 110

Asp Ala Ser Ser Phe Val Pro Leu Glu Leu Arg Val Thr Ala Val Ser
            115                 120                 125

Ser Gly Ala Pro Arg Tyr His Arg Ile Ile His Ile Asn Glu Val Val
        130                 135                 140

Leu Leu Asp Pro Pro Ala Gly Leu Leu Ala Arg Arg Ala Asp Glu Gly
145                 150                 155                 160

Gly His Val Val Leu Arg Trp Leu Pro Pro Pro Gly Ala Pro Val Ala
                165                 170                 175

Ser Leu Ile Arg Tyr Glu Val Asn Ile Ser Ser Gly Asn Val Ala Gly
            180                 185                 190

Gly Ala Gln Lys Val Glu Ile Leu Asp Gly Arg Thr Glu Cys Ala Leu
        195                 200                 205
```

```
Ser Asn Leu Arg Gly Arg Thr Arg Tyr Thr Phe Met Val Arg Ala Arg
    210                 215                 220

Met Ala Glu Pro Ser Phe Gly Gly Phe Trp Ser Ala Trp Ser Glu Pro
225                 230                 235                 240

Ala Ser Leu Leu Thr Ala Ser Asp Leu Asp Pro Leu Ile Leu Thr Leu
                245                 250                 255

Ser Leu Ile Leu Val Leu Ile Leu Leu Leu Ala Val Leu Ala Leu
            260                 265                 270

Leu Ser His Arg Arg Thr Leu Lys Gln Lys Ile Trp Pro Gly Ile Pro
            275                 280                 285

Ser Pro Glu Ser Glu Phe Glu Gly Leu Phe Thr Thr His Lys Gly Asn
    290                 295                 300

Phe Gln Leu Trp Leu Tyr Gln Asn Glu Gly Cys Leu Trp Trp Ser Pro
305                 310                 315                 320

Cys Ala Pro Phe Ala Glu Asp Pro Pro Ser Pro Leu Glu Val Leu Ser
                325                 330                 335

Glu Arg Cys Trp Gly Ala Thr Gln Ala Ala Glu Pro Gly Ala Glu Glu
            340                 345                 350

Gly Pro Leu Leu Glu Pro Leu Gly Ser Glu His Thr Gln Asp Thr Tyr
    355                 360                 365

Leu Val Leu Asp Lys Trp Leu Leu Pro Arg Asn Pro Pro Ser Glu Asp
370                 375                 380

Leu Pro Arg Pro Asp Gly Ser Leu Asp Met Val Ala Met His Lys Gly
385                 390                 395                 400

Ser Glu Ala Ser Ser Cys Ser Ser Ala Leu Ser Leu Lys Pro Gly Pro
                405                 410                 415

Glu Gly Ala Leu Gly Ala Ser Phe Glu Tyr Thr Ile Leu Asp Pro Ser
            420                 425                 430

Ser Gln Leu Leu Arg Pro Arg Ala Leu Pro Pro Glu Leu Pro Pro Thr
        435                 440                 445

Pro Pro His Ile Lys Tyr Leu Tyr Leu Met Val Ser Asp Ser Gly Ile
    450                 455                 460

Ser Thr Asp Tyr Ser Ser Gly Gly Ser Gln Glu Ala Gln Gly Asp Ser
465                 470                 475                 480

Ser Thr Gly Pro Tyr Leu Asn Pro Tyr Glu Asn Ser Leu Ile Pro Ala
                485                 490                 495

Thr Glu Thr Ser Pro Pro Ser Tyr Val Ala Cys Ser
            500                 505

<210> SEQ ID NO 21
<211> LENGTH: 508
<212> TYPE: PRT
<213> ORGANISM: Artificial Sequence
<220> FEATURE:
<223> OTHER INFORMATION: Felis catus EPO receptor EPOR203_39A

<400> SEQUENCE: 21

Met Asp His Leu Trp Ala Pro Leu Trp Pro Gly Val Gly Ser Leu Cys
1               5                   10                  15

Leu Leu Leu Ala Gly Ala Ala Trp Ala Pro Pro Asn Pro Leu Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
    50                  55                  60
```

```
Glu Glu Ala Ala Ser Ala Gly Val Gly Pro Asp Asn Tyr Ser Phe Phe
 65                  70                  75                  80

Tyr Gln Leu Glu Gly Glu Pro Trp Lys Pro Cys Ser Leu His Gln Ala
                 85                  90                  95

Pro Thr Ala Arg Gly Ala Val Arg Phe Trp Cys Ser Leu Pro Thr Ala
            100                 105                 110

Asp Ala Ser Ser Phe Val Pro Leu Glu Leu Arg Val Thr Ala Val Ser
        115                 120                 125

Ser Gly Ala Pro Arg Tyr His Arg Ile Ile His Ile Asn Glu Val Val
    130                 135                 140

Leu Leu Asp Pro Pro Ala Gly Leu Leu Ala Arg Arg Ala Asp Glu Gly
145                 150                 155                 160

Gly His Val Val Leu Arg Trp Leu Pro Pro Gly Ala Pro Val Ala
                165                 170                 175

Ser Leu Ile Arg Tyr Glu Val Asn Ile Ser Ser Gly Asn Val Ala Gly
                180                 185                 190

Gly Ala Gln Lys Val Glu Ile Leu Asp Gly Arg Thr Glu Cys Ala Leu
            195                 200                 205

Ser Asn Leu Arg Gly Arg Thr Arg Tyr Thr Phe Met Val Arg Ala Arg
210                 215                 220

Met Ala Glu Pro Ser Phe Gly Gly Phe Trp Ser Ala Trp Ser Glu Pro
225                 230                 235                 240

Ala Ser Leu Leu Thr Ala Ser Asp Leu Asp Pro Leu Ile Leu Thr Leu
                245                 250                 255

Ser Leu Ile Leu Val Leu Ile Leu Leu Leu Ala Val Leu Ala Leu
                260                 265                 270

Leu Ser His Arg Arg Thr Leu Lys Gln Lys Ile Trp Pro Gly Ile Pro
        275                 280                 285

Ser Pro Glu Ser Glu Phe Glu Gly Leu Phe Thr Thr His Lys Gly Asn
    290                 295                 300

Phe Gln Leu Trp Leu Tyr Gln Asn Glu Gly Cys Leu Trp Trp Ser Pro
305                 310                 315                 320

Cys Ala Pro Phe Ala Glu Asp Pro Pro Ser Pro Leu Glu Val Leu Ser
                325                 330                 335

Glu Arg Cys Trp Gly Ala Thr Gln Ala Ala Glu Pro Gly Ala Glu Glu
            340                 345                 350

Gly Pro Leu Leu Glu Pro Leu Gly Ser Glu His Thr Gln Asp Thr Tyr
        355                 360                 365

Leu Val Leu Asp Lys Trp Leu Leu Pro Arg Asn Pro Pro Ser Glu Asp
370                 375                 380

Leu Pro Arg Pro Asp Gly Ser Leu Asp Met Val Ala Met His Lys Gly
385                 390                 395                 400

Ser Glu Ala Ser Ser Cys Ser Ser Ala Leu Ser Leu Lys Pro Gly Pro
                405                 410                 415

Glu Gly Ala Leu Gly Ala Ser Phe Glu Tyr Thr Ile Leu Asp Pro Ser
            420                 425                 430

Ser Gln Leu Leu Arg Pro Arg Ala Leu Pro Pro Glu Leu Pro Pro Thr
        435                 440                 445

Pro Pro His Ile Lys Tyr Leu Tyr Leu Met Val Ser Asp Ser Gly Ile
    450                 455                 460

Ser Thr Asp Tyr Ser Ser Gly Gly Ser Gln Glu Ala Gln Gly Asp Ser
465                 470                 475                 480

Ser Thr Gly Pro Tyr Leu Asn Pro Tyr Glu Asn Ser Leu Ile Pro Ala
```

```
                      485                 490                 495
Thr Glu Thr Ser Pro Pro Ser Tyr Val Ala Cys Ser
                500                 505

<210> SEQ ID NO 22
<211> LENGTH: 486
<212> TYPE: PRT
<213> ORGANISM: Artificial Sequence
<220> FEATURE:
<223> OTHER INFORMATION: Feline EPOR203_39A_ECD_Fc

<400> SEQUENCE: 22

Met Asp His Leu Trp Ala Pro Leu Trp Pro Gly Val Gly Ser Leu Cys
1               5                   10                  15

Leu Leu Leu Ala Gly Ala Ala Trp Ala Pro Pro Asn Pro Leu Asp
            20                  25                  30

Pro Lys Phe Glu Ser Lys Ala Ala Leu Leu Ala Ala Arg Gly Pro Glu
        35                  40                  45

Glu Leu Leu Cys Phe Thr Glu Arg Leu Glu Asp Leu Val Cys Phe Trp
    50                  55                  60

Glu Glu Ala Ala Ser Ala Gly Val Gly Pro Asp Asn Tyr Ser Phe Phe
65                  70                  75                  80

Tyr Gln Leu Glu Gly Glu Pro Trp Lys Pro Cys Ser Leu His Gln Ala
                85                  90                  95

Pro Thr Ala Arg Gly Ala Val Arg Phe Trp Cys Ser Leu Pro Thr Ala
            100                 105                 110

Asp Ala Ser Ser Phe Val Pro Leu Glu Leu Arg Val Thr Ala Val Ser
        115                 120                 125

Ser Gly Ala Pro Arg Tyr His Arg Ile Ile His Ile Asn Glu Val Val
    130                 135                 140

Leu Leu Asp Pro Pro Ala Gly Leu Leu Ala Arg Arg Ala Asp Glu Gly
145                 150                 155                 160

Gly His Val Val Leu Arg Trp Leu Pro Pro Gly Ala Pro Val Ala
                165                 170                 175

Ser Leu Ile Arg Tyr Glu Val Asn Ile Ser Ser Gly Asn Val Ala Gly
            180                 185                 190

Gly Ala Gln Lys Val Glu Ile Leu Asp Gly Arg Thr Glu Cys Ala Leu
        195                 200                 205

Ser Asn Leu Arg Gly Arg Thr Arg Tyr Thr Phe Met Val Arg Ala Arg
    210                 215                 220

Met Ala Glu Pro Ser Phe Gly Gly Phe Trp Ser Ala Trp Ser Glu Pro
225                 230                 235                 240

Ala Ser Leu Leu Thr Ala Ser Asp Leu Asp Pro Gly Gly Gly Ser Pro
                245                 250                 255

Lys Ser Cys Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
    290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
```

```
            340                 345                 350
Leu Asn Gly Lys Glu Tyr Lys Cys Lys Val Ser Asn Lys Ala Leu Pro
            355                 360                 365

Ala Pro Ile Glu Lys Thr Ile Ser Lys Ala Lys Gly Gln Pro Arg Glu
    370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Lys
        435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys
                485

<210> SEQ ID NO 23
<211> LENGTH: 226
<212> TYPE: PRT
<213> ORGANISM: Artificial Sequence
<220> FEATURE:
<223> OTHER INFORMATION: Feline EPOR201 ECD

<400> SEQUENCE: 23

Pro Pro Pro Asn Pro Leu Asp Pro Lys Phe Glu Ser Lys Val Asn Met
1               5                   10                  15

Val Cys Met Arg Ala Pro Glu Ala Ser Ala Cys Gly Ser Ser Glu Arg
            20                  25                  30

Leu Glu Asp Leu Val Cys Phe Trp Glu Glu Ala Ala Ser Ala Gly Val
        35                  40                  45

Gly Pro Asp Asn Tyr Ser Phe Phe Tyr Gln Leu Glu Gly Glu Pro Trp
    50                  55                  60

Lys Pro Cys Ser Leu His Gln Ala Pro Thr Ala Arg Gly Ala Val Arg
65                  70                  75                  80

Phe Trp Cys Ser Leu Pro Thr Ala Asp Ala Ser Ser Phe Val Pro Leu
                85                  90                  95

Glu Leu Arg Val Thr Ala Val Ser Ser Gly Ala Pro Arg Tyr His Arg
            100                 105                 110

Ile Ile His Ile Asn Glu Val Val Leu Leu Asp Pro Pro Ala Gly Leu
        115                 120                 125

Leu Ala Arg Arg Ala Asp Glu Gly Gly His Val Val Leu Arg Trp Leu
    130                 135                 140

Pro Pro Pro Gly Ala Pro Val Ala Ser Leu Ile Arg Tyr Glu Val Asn
145                 150                 155                 160

Ile Ser Ser Gly Asn Val Ala Gly Gly Ala Gln Lys Val Glu Ile Leu
                165                 170                 175

Asp Gly Arg Thr Glu Cys Ala Leu Ser Asn Leu Arg Gly Arg Thr Arg
            180                 185                 190

Tyr Thr Phe Met Val Arg Ala Arg Met Ala Glu Pro Ser Phe Gly Gly
        195                 200                 205

Phe Trp Ser Ala Trp Ser Glu Pro Ala Ser Leu Leu Thr Ala Ser Asp
```

```
                    210                 215                 220

Leu Asp
225

<210> SEQ ID NO 24
<211> LENGTH: 228
<212> TYPE: PRT
<213> ORGANISM: Artificial Sequence
<220> FEATURE:
<223> OTHER INFORMATION: Feline EPOR202 ECD

<400> SEQUENCE: 24

Pro Pro Pro Asn Pro Leu Asp Pro Lys Phe Glu Ser Lys Gly Lys Asp
1               5                   10                  15

Gly Ser Val Cys Arg Pro Pro Gln Trp Phe Leu Glu Gly Asn Ala Glu
            20                  25                  30

Glu Arg Leu Glu Asp Leu Val Cys Phe Trp Glu Glu Ala Ala Ser Ala
        35                  40                  45

Gly Val Gly Pro Asp Asn Tyr Ser Phe Phe Tyr Gln Leu Glu Gly Glu
    50                  55                  60

Pro Trp Lys Pro Cys Ser Leu His Gln Ala Pro Thr Ala Arg Gly Ala
65                  70                  75                  80

Val Arg Phe Trp Cys Ser Leu Pro Thr Ala Asp Ala Ser Ser Phe Val
                85                  90                  95

Pro Leu Glu Leu Arg Val Thr Ala Val Ser Ser Gly Ala Pro Arg Tyr
            100                 105                 110

His Arg Ile Ile His Ile Asn Glu Val Val Leu Leu Asp Pro Pro Ala
        115                 120                 125

Gly Leu Leu Ala Arg Arg Ala Asp Glu Gly Gly His Val Val Leu Arg
    130                 135                 140

Trp Leu Pro Pro Pro Gly Ala Pro Val Ala Ser Leu Ile Arg Tyr Glu
145                 150                 155                 160

Val Asn Ile Ser Ser Gly Asn Val Ala Gly Gly Ala Gln Lys Val Glu
                165                 170                 175

Ile Leu Asp Gly Arg Thr Glu Cys Ala Leu Ser Asn Leu Arg Gly Arg
            180                 185                 190

Thr Arg Tyr Thr Phe Met Val Arg Ala Arg Met Ala Glu Pro Ser Phe
        195                 200                 205

Gly Gly Phe Trp Ser Ala Trp Ser Glu Pro Ala Ser Leu Leu Thr Ala
    210                 215                 220

Ser Asp Leu Asp
225

<210> SEQ ID NO 25
<211> LENGTH: 226
<212> TYPE: PRT
<213> ORGANISM: Artificial Sequence
<220> FEATURE:
<223> OTHER INFORMATION: Feline EPOR203 ECD
<220> FEATURE:
<221> NAME/KEY: misc_feature
<222> LOCATION: (14)..(14)
<223> OTHER INFORMATION: Xaa can be any naturally occurring amino acid

<400> SEQUENCE: 25

Pro Pro Pro Asn Pro Leu Asp Pro Lys Phe Glu Ser Lys Xaa Ala Leu
1               5                   10                  15

Leu Ala Ala Arg Gly Pro Glu Glu Leu Leu Cys Phe Thr Glu Arg Leu
            20                  25                  30
```

```
Glu Asp Leu Val Cys Phe Trp Glu Glu Ala Ala Ser Ala Gly Val Gly
            35                  40                  45

Pro Asp Asn Tyr Ser Phe Phe Tyr Gln Leu Glu Gly Glu Pro Trp Lys
 50                  55                  60

Pro Cys Ser Leu His Gln Ala Pro Thr Ala Arg Gly Ala Val Arg Phe
 65                  70                  75                  80

Trp Cys Ser Leu Pro Thr Ala Asp Ala Ser Ser Phe Val Pro Leu Glu
                 85                  90                  95

Leu Arg Val Thr Ala Val Ser Ser Gly Ala Pro Arg Tyr His Arg Ile
            100                 105                 110

Ile His Ile Asn Glu Val Val Leu Leu Asp Pro Pro Ala Gly Leu Leu
        115                 120                 125

Ala Arg Arg Ala Asp Glu Gly Gly His Val Val Leu Arg Trp Leu Pro
130                 135                 140

Pro Pro Gly Ala Pro Val Ala Ser Leu Ile Arg Tyr Glu Val Asn Ile
145                 150                 155                 160

Ser Ser Gly Asn Val Ala Gly Gly Ala Gln Lys Val Glu Ile Leu Asp
                165                 170                 175

Gly Arg Thr Glu Cys Ala Leu Ser Asn Leu Arg Gly Thr Arg Tyr
            180                 185                 190

Thr Phe Met Val Arg Ala Arg Met Ala Glu Pro Ser Phe Gly Gly Phe
            195                 200                 205

Trp Ser Ala Trp Ser Glu Pro Ala Ser Leu Leu Thr Ala Ser Asp Leu
210                 215                 220

Asp Pro
225

<210> SEQ ID NO 26
<211> LENGTH: 226
<212> TYPE: PRT
<213> ORGANISM: Artificial Sequence
<220> FEATURE:
<223> OTHER INFORMATION: Feline EPOR203_39A ECD

<400> SEQUENCE: 26

Pro Pro Pro Asn Pro Leu Asp Pro Lys Phe Glu Ser Lys Ala Ala Leu
 1               5                  10                  15

Leu Ala Ala Arg Gly Pro Glu Glu Leu Leu Cys Phe Thr Glu Arg Leu
            20                  25                  30

Glu Asp Leu Val Cys Phe Trp Glu Glu Ala Ala Ser Ala Gly Val Gly
            35                  40                  45

Pro Asp Asn Tyr Ser Phe Phe Tyr Gln Leu Glu Gly Glu Pro Trp Lys
 50                  55                  60

Pro Cys Ser Leu His Gln Ala Pro Thr Ala Arg Gly Ala Val Arg Phe
 65                  70                  75                  80

Trp Cys Ser Leu Pro Thr Ala Asp Ala Ser Ser Phe Val Pro Leu Glu
                 85                  90                  95

Leu Arg Val Thr Ala Val Ser Ser Gly Ala Pro Arg Tyr His Arg Ile
            100                 105                 110

Ile His Ile Asn Glu Val Val Leu Leu Asp Pro Pro Ala Gly Leu Leu
        115                 120                 125

Ala Arg Arg Ala Asp Glu Gly Gly His Val Val Leu Arg Trp Leu Pro
130                 135                 140

Pro Pro Gly Ala Pro Val Ala Ser Leu Ile Arg Tyr Glu Val Asn Ile
145                 150                 155                 160
```

```
Ser Ser Gly Asn Val Ala Gly Ala Gln Lys Val Glu Ile Leu Asp
            165                 170                 175

Gly Arg Thr Glu Cys Ala Leu Ser Asn Leu Arg Gly Arg Thr Arg Tyr
            180                 185                 190

Thr Phe Met Val Arg Ala Arg Met Ala Glu Pro Ser Phe Gly Gly Phe
            195                 200                 205

Trp Ser Ala Trp Ser Glu Pro Ala Ser Leu Leu Thr Ala Ser Asp Leu
210                 215                 220

Asp Pro
225

<210> SEQ ID NO 27
<211> LENGTH: 512
<212> TYPE: PRT
<213> ORGANISM: Felis catus

<400> SEQUENCE: 27

Met Asp His Leu Trp Ala Pro Leu Trp Pro Gly Val Gly Ser Leu Cys
1               5                   10                  15

Leu Leu Leu Ala Gly Ala Ala Trp Ala Pro Pro Asn Pro Leu Asp
            20                  25                  30

Pro Lys Phe Glu Ser Lys Val Asn Met Val Cys Met Arg Ala Pro Glu
            35                  40                  45

Ala Ser Ala Cys Gly Ser Ser Glu Arg Leu Glu Asp Leu Val Cys Phe
        50                  55                  60

Trp Glu Glu Ala Ala Ser Ala Gly Val Gly Pro Asp Asn Tyr Ser Phe
65                  70                  75                  80

Phe Tyr Gln Leu Glu Gly Glu Pro Trp Lys Pro Cys Ser Leu His Gln
                85                  90                  95

Ala Pro Thr Ala Arg Gly Ala Val Arg Phe Trp Cys Ser Leu Pro Thr
            100                 105                 110

Ala Asp Ala Ser Ser Phe Val Pro Leu Glu Leu Arg Val Thr Ala Val
        115                 120                 125

Ser Ser Gly Ala Pro Arg Tyr His Arg Ile Ile His Ile Asn Glu Val
    130                 135                 140

Val Leu Leu Asp Pro Pro Ala Gly Leu Leu Ala Arg Arg Ala Asp Glu
145                 150                 155                 160

Gly Gly His Val Val Leu Arg Trp Leu Pro Pro Pro Gly Ala Pro Val
                165                 170                 175

Ala Ser Leu Ile Arg Tyr Glu Val Asn Ile Ser Ser Gly Asn Val Ala
            180                 185                 190

Gly Gly Ala Gln Lys Val Glu Ile Leu Asp Gly Arg Thr Glu Cys Ala
        195                 200                 205

Leu Ser Asn Leu Arg Gly Arg Thr Arg Tyr Thr Phe Met Val Arg Ala
    210                 215                 220

Arg Met Ala Glu Pro Ser Phe Gly Gly Phe Trp Ser Ala Trp Ser Glu
225                 230                 235                 240

Pro Ala Ser Leu Leu Thr Ala Ser Asp Leu Asp Pro Leu Ile Leu Thr
                245                 250                 255

Leu Ser Leu Ile Leu Val Leu Ile Leu Leu Leu Ala Val Leu Ala
            260                 265                 270

Leu Leu Ser His Arg Arg Phe Thr Arg Thr Leu Lys Gln Lys Ile Trp
        275                 280                 285

Pro Gly Ile Pro Ser Pro Glu Ser Glu Phe Glu Gly Leu Phe Thr Thr
```

```
                290                 295                 300
His Lys Gly Asn Phe Gln Leu Trp Leu Tyr Gln Asn Glu Gly Cys Leu
305                 310                 315                 320

Trp Trp Ser Pro Cys Ala Pro Phe Ala Glu Asp Pro Ser Pro Leu
                325                 330                 335

Glu Val Leu Ser Glu Arg Cys Trp Gly Ala Thr Gln Ala Ala Glu Pro
                340                 345                 350

Gly Ala Glu Glu Gly Pro Leu Leu Glu Pro Leu Gly Ser Glu His Thr
                355                 360                 365

Gln Asp Thr Tyr Leu Val Leu Asp Lys Trp Leu Leu Pro Arg Asn Pro
                370                 375                 380

Pro Ser Glu Asp Leu Pro Arg Pro Asp Gly Ser Leu Asp Met Val Ala
385                 390                 395                 400

Met His Lys Gly Ser Glu Ala Ser Ser Cys Ser Ser Ala Leu Ser Leu
                405                 410                 415

Lys Pro Gly Pro Glu Gly Ala Leu Gly Ala Ser Phe Glu Tyr Thr Ile
                420                 425                 430

Leu Asp Pro Ser Ser Gln Leu Leu Arg Pro Arg Ala Leu Pro Pro Glu
                435                 440                 445

Leu Pro Pro Thr Pro Pro His Ile Lys Tyr Leu Tyr Leu Met Val Ser
                450                 455                 460

Asp Ser Gly Ile Ser Thr Asp Tyr Ser Ser Gly Gly Ser Gln Glu Ala
465                 470                 475                 480

Gln Gly Asp Ser Ser Thr Gly Pro Tyr Leu Asn Pro Tyr Glu Asn Ser
                485                 490                 495

Leu Ile Pro Ala Thr Glu Thr Ser Pro Pro Ser Tyr Val Ala Cys Ser
                500                 505                 510
```

<210> SEQ ID NO 28
<211> LENGTH: 511
<212> TYPE: PRT
<213> ORGANISM: Artificial Sequence
<220> FEATURE:
<223> OTHER INFORMATION: Felis catus EPO receptor Sequence EPOR202

<400> SEQUENCE: 28

```
Met Asp His Leu Trp Ala Pro Leu Trp Pro Gly Val Gly Ser Leu Cys
1               5                   10                  15

Leu Leu Leu Ala Gly Ala Ala Trp Ala Pro Pro Asn Pro Leu Asp
                20                  25                  30

Pro Lys Phe Glu Ser Lys Gly Lys Asp Gly Ser Val Cys Arg Pro Pro
                35                  40                  45

Gln Trp Phe Leu Glu Gly Asn Ala Glu Arg Leu Glu Asp Leu Val
                50                  55                  60

Cys Phe Trp Glu Glu Ala Ala Ser Ala Gly Val Gly Pro Asp Asn Tyr
65                  70                  75                  80

Ser Phe Phe Tyr Gln Leu Glu Gly Glu Pro Trp Lys Pro Cys Ser Leu
                85                  90                  95

His Gln Ala Pro Thr Ala Arg Gly Ala Val Arg Phe Trp Cys Ser Leu
                100                 105                 110

Pro Thr Ala Asp Ala Ser Ser Phe Val Pro Leu Glu Leu Arg Val Thr
                115                 120                 125

Ala Val Ser Ser Gly Ala Pro Arg Tyr His Arg Ile Ile His Ile Asn
                130                 135                 140

Glu Val Val Leu Leu Asp Pro Pro Ala Gly Leu Leu Ala Arg Arg Ala
```

```
            145                 150                 155                 160
Asp Glu Gly Gly His Val Val Leu Arg Trp Leu Pro Pro Gly Ala
                165                 170                 175
Pro Val Ala Ser Leu Ile Arg Tyr Glu Val Asn Ile Ser Ser Gly Asn
            180                 185                 190
Val Ala Gly Gly Ala Gln Lys Val Glu Ile Leu Asp Gly Arg Thr Glu
                195                 200                 205
Cys Ala Leu Ser Asn Leu Arg Gly Arg Thr Arg Tyr Thr Phe Met Val
    210                 215                 220
Arg Ala Arg Met Ala Glu Pro Ser Phe Gly Gly Phe Trp Ser Ala Trp
225                 230                 235                 240
Ser Glu Pro Ala Ser Leu Leu Thr Ala Ser Asp Leu Asp Pro Leu Ile
                245                 250                 255
Leu Thr Leu Ser Leu Ile Leu Val Leu Ile Leu Leu Leu Ala Val
                260                 265                 270
Leu Ala Leu Leu Ser His Arg Arg Thr Leu Lys Gln Lys Ile Trp Pro
            275                 280                 285
Gly Ile Pro Ser Pro Glu Ser Glu Phe Glu Gly Leu Phe Thr Thr His
    290                 295                 300
Lys Gly Asn Phe Gln Leu Trp Leu Tyr Gln Asn Glu Gly Cys Leu Trp
305                 310                 315                 320
Trp Ser Pro Cys Ala Pro Phe Ala Glu Asp Pro Pro Ser Pro Leu Glu
                325                 330                 335
Val Leu Ser Glu Arg Cys Trp Gly Ala Thr Gln Ala Ala Glu Pro Gly
                340                 345                 350
Ala Glu Glu Gly Pro Leu Leu Glu Pro Leu Gly Ser Glu His Thr Gln
            355                 360                 365
Asp Thr Tyr Leu Val Leu Asp Lys Trp Leu Leu Pro Arg Asn Pro Pro
    370                 375                 380
Ser Glu Asp Leu Pro Arg Pro Asp Gly Ser Leu Asp Met Val Ala Met
385                 390                 395                 400
His Lys Gly Ser Glu Ala Ser Ser Cys Ser Ser Ala Leu Ser Leu Lys
                405                 410                 415
Pro Gly Pro Glu Gly Ala Leu Gly Ala Ser Phe Glu Tyr Thr Ile Leu
                420                 425                 430
Asp Pro Ser Ser Gln Leu Leu Arg Pro Arg Ala Leu Pro Pro Glu Leu
            435                 440                 445
Pro Pro Thr Pro Pro His Ile Lys Tyr Leu Tyr Leu Met Val Ser Asp
    450                 455                 460
Ser Gly Ile Ser Thr Asp Tyr Ser Ser Gly Gly Ser Gln Glu Ala Gln
465                 470                 475                 480
Gly Asp Ser Ser Thr Gly Pro Tyr Leu Asn Pro Tyr Glu Asn Ser Leu
                485                 490                 495
Ile Pro Ala Thr Glu Thr Ser Pro Pro Ser Tyr Val Ala Cys Ser
                500                 505                 510
```

<210> SEQ ID NO 29
<211> LENGTH: 215
<212> TYPE: PRT
<213> ORGANISM: Artificial Sequence
<220> FEATURE:
<223> OTHER INFORMATION: Feline EPOR201 ECD (minimal)

<400> SEQUENCE: 29

Asp Pro Lys Phe Glu Ser Lys Val Asn Met Val Cys Met Arg Ala Pro

```
            1               5                   10                  15
          Glu Ala Ser Ala Cys Gly Ser Ser Glu Arg Leu Glu Asp Leu Val Cys
                       20                  25                  30

Phe Trp Glu Glu Ala Ala Ser Ala Gly Val Gly Pro Asp Asn Tyr Ser
                       35                  40                  45

Phe Phe Tyr Gln Leu Glu Gly Glu Pro Trp Lys Pro Cys Ser Leu His
           50                  55                  60

Gln Ala Pro Thr Ala Arg Gly Ala Val Arg Phe Trp Cys Ser Leu Pro
           65                  70                  75                  80

Thr Ala Asp Ala Ser Ser Phe Val Pro Leu Glu Leu Arg Val Thr Ala
                       85                  90                  95

Val Ser Ser Gly Ala Pro Arg Tyr His Arg Ile Ile His Ile Asn Glu
                       100                 105                 110

Val Val Leu Leu Asp Pro Pro Ala Gly Leu Leu Ala Arg Arg Ala Asp
                       115                 120                 125

Glu Gly Gly His Val Val Leu Arg Trp Leu Pro Pro Gly Ala Pro
                       130                 135                 140

Val Ala Ser Leu Ile Arg Tyr Glu Val Asn Ile Ser Ser Gly Asn Val
           145                 150                 155                 160

Ala Gly Gly Ala Gln Lys Val Glu Ile Leu Asp Gly Arg Thr Glu Cys
                       165                 170                 175

Ala Leu Ser Asn Leu Arg Gly Arg Thr Arg Tyr Thr Phe Met Val Arg
                       180                 185                 190

Ala Arg Met Ala Glu Pro Ser Phe Gly Gly Phe Trp Ser Ala Trp Ser
                       195                 200                 205

Glu Pro Ala Ser Leu Leu Thr
                       210                 215

<210> SEQ ID NO 30
<211> LENGTH: 217
<212> TYPE: PRT
<213> ORGANISM: Artificial Sequence
<220> FEATURE:
<223> OTHER INFORMATION: Feline EPOR202 ECD (minimal)

<400> SEQUENCE: 30

Asp Pro Lys Phe Glu Ser Lys Gly Lys Asp Gly Ser Val Cys Arg Pro
           1               5                   10                  15

Pro Gln Trp Phe Leu Glu Gly Asn Ala Glu Glu Arg Leu Glu Asp Leu
                       20                  25                  30

Val Cys Phe Trp Glu Glu Ala Ala Ser Ala Gly Val Gly Pro Asp Asn
                       35                  40                  45

Tyr Ser Phe Phe Tyr Gln Leu Glu Gly Glu Pro Trp Lys Pro Cys Ser
           50                  55                  60

Leu His Gln Ala Pro Thr Ala Arg Gly Ala Val Arg Phe Trp Cys Ser
           65                  70                  75                  80

Leu Pro Thr Ala Asp Ala Ser Ser Phe Val Pro Leu Glu Leu Arg Val
                       85                  90                  95

Thr Ala Val Ser Ser Gly Ala Pro Arg Tyr His Arg Ile Ile His Ile
                       100                 105                 110

Asn Glu Val Val Leu Leu Asp Pro Pro Ala Gly Leu Leu Ala Arg Arg
                       115                 120                 125

Ala Asp Glu Gly Gly His Val Val Leu Arg Trp Leu Pro Pro Gly
                       130                 135                 140

Ala Pro Val Ala Ser Leu Ile Arg Tyr Glu Val Asn Ile Ser Ser Gly
```

```
                145                 150                 155                 160
Asn Val Ala Gly Gly Ala Gln Lys Val Glu Ile Leu Asp Gly Arg Thr
                    165                 170                 175

Glu Cys Ala Leu Ser Asn Leu Arg Gly Arg Thr Arg Tyr Thr Phe Met
                180                 185                 190

Val Arg Ala Arg Met Ala Glu Pro Ser Phe Gly Gly Phe Trp Ser Ala
                195                 200                 205

Trp Ser Glu Pro Ala Ser Leu Leu Thr
            210                 215

<210> SEQ ID NO 31
<211> LENGTH: 214
<212> TYPE: PRT
<213> ORGANISM: Artificial Sequence
<220> FEATURE:
<223> OTHER INFORMATION: Feline EPOR203 ECD (minimal)

<400> SEQUENCE: 31

Asp Pro Lys Phe Glu Ser Lys Ala Ala Leu Leu Ala Ala Arg Gly Pro
1               5                   10                  15

Glu Glu Leu Leu Cys Phe Thr Glu Arg Leu Glu Asp Leu Val Cys Phe
                20                  25                  30

Trp Glu Glu Ala Ala Ser Ala Gly Val Gly Pro Asp Asn Tyr Ser Phe
            35                  40                  45

Phe Tyr Gln Leu Glu Gly Glu Pro Trp Lys Pro Cys Ser Leu His Gln
        50                  55                  60

Ala Pro Thr Ala Arg Gly Ala Val Arg Phe Trp Cys Ser Leu Pro Thr
65                  70                  75                  80

Ala Asp Ala Ser Ser Phe Val Pro Leu Glu Leu Arg Val Thr Ala Val
                85                  90                  95

Ser Ser Gly Ala Pro Arg Tyr His Arg Ile Ile His Ile Asn Glu Val
                100                 105                 110

Val Leu Leu Asp Pro Pro Ala Gly Leu Leu Ala Arg Arg Ala Asp Glu
            115                 120                 125

Gly Gly His Val Val Leu Arg Trp Leu Pro Pro Gly Ala Pro Val
        130                 135                 140

Ala Ser Leu Ile Arg Tyr Glu Val Asn Ile Ser Ser Gly Asn Val Ala
145                 150                 155                 160

Gly Gly Ala Gln Lys Val Glu Ile Leu Asp Gly Arg Thr Glu Cys Ala
                165                 170                 175

Leu Ser Asn Leu Arg Gly Arg Thr Arg Tyr Thr Phe Met Val Arg Ala
                180                 185                 190

Arg Met Ala Glu Pro Ser Phe Gly Gly Phe Trp Ser Ala Trp Ser Glu
                195                 200                 205

Pro Ala Ser Leu Leu Thr
            210

<210> SEQ ID NO 32
<211> LENGTH: 508
<212> TYPE: PRT
<213> ORGANISM: Felis catus
<220> FEATURE:
<221> NAME/KEY: misc_feature
<222> LOCATION: (50)..(53)
<223> OTHER INFORMATION: Xaa can be any naturally occurring amino acid

<400> SEQUENCE: 32

Met Asp His Leu Trp Ala Pro Leu Trp Pro Gly Val Gly Ser Leu Cys
```

-continued

```
1               5                   10                  15
Leu Leu Leu Ala Gly Ala Ala Trp Ala Pro Pro Asn Pro Leu Asp
                20                  25                  30
Pro Lys Phe Glu Ser Lys Gly Lys Asp Gly Ser Val Cys Arg Pro Pro
            35                  40                  45
Gln Xaa Xaa Xaa Thr Glu Arg Leu Glu Asp Leu Val Cys Phe Trp
        50                  55                  60
Glu Glu Ala Ala Ser Ala Gly Val Gly Pro Asp Asn Tyr Ser Phe Phe
65                  70                  75                  80
Tyr Gln Leu Glu Gly Glu Pro Trp Lys Pro Cys Ser Leu His Gln Ala
                85                  90                  95
Pro Thr Ala Arg Gly Ala Val Arg Phe Trp Cys Ser Leu Pro Thr Ala
                100                 105                 110
Asp Ala Ser Ser Phe Val Pro Leu Glu Leu Arg Val Thr Ala Val Ser
                115                 120                 125
Ser Gly Ala Pro Arg Tyr His Arg Ile Ile His Ile Asn Glu Val Val
    130                 135                 140
Leu Leu Asp Pro Pro Ala Gly Leu Leu Ala Arg Arg Ala Asp Glu Gly
145                 150                 155                 160
Gly His Val Val Leu Arg Trp Leu Pro Pro Gly Ala Pro Val Ala
                165                 170                 175
Ser Leu Ile Arg Tyr Glu Val Asn Ile Ser Ser Gly Asn Val Ala Gly
                180                 185                 190
Gly Ala Gln Lys Val Glu Ile Leu Asp Gly Arg Thr Glu Cys Ala Leu
            195                 200                 205
Ser Asn Leu Arg Gly Arg Thr Arg Tyr Thr Phe Met Val Arg Ala Arg
    210                 215                 220
Met Ala Glu Pro Ser Phe Gly Gly Phe Trp Ser Ala Trp Ser Glu Pro
225                 230                 235                 240
Ala Ser Leu Leu Thr Ala Ser Asp Leu Asp Pro Leu Ile Leu Thr Leu
                245                 250                 255
Ser Leu Ile Leu Val Leu Ile Leu Leu Leu Ala Val Leu Ala Leu
                260                 265                 270
Leu Ser His Arg Arg Thr Leu Lys Gln Lys Ile Trp Pro Gly Ile Pro
        275                 280                 285
Ser Pro Glu Ser Glu Phe Glu Gly Leu Phe Thr Thr His Lys Gly Asn
    290                 295                 300
Phe Gln Leu Trp Leu Tyr Gln Asn Glu Gly Cys Leu Trp Trp Ser Pro
305                 310                 315                 320
Cys Ala Pro Phe Ala Glu Asp Pro Pro Ser Pro Leu Glu Val Leu Ser
                325                 330                 335
Glu Arg Cys Trp Gly Ala Thr Gln Ala Ala Glu Pro Gly Ala Glu Glu
            340                 345                 350
Gly Pro Leu Leu Glu Pro Leu Gly Ser Glu His Thr Gln Asp Thr Tyr
        355                 360                 365
Leu Val Leu Asp Lys Trp Leu Leu Pro Arg Asn Pro Pro Ser Glu Asp
    370                 375                 380
Leu Pro Arg Pro Asp Gly Ser Leu Asp Met Val Ala Met His Lys Gly
385                 390                 395                 400
Ser Glu Ala Ser Ser Cys Ser Ser Ala Leu Ser Leu Lys Pro Gly Pro
                405                 410                 415
Glu Gly Ala Leu Gly Ala Ser Phe Glu Tyr Thr Ile Leu Asp Pro Ser
                420                 425                 430
```

```
Ser Gln Leu Leu Arg Pro Arg Ala Leu Pro Pro Glu Leu Pro Pro Thr
    435                 440                 445

Pro Pro His Ile Lys Tyr Leu Tyr Leu Met Val Ser Asp Ser Gly Ile
    450                 455                 460

Ser Thr Asp Tyr Ser Ser Gly Gly Ser Gln Glu Ala Gln Gly Asp Ser
465             470                 475                 480

Ser Thr Gly Pro Tyr Leu Asn Pro Tyr Glu Asn Ser Leu Ile Pro Ala
                485                 490                 495

Thr Glu Thr Ser Pro Pro Ser Tyr Val Ala Cys Ser
            500             505
```

ERYTHROPOIETIN AND ANALOGS FOR VETERINARY USE

CROSS-REFERENCE TO RELATED APPLICATIONS

This application is a national stage entry of International Application No. PCT/US2018/036133, filed Jun. 5, 2018, which claims the benefit of priority to US Provisional Application Nos. 62/516,092, filed Jun. 6, 2017; 62/516,642, filed Jun. 7, 2017; and 62/559,104, filed Sep. 15, 2017, each of which is incorporated by reference herein in its entirety for any purpose.

FIELD

This present disclosure relates to erythropoietin (EPO) polypeptide analogs having enhanced pharmacokinetics and methods of producing and using the same, for example, for treating anemia in companion animals, such as canines, felines, and equines. The present disclosure also relates to EPO polypeptides having a mutation in the second binding site and methods of using the same, for example, for treating over production of EPO in a mammal, including humans and companion animals. The present disclosure relates to nucleic acids, vectors, and expression systems encoding EPO polypeptides and methods of using the same (e.g., gene therapy methods), for example for controlled or induced expression of EPO polypeptides. This present disclosure further relates to formulations for EPO polypeptides, including the EPO polypeptides described herein. The present disclosure also relates to polypeptides comprising an extracellular domain of EPO receptor and methods of using the same, for example, for treating overproduction of EPO in any mammal, including humans and companion animals.

BACKGROUND

Erythropoietin (EPO), also known as hematopoeitin or hemopoietin, is a glycoprotein hormone that can stimulate erythropoiesis (i.e., red blood cell production). EPO is used for treating anemia resulting from chronic kidney disease, inflammatory bowel disease (Crohn's disease and ulcer colitis) and myelodysplasia resulting from chemotherapy and radiation therapy. These human disorders are sometimes treated with a recombinant EPO molecule (e.g., Darbepoetin (Aranesp™ and Epogen™, Amgen) and Dynepo™, Shire).

Companion animals suffer from many diseases that are similar to human diseases, including autoimmune diseases and cancer. While human proteins have been used to treat companion animal diseases, it is understood that proteins having significant human-derived amino acid sequence content can be immunogenic to the treated animals. If a human drug elicits an immune response in a companion animal, it may not be effective. See Mauldin et al., August 2010, 21(4):373-382.

Anemia in cats is currently treated by administering human erythropoietin drugs, such as Epogen™ or Aranesp™. However, it is likely that human EPO drugs could illicit an immunogenic response when administered to cats. In addition, human EPO drugs may not bind companion animal EPO receptor in a manner that provides an equally beneficial therapeutic effect in the companion animal as it does in humans.

There remains an unmet need, therefore, for methods and compounds that can be used to treat anemia (e.g., non-refractory anemia) in companion animals, including cats, dogs, and horses. Ideally, the compounds would bind specifically to EPO receptor and have a half-life in plasma sufficiently long to be practicable for therapy, but would be species specific and not be highly immunogenic. EPO polypeptides, including feline EPO polypeptides, having enhanced pharmacokinetics and methods of administering those EPO polypeptides or nucleic acids encoding those EPO polypeptides for the treatment of anemia in companion animals are described herein.

Overproduction of EPO is also an issue. For example, polycythemia may be caused by overproduction and/or secretion of EPO from a tumor (e.g., a kidney tumor), by non-activating mutations in JAK2, or by a genetically-inherited dysregulation resulting in overproduction of EPO. EPO polypeptides having a mutation in the second binding site and methods of administering those EPO polypeptides or nucleic acids encoding those EPO polypeptides for the treatment of polycythemia in mammals are also described herein. Also, described herein are polypeptides comprising an extracellular domain of feline EPO receptor and methods of administering those polypeptides or nucleic acids encoding those EPOR polypeptides for the treatment of polycythemia in mammals.

SUMMARY

Embodiment 1. An erythropoietin (EPO) polypeptide comprising the amino acid sequence of SEQ ID NO: 2 or SEQ ID NO: 13 except for the presence of at least one N-linked glycosylation site not present in SEQ ID NO: 2 or SEQ ID NO: 13, wherein the N-linked glycosylation site comprises the sequence asparagine-xaa-serine or asparagine-xaa-threonine, wherein xaa is any amino acid except proline, and wherein one N-linked glycosylation site does not overlap with another N-linked glycosylation site.

Embodiment 2. The EPO polypeptide of embodiment 1, wherein each of the at least one N-linked glycosylation site is present at:
  a) a position selected from position 47-49, 55-57, 56-58, 60-62, 61-63, 79-81, 82-84, 91-93, 92-94, 97-99, 98-100, 99-101, 112-114, 113-115, 114-116, 115-117, 116-118, 137-139, 140-142, 141-143, 142-144, 143-145, 144-146, 145-147, 146-148, 147-149, 148-150, 149-151, 150-152, 161-163, 162-164, 184-186, and 186-188 of SEQ ID NO: 2; or
  b) a position selected from position 21-23, 29-31, 30-32, 34-36, 35-37, 53-55, 56-58, 65-67, 66-68, 71-73, 72-74, 73-75, 86-88, 87-89, 88-90, 89-91, 90-92, 111-113, 114-116, 115-117, 116-118, 117-119, 118-120, 119-121, 120-122, 121-123, 122-124, 123-125, 124-126, 135-137, 136-138, 158-160, and 162-164 of SEQ ID NO: 13.

Embodiment 3. The EPO polypeptide of embodiment 1 or embodiment 2 comprising valine at a position corresponding to position 113 of SEQ ID NO: 4.

Embodiment 4. The EPO polypeptide of any one of embodiments 1 to 4 comprising:
  a) asparagine at a position corresponding to position 47 of SEQ ID NO: 2, any amino acid except proline at a position corresponding to position 48 of SEQ ID NO: 2, and serine or threonine at a position corresponding to position 49 of SEQ ID NO: 2; or
  b) asparagine at a position corresponding to position 21 of SEQ ID NO: 13, any amino acid except proline at a position corresponding to position 22 of SEQ ID NO: 13, and serine or threonine at a position corresponding to position 23 of SEQ ID NO: 13.

Embodiment 5. The EPO polypeptide of any one of embodiments 1 to 5 comprising:
- a) asparagine at a position corresponding to position 55 of SEQ ID NO: 2, any amino acid except proline at a position corresponding to position 56 of SEQ ID NO: 2, and serine or threonine at a position corresponding to position 57 of SEQ ID NO: 2; or
- b) asparagine at a position corresponding to position 29 of SEQ ID NO: 13, any amino acid except proline at a position corresponding to position 30 of SEQ ID NO: 13, and serine or threonine at a position corresponding to position 31 of SEQ ID NO: 13.

Embodiment 6. The EPO polypeptide of any one of embodiments 1 to 5 comprising:
- a) asparagine at a position corresponding to position 56 of SEQ ID NO: 2, any amino acid except proline at a position corresponding to position 57 of SEQ ID NO: 2, and serine or threonine at a position corresponding to position 58 of SEQ ID NO: 2; or
- b) asparagine at a position corresponding to position 30 of SEQ ID NO: 13, any amino acid except proline at a position corresponding to position 31 of SEQ ID NO: 13, and serine or threonine at a position corresponding to position 32 of SEQ ID NO: 13.

Embodiment 7. The EPO polypeptide of any one of embodiments 1 to 6 comprising:
- a) asparagine at a position corresponding to position 60 of SEQ ID NO: 2, any amino acid except proline at a position corresponding to position 61 of SEQ ID NO: 2, and serine or threonine at a position corresponding to position 62 of SEQ ID NO: 2; or
- b) asparagine at a position corresponding to position 34 of SEQ ID NO: 13, any amino acid except proline at a position corresponding to position 35 of SEQ ID NO: 13, and serine or threonine at a position corresponding to position 36 of SEQ ID NO: 13.

Embodiment 8. The EPO polypeptide of any one of embodiments 1 to 7 comprising:
- a) asparagine at a position corresponding to position 61 of SEQ ID NO: 2, any amino acid except proline at a position corresponding to position 62 of SEQ ID NO: 2, and serine or threonine at a position corresponding to position 63 of SEQ ID NO: 2; or
- b) asparagine at a position corresponding to position 35 of SEQ ID NO: 13, any amino acid except proline at a position corresponding to position 36 of SEQ ID NO: 13, and serine or threonine at a position corresponding to position 37 of SEQ ID NO: 13.

Embodiment 9. The EPO polypeptide of any one of embodiments 1 to 8 comprising:
- a) asparagine at a position corresponding to position 79 of SEQ ID NO: 2, any amino acid except proline at a position corresponding to position 80 of SEQ ID NO: 2, and serine or threonine at a position corresponding to position 81 of SEQ ID NO: 2; or
- b) asparagine at a position corresponding to position 53 of SEQ ID NO: 13, any amino acid except proline at a position corresponding to position 54 of SEQ ID NO: 13, and serine or threonine at a position corresponding to position 55 of SEQ ID NO: 13.

Embodiment 10. The EPO polypeptide of any one of embodiments 1 to 9 comprising:
- a) asparagine at a position corresponding to position 82 of SEQ ID NO: 2, any amino acid except proline at a position corresponding to position 83 of SEQ ID NO: 2, and serine or threonine at a position corresponding to position 84 of SEQ ID NO: 2; or
- b) asparagine at a position corresponding to position 56 of SEQ ID NO: 13, any amino acid except proline at a position corresponding to position 57 of SEQ ID NO: 13, and serine or threonine at a position corresponding to position 58 of SEQ ID NO: 13.

Embodiment 11. The EPO polypeptide of any one of embodiments 1 to 10 comprising:
- a) asparagine at a position corresponding to position 91 of SEQ ID NO: 2, any amino acid except proline at a position corresponding to position 92 of SEQ ID NO: 2, and serine or threonine at a position corresponding to position 93 of SEQ ID NO: 2; or
- b) asparagine at a position corresponding to position 65 of SEQ ID NO: 13, any amino acid except proline at a position corresponding to position 66 of SEQ ID NO: 13, and serine or threonine at a position corresponding to position 67 of SEQ ID NO: 13.

Embodiment 12. The EPO polypeptide of any one of embodiments 1 to 11 comprising:
- a) asparagine at a position corresponding to position 92 of SEQ ID NO: 2, any amino acid except proline at a position corresponding to position 93 of SEQ ID NO: 2, and serine or threonine at a position corresponding to position 94 of SEQ ID NO: 2; or
- b) asparagine at a position corresponding to position 66 of SEQ ID NO: 13, any amino acid except proline at a position corresponding to position 67 of SEQ ID NO: 13, and serine or threonine at a position corresponding to position 68 of SEQ ID NO: 13.

Embodiment 13. The EPO polypeptide of any one of embodiments 1 to 12 comprising:
- a) asparagine at a position corresponding to position 97 of SEQ ID NO: 2, any amino acid except proline at a position corresponding to position 98 of SEQ ID NO: 2, and serine or threonine at a position corresponding to position 99 of SEQ ID NO: 2; or
- b) asparagine at a position corresponding to position 71 of SEQ ID NO: 13, any amino acid except proline at a position corresponding to position 92 of SEQ ID NO: 13, and serine or threonine at a position corresponding to position 73 of SEQ ID NO: 13.

Embodiment 14. The EPO polypeptide of any one of embodiments 1 to 13 comprising:
- a) asparagine at a position corresponding to position 98 of SEQ ID NO: 2, any amino acid except proline at a position corresponding to position 99 of SEQ ID NO: 2, and serine or threonine at a position corresponding to position 100 of SEQ ID NO: 2; or
- b) asparagine at a position corresponding to position 72 of SEQ ID NO: 13, any amino acid except proline at a position corresponding to position 73 of SEQ ID NO: 13, and serine or threonine at a position corresponding to position 74 of SEQ ID NO: 13.

Embodiment 15. The EPO polypeptide of any one of embodiments 1 to 14 comprising:
- a) asparagine at a position corresponding to position 99 of SEQ ID NO: 2, any amino acid except proline at a position corresponding to position 100 of SEQ ID NO: 2, and serine or threonine at a position corresponding to position 101 of SEQ ID NO: 2; or
- b) asparagine at a position corresponding to position 73 of SEQ ID NO: 13, any amino acid except proline at a position corresponding to position 74 of SEQ ID NO: 13, and serine or threonine at a position corresponding to position 75 of SEQ ID NO: 13.

Embodiment 16. The EPO polypeptide of any one of embodiments 1 to 15 comprising:
   a) asparagine at a position corresponding to position 112 of SEQ ID NO: 2, any amino acid except proline at a position corresponding to position 113 of SEQ ID NO: 2, and serine or threonine at a position corresponding to position 114 of SEQ ID NO: 2; or
   b) asparagine at a position corresponding to position 86 of SEQ ID NO: 13, any amino acid except proline at a position corresponding to position 87 of SEQ ID NO: 13, and serine or threonine at a position corresponding to position 88 of SEQ ID NO: 13.

Embodiment 17. The EPO polypeptide of any one of embodiments 1 to 16 comprising:
   a) asparagine at a position corresponding to position 113 of SEQ ID NO: 2, any amino acid except proline at a position corresponding to position 114 of SEQ ID NO: 2, and serine or threonine at a position corresponding to position 115 of SEQ ID NO: 2; or
   b) asparagine at a position corresponding to position 87 of SEQ ID NO: 13, any amino acid except proline at a position corresponding to position 88 of SEQ ID NO: 13, and serine or threonine at a position corresponding to position 89 of SEQ ID NO: 13.

Embodiment 18. The EPO polypeptide of any one of embodiments 1 to 17 comprising:
   a) asparagine at a position corresponding to position 114 of SEQ ID NO: 2, any amino acid except proline at a position corresponding to position 115 of SEQ ID NO: 2, and serine or threonine at a position corresponding to position 116 of SEQ ID NO: 2; or
   b) asparagine at a position corresponding to position 88 of SEQ ID NO: 13, any amino acid except proline at a position corresponding to position 89 of SEQ ID NO: 13, and serine or threonine at a position corresponding to position 90 of SEQ ID NO: 13.

Embodiment 19. The EPO polypeptide of any one of embodiments 1 to 18 comprising:
   a) asparagine at a position corresponding to position 115 of SEQ ID NO: 2, any amino acid except proline at a position corresponding to position 116 of SEQ ID NO: 2, and serine or threonine at a position corresponding to position 117 of SEQ ID NO: 2; or
   b) asparagine at a position corresponding to position 89 of SEQ ID NO: 13, any amino acid except proline at a position corresponding to position 90 of SEQ ID NO: 13, and serine or threonine at a position corresponding to position 91 of SEQ ID NO: 13.

Embodiment 20. The EPO polypeptide of any one of embodiments 1 to 19 comprising:
   a) asparagine at a position corresponding to position 115 of SEQ ID NO: 2, any amino acid except proline at a position corresponding to position 116 of SEQ ID NO: 2, and serine or threonine at a position corresponding to position 117 of SEQ ID NO: 2; or
   b) asparagine at a position corresponding to position 89 of SEQ ID NO: 13, any amino acid except proline at a position corresponding to position 90 of SEQ ID NO: 13, and serine or threonine at a position corresponding to position 91 of SEQ ID NO: 13.

Embodiment 21. The EPO polypeptide of any one of embodiments 1 to 20 comprising:
   a) asparagine at a position corresponding to position 116 of SEQ ID NO: 2, any amino acid except proline at a position corresponding to position 117 of SEQ ID NO: 2, and serine or threonine at a position corresponding to position 118 of SEQ ID NO: 2; or
   b) asparagine at a position corresponding to position 90 of SEQ ID NO: 13, any amino acid except proline at a position corresponding to position 91 of SEQ ID NO: 13, and serine or threonine at a position corresponding to position 92 of SEQ ID NO: 13.

Embodiment 22. The EPO polypeptide of any one of embodiments 1 to 21 comprising:
   a) asparagine at a position corresponding to position 137 of SEQ ID NO: 2, any amino acid except proline at a position corresponding to position 138 of SEQ ID NO: 2, and serine or threonine at a position corresponding to position 139 of SEQ ID NO: 2; or
   b) asparagine at a position corresponding to position 111 of SEQ ID NO: 13, any amino acid except proline at a position corresponding to position 112 of SEQ ID NO: 13, and serine or threonine at a position corresponding to position 113 of SEQ ID NO: 13.

Embodiment 23. The EPO polypeptide of any one of embodiments 1 to 22 comprising:
   a) asparagine at a position corresponding to position 140 of SEQ ID NO: 2, any amino acid except proline at a position corresponding to position 141 of SEQ ID NO: 2, and serine or threonine at a position corresponding to position 142 of SEQ ID NO: 2; or
   b) asparagine at a position corresponding to position 114 of SEQ ID NO: 13, any amino acid except proline at a position corresponding to position 115 of SEQ ID NO: 13, and serine or threonine at a position corresponding to position 116 of SEQ ID NO: 13.

Embodiment 24. The EPO polypeptide of any one of embodiments 1 to 23 comprising:
   a) asparagine at a position corresponding to position 141 of SEQ ID NO: 2, any amino acid except proline at a position corresponding to position 142 of SEQ ID NO: 2, and serine or threonine at a position corresponding to position 143 of SEQ ID NO: 2; or
   b) asparagine at a position corresponding to position 115 of SEQ ID NO: 13, any amino acid except proline at a position corresponding to position 116 of SEQ ID NO: 13, and serine or threonine at a position corresponding to position 117 of SEQ ID NO: 13.

Embodiment 25. The EPO polypeptide of any one of embodiments 1 to 24 comprising:
   a) asparagine at a position corresponding to position 142 of SEQ ID NO: 2, any amino acid except proline at a position corresponding to position 143 of SEQ ID NO: 2, and serine or threonine at a position corresponding to position 144 of SEQ ID NO: 2; or
   b) asparagine at a position corresponding to position 116 of SEQ ID NO: 13, any amino acid except proline at a position corresponding to position 117 of SEQ ID NO: 13, and serine or threonine at a position corresponding to position 118 of SEQ ID NO: 13.

Embodiment 26. The EPO polypeptide of any one of embodiments 1 to 25 comprising:
   a) asparagine at a position corresponding to position 143 of SEQ ID NO: 2, any amino acid except proline at a position corresponding to position 144 of SEQ ID NO: 2, and serine or threonine at a position corresponding to position 145 of SEQ ID NO: 2; or
   b) asparagine at a position corresponding to position 117 of SEQ ID NO: 13, any amino acid except proline at a position corresponding to position 118 of SEQ ID NO: 13, and serine or threonine at a position corresponding to position 119 of SEQ ID NO: 13.

Embodiment 27. The EPO polypeptide of any one of embodiments 1 to 26 comprising:
   a) asparagine at a position corresponding to position 144 of SEQ ID NO: 2, any amino acid except proline at a position corresponding to position 145 of SEQ ID NO: 2, and serine or threonine at a position corresponding to position 146 of SEQ ID NO: 2; or
b) asparagine at a position corresponding to position 118 of SEQ ID NO: 13, any amino acid except proline at a position corresponding to position 119 of SEQ ID NO: 13, and serine or threonine at a position corresponding to position 120 of SEQ ID NO: 13.

Embodiment 28. The EPO polypeptide of any one of embodiments 1 to 27 comprising:
a) asparagine at a position corresponding to position 145 of SEQ ID NO: 2, any amino acid except proline at a position corresponding to position 146 of SEQ ID NO: 2, and serine or threonine at a position corresponding to position 147 of SEQ ID NO: 2; or
b) asparagine at a position corresponding to position 119 of SEQ ID NO: 13, any amino acid except proline at a position corresponding to position 120 of SEQ ID NO: 13, and serine or threonine at a position corresponding to position 121 of SEQ ID NO: 13.

Embodiment 29. The EPO polypeptide of any one of embodiments 1 to 28 comprising:
a) asparagine at a position corresponding to position 146 of SEQ ID NO: 2, any amino acid except proline at a position corresponding to position 147 of SEQ ID NO: 2, and serine or threonine at a position corresponding to position 148 of SEQ ID NO: 2; or
b) asparagine at a position corresponding to position 120 of SEQ ID NO: 13, any amino acid except proline at a position corresponding to position 121 of SEQ ID NO: 13, and serine or threonine at a position corresponding to position 122 of SEQ ID NO: 13.

Embodiment 30. The EPO polypeptide of any one of embodiments 1 to 29 comprising:
a) asparagine at a position corresponding to position 147 of SEQ ID NO: 2, any amino acid except proline at a position corresponding to position 148 of SEQ ID NO: 2, and serine or threonine at a position corresponding to position 149 of SEQ ID NO: 2; or
b) asparagine at a position corresponding to position 121 of SEQ ID NO: 13, any amino acid except proline at a position corresponding to position 122 of SEQ ID NO: 13, and serine or threonine at a position corresponding to position 123 of SEQ ID NO: 13.

Embodiment 31. The EPO polypeptide of any one of embodiments 1 to 30 comprising:
a) asparagine at a position corresponding to position 148 of SEQ ID NO: 2, any amino acid except proline at a position corresponding to position 149 of SEQ ID NO: 2, and serine or threonine at a position corresponding to position 150 of SEQ ID NO: 2; or
b) asparagine at a position corresponding to position 122 of SEQ ID NO: 13, any amino acid except proline at a position corresponding to position 123 of SEQ ID NO: 13, and serine or threonine at a position corresponding to position 124 of SEQ ID NO: 13.

Embodiment 32. The EPO polypeptide of any one of embodiments 1 to 31 comprising:
a) asparagine at a position corresponding to position 149 of SEQ ID NO: 2, any amino acid except proline at a position corresponding to position 150 of SEQ ID NO: 2, and serine or threonine at a position corresponding to position 151 of SEQ ID NO: 2; or
b) asparagine at a position corresponding to position 123 of SEQ ID NO: 13, any amino acid except proline at a position corresponding to position 124 of SEQ ID NO: 13, and serine or threonine at a position corresponding to position 125 of SEQ ID NO: 13.

Embodiment 33. The EPO polypeptide of any one of embodiments 1 to 32 comprising:
a) asparagine at a position corresponding to position 150 of SEQ ID NO: 2, any amino acid except proline at a position corresponding to position 151 of SEQ ID NO: 2, and serine or threonine at a position corresponding to position 152 of SEQ ID NO: 2; or
b) asparagine at a position corresponding to position 124 of SEQ ID NO: 13, any amino acid except proline at a position corresponding to position 125 of SEQ ID NO: 13, and serine or threonine at a position corresponding to position 126 of SEQ ID NO: 13.

Embodiment 34. The EPO polypeptide of any one of embodiments 1 to 33 comprising:
a) asparagine at a position corresponding to position 161 of SEQ ID NO: 2, any amino acid except proline at a position corresponding to position 162 of SEQ ID NO: 2, and serine or threonine at a position corresponding to position 163 of SEQ ID NO: 2; or
b) asparagine at a position corresponding to position 135 of SEQ ID NO: 13, any amino acid except proline at a position corresponding to position 136 of SEQ ID NO: 13, and serine or threonine at a position corresponding to position 137 of SEQ ID NO: 13.

Embodiment 35. The EPO polypeptide of any one of embodiments 1 to 34 comprising:
a) asparagine at a position corresponding to position 162 of SEQ ID NO: 2, any amino acid except proline at a position corresponding to position 163 of SEQ ID NO: 2, and serine or threonine at a position corresponding to position 164 of SEQ ID NO: 2; or
b) asparagine at a position corresponding to position 136 of SEQ ID NO: 13, any amino acid except proline at a position corresponding to position 137 of SEQ ID NO: 13, and serine or threonine at a position corresponding to position 138 of SEQ ID NO: 13.

Embodiment 36. The EPO polypeptide of any one of embodiments 1 to 35 comprising:
a) asparagine at a position corresponding to position 162 of SEQ ID NO: 2, any amino acid except proline at a position corresponding to position 163 of SEQ ID NO: 2, and serine or threonine at a position corresponding to position 164 of SEQ ID NO: 2; or
b) asparagine at a position corresponding to position 136 of SEQ ID NO: 13, any amino acid except proline at a position corresponding to position 137 of SEQ ID NO: 13, and serine or threonine at a position corresponding to position 138 of SEQ ID NO: 13.

Embodiment 37. The EPO polypeptide of any one of embodiments 1 to 36 comprising:
a) asparagine at a position corresponding to position 184 of SEQ ID NO: 2, any amino acid except proline at a position corresponding to position 185 of SEQ ID NO: 2, and serine or threonine at a position corresponding to position 186 of SEQ ID NO: 2; or
b) asparagine at a position corresponding to position 158 of SEQ ID NO: 13, any amino acid except proline at a position corresponding to position 159 of SEQ ID NO: 13, and serine or threonine at a position corresponding to position 160 of SEQ ID NO: 13.

Embodiment 38. The EPO polypeptide of any one of embodiments 1 to 37 comprising:
a) asparagine at a position corresponding to position 186 of SEQ ID NO: 2, any amino acid except proline at a position corresponding to position 187 of SEQ ID NO:

2, and serine or threonine at a position corresponding to position 188 of SEQ ID NO: 2; or b) asparagine at a position corresponding to position 162 of SEQ ID NO: 13, any amino acid except proline at a position corresponding to position 163 of SEQ ID NO: 13, and serine or threonine at a position corresponding to position 164 of SEQ ID NO: 13.

Embodiment 39. The EPO polypeptide of any one of embodiments 1 to 38 comprising the amino acid sequence of SEQ ID NO: 4.

Embodiment 40. The EPO polypeptide of any one of embodiments 1 to 39, wherein the N-linked glycosylation site comprises an amino acid derivative.

Embodiment 41. The EPO polypeptide of embodiment 40, wherein the amino acid derivative is an asparagine derivative, a serine derivative, or a threonine derivative.

Embodiment 42. The EPO polypeptide of any one of embodiments 1 to 41, wherein the EPO polypeptide is glycosylated.

Embodiment 43. The EPO polypeptide of any one of embodiments 1 to 42 comprising at least one glycan moiety attached to the N-linked glycosylation site.

Embodiment 44. The EPO polypeptide of any one of embodiments 1 to 43, wherein the EPO polypeptide is PEGylated.

Embodiment 45. The EPO polypeptide of any one of embodiments 1 to 44, wherein the EPO polypeptide is PEGylated at a glycan.

Embodiment 46. The EPO polypeptide of any one of embodiments 1 to 45, wherein the EPO polypeptide is PEGylated at a primary amine.

Embodiment 47. The EPO polypeptide of any one of embodiments 1 to 46, wherein the EPO polypeptide is PEGylated at the N-terminal alpha-amine.

Embodiment 48. A composition comprising a plurality of EPO polypeptides of any one of embodiments 1 to 47 having a range of isoelectric points of from about 1 to about 3.5, of from about 1.5 to about 3.5, of from about 2 to about 3.5, of from about 2.5 to about 3.5, of from about 3 to about 3.5, of about 3.5 or less, or of about 3 or less, as determined by isoelectric focusing.

Embodiment 49. A composition comprising a plurality of EPO polypeptides of any one of embodiments 1 to 47 having a range of isoelectric points of from about 3.5 to about 6, of from about 4 to about 6, of from about 4.5 to about 6, of from about 5 to about 6, of from about 5.5 to about 6, of from about 3.5 to about 5, of from about 4 to about 5, of from about 4.5 to about 5, of about 3.5 or greater, of about 4 or greater, or of about 4.5 or greater, as determined by isoelectric focusing.

Embodiment 50. A combination comprising the composition of embodiment 48 and the composition of embodiment 49.

Embodiment 51. An isolated nucleic acid encoding the EPO polypeptide of any one of embodiments 1 to 41.

Embodiment 52. The nucleic acid of embodiment 51, wherein the nucleic acid comprises a regulatory sequence.

Embodiment 53. The nucleic acid of embodiment 52, wherein the regulatory sequence is a constitutive promoter; an inducible regulatory sequence, such as a tetracycline response element or a hypoxia-inducible promoter; a tissue specific promoter; an enhancer; a silencer; or encodes a micro RNA or transcription factor.

Embodiment 54. An isolated nucleic acid encoding an EPO polypeptide comprising the amino acid sequence of SEQ ID NO: 2 or SEQ ID NO: 13; and a heterologous regulatory sequence, wherein the heterologous regulatory sequence is not a constitutive promoter.

Embodiment 55. The nucleic acid of embodiment 54, wherein the heterologous regulatory sequence is an inducible regulatory sequence, such as a tetracycline response element or a hypoxia-inducible promoter; a tissue specific promoter; an enhancer; a silencer; or encodes a micro RNA or transcription factor.

Embodiment 56. A vector comprising the nucleic acid of any one of embodiments 51 to 55.

Embodiment 57. The vector of embodiment 56, wherein the vector is a viral vector or a bacterial vector.

Embodiment 58. The vector of embodiment 56 or embodiment 57, wherein the vector is a retroviral vector, a herpesviral vector, an adenoviral vector, an adeno-associated viral vector, or a pox viral vector.

Embodiment 59. An expression system comprising a first vector comprising a nucleic acid encoding the EPO polypeptide of any one of embodiment 1 to 41; and a second vector comprising a regulatory sequence.

Embodiment 60. An expression system comprising a first vector comprising a nucleic acid encoding an EPO polypeptide comprising the amino acid sequence of SEQ ID NO: 2 or SEQ ID NO: 13; and a second vector comprising a regulatory sequence.

Embodiment 61. The expression system of embodiment 59 or embodiment 60, wherein the regulatory sequence encodes a micro RNA or transcription factor.

Embodiment 62. The expression system of embodiment 60 or embodiment 61, wherein the first vector and/or second vector is a viral vector or a bacterial vector.

Embodiment 63. The expression system of any one of embodiments 60 to 62, wherein the first vector and/or second vector is a retroviral vector, a herpesviral vector, an adenoviral vector, an adeno-associated viral vector, or a pox viral vector.

Embodiment 64. A host cell comprising the nucleic acid of any one of embodiments 51 to 55, the vector of any one of embodiments 56 to 58, or the expression system of any one of embodiments 59 to 63.

Embodiment 65. A method of producing a composition comprising EPO polypeptides comprising culturing the host cell of embodiment 64 and isolating the EPO polypeptides.

Embodiment 66. The method of embodiment 65, wherein the EPO polypeptides are isolated by column chromatography.

Embodiment 67. The method of embodiment 65 or embodiment 66, wherein the EPO polypeptides are isolated by ion exchange column chromatography.

Embodiment 68. The method of any one of embodiments 65 to 67, wherein the EPO polypeptides are isolated by Capto Butyl column chromatography, cation-exchange column chromatography, or anion-exchange column chromatography.

Embodiment 69. The method of any one of embodiments 65 to 68, wherein the EPO polypeptides are isolated by mixed-mode column chromatography.

Embodiment 70. The method of any one of embodiment 65 to 69, wherein the EPO polypeptides are isolated by hydrophobic interaction column chromatography.

Embodiment 71. The method of any one of embodiments 65 to 70, wherein the EPO polypeptides are isolated by a combination of chromatography columns.

Embodiment 72. The method of any one of embodiments 65 to 71, wherein the method further comprises inactivating and/or removing viruses.

Embodiment 73. The method of any one of embodiments 65 to 72, wherein the EPO polypeptides have a range of isoelectric points of from about 1 to about 3.5, of from about 1.5 to about 3.5, of from about 2 to about 3.5, of from about 2.5 to about 3.5, of from about 3 to about 3.5, of about 3.5 or less, or of about 3 or less, as determined by isoelectric focusing.

Embodiment 74. The method of any one of embodiments 65 to 72, wherein the EPO polypeptides have a range of isoelectric points of from about 3.5 to about 6, of from about 4 to about 6, of from about 4.5 to about 6, of from about 5 to about 6, of from about 5.5 to about 6, of from about 3.5 to about 5, of from about 4 to about 5, of from about 4.5 to about 5, of about 3.5 or greater, of about 4 or greater, or of about 4.5 or greater, as determined by isoelectric focusing.

Embodiment 75. A pharmaceutical composition comprising the EPO polypeptide of any one of embodiments 1 to 47, the composition of embodiments 48 or 49, the combination of embodiment 50, the nucleic acid of any one of embodiments 51 to 55, the vector of any one of embodiments 56 to 58, or the expression system of any one of embodiments 59 to 63; and a pharmaceutically acceptable carrier.

Embodiment 76. A pharmaceutical composition comprising an EPO polypeptide and a pharmaceutically acceptable carrier, wherein the pharmaceutically acceptable carrier comprises a) sodium phosphate, sodium chloride, and polysorbate 80; b) sodium phosphate, sodium chloride, and polysorbate 20; c) sodium citrate, sodium chloride, and polysorbate 80; or d) sodium citrate, sodium chloride, and polysorbate 20.

Embodiment 77. A pharmaceutical composition comprising an EPO polypeptide and a pharmaceutically acceptable carrier, wherein the pharmaceutically acceptable carrier comprises sodium citrate, sodium chloride, polysorbate 80, and m-cresol.

Embodiment 78. A pharmaceutical composition comprising an EPO polypeptide and a pharmaceutically acceptable carrier, wherein the pharmaceutically acceptable carrier comprises sodium phosphate, sodium chloride, polysorbate 20, and benzyl alcohol.

Embodiment 79. The pharmaceutical composition of any one of embodiments 76 to 78, wherein the concentration of sodium chloride is about 140 mM.

Embodiment 80. The pharmaceutical composition of any one of embodiments 76 to 79, wherein the concentration of sodium phosphate or sodium citrate is about 20 mM.

Embodiment 81. The pharmaceutical composition of any one of embodiments 76 to 80, wherein the concentration of polysorbate 20 or polysorbate 80 is about 650 nM.

Embodiment 82. The pharmaceutical composition of any one of embodiments 77, or 79 to 81, wherein the concentration of m-cresol is about 0.2%.

Embodiment 83. The pharmaceutical composition of any one of embodiments 78 to 82, wherein the concentration of benzyl alcohol is about 1%.

Embodiment 84. The pharmaceutical composition of any one of embodiments 76 to 83, wherein the pharmaceutically acceptable carrier comprises
a) sodium phosphate at a concentration of about 20 mM, sodium chloride at a concentration of about 140 mM, polysorbate 80 at a concentration of about 650 nM or
b) sodium phosphate at a concentration of about 20 mM, sodium chloride at a concentration of about 140 mM, polysorbate 20 at a concentration of about 650 nM.

Embodiment 85. The pharmaceutical composition of any one of embodiments 76 to 84, wherein the pharmaceutically acceptable carrier comprises sodium citrate at a concentration of about 20 mM, sodium chloride at a concentration of about 140 nM, polysorbate 80 at a concentration of about 650 nM, and m-cresol at a concentration of about 0.2%.

Embodiment 86. The pharmaceutical composition of any one of embodiments 76 to 85, wherein the pharmaceutically acceptable carrier comprises sodium phosphate at a concentration of about 20 mM, sodium chloride at a concentration of about 140 nM, polysorbate 20 at a concentration of about 650 nM, and benzyl alcohol at a concentration of about 1%.

Embodiment 87. The pharmaceutical composition of any one of embodiments 76 to 86, wherein the EPO polypeptide is the EPO polypeptide of any one of embodiments 1 to 47, the composition of embodiment 48 or embodiment 49, or the combination of embodiment 50.

Embodiment 88. A method of delivering an EPO polypeptide to a companion animal species comprising administering the EPO polypeptide of any one of embodiments 1 to 47, the composition of embodiments 48 or 49, the combination of embodiment 50, or the pharmaceutical composition of embodiment 75 or embodiment 87 parenterally.

Embodiment 89. A method of delivering an EPO polypeptide to a companion animal species comprising administering the EPO polypeptide of any one of embodiments 1 to 47, the composition of embodiments 48 or 49, the combination of embodiment 50, or the pharmaceutical composition of embodiment 75 or embodiment 87 by an intramuscular route, an intraperitoneal route, an intracerebrospinal route, a subcutaneous route, an intra-arterial route, an intrasynovial route, an intrathecal route, or an inhalation route.

Embodiment 90. A method of delivering an isolated nucleic acid encoding an EPO polypeptide to a companion animal species comprising administering the nucleic acid of any one of embodiments 51 to 55, the vector of any one of embodiments 56 to 58, or the expression system of any one of embodiments 59 to 63 parenterally.

Embodiment 91. A method of treating a companion animal species having anemia, the method comprising administering to the companion animal species a therapeutically effective amount of the EPO polypeptide of any one of embodiments 1 to 47, the composition of embodiments 48 or 49, the combination of embodiment 50, or the pharmaceutical composition of embodiment 75 or embodiment 87.

Embodiment 92. A method of treating a companion animal species having anemia, the method comprising administering to the companion animal species a therapeutically effective amount of the nucleic acid of any one of embodiments 51 to 55, the vector of any one of embodiments 56 to 58, or the expression system of any one of embodiments 59 to 63.

Embodiment 93. The method of embodiment 91 or embodiment 92, wherein the EPO polypeptide, composition, nucleic acid, vector, expression system, or pharmaceutical composition is administered parenterally.

Embodiment 94. The method of any one of embodiments 91 to 93, wherein the EPO polypeptide, composition, nucleic acid, vector, expression system, or pharmaceutical composition is administered by an intramuscular route, an intraperitoneal route, an intracerebrospinal route, a subcutaneous route, an intra-arterial route, an intrasynovial route, an intrathecal route, or an inhalation route.

Embodiment 95. The method of any one of embodiments 88 to 94, wherein the companion animal species is feline, canine, or equine.

Embodiment 96. The method of any one of embodiments 91 to 95, wherein the anemia is caused by chronic kidney disease, inflammatory bowel disease, or myelodysplasia.

Embodiment 97. The method of any one of embodiments 88 to 96, wherein the EPO polypeptide is administered in an amount of from about 1 µg/kg body weight to about 10 µg/kg body weight, or about 1 µg/kg body weight to about 5 µg/kg body weight, or about 1 µg/kg body weight, or about 3 µg/kg body weight, or about 5 µg/kg body weight, or about 10 µg/kg body weight.

Embodiment 98. The method of any one of embodiments 88 to 97, wherein the EPO polypeptide, composition, nucleic acid, vector, expression system, or pharmaceutical composition is administered every 7 to 10 days.

Embodiment 99. The method of any one of embodiments 88 to 98, wherein the method further comprises administering iron dextran.

Embodiment 100. The method of any one of embodiments 88 to 99, wherein the companion animal species has a baseline hematocrit percentage of from about 15% to about 30%, of from about 15% to about 25%, of from about 20% to about 25%, of from about 25% to about 30%, of below about 15%, of below about 18%, of below about 20%, of below about 25%, of below about 29%, or of below about 30% prior to administration of the EPO polypeptide, composition, nucleic acid, vector, expression system, or pharmaceutical composition.

Embodiment 101. The method of any one of embodiments 88 to 100, wherein the hematocrit percentage of the companion animal species increases to at least 25%, or at least 26%, or at least 27%, or at least 28%, or at least 29%, or at least 30%, or at least 32%, or at least 35%, or at least 38%, or at least 40%, or at least 42%, or at least 45%, or at least 48% following administration of the EPO polypeptide, composition, nucleic acid, vector, expression system, or pharmaceutical composition.

Embodiment 102. The method of embodiment 101, wherein the hematocrit percentage of the companion animal species increases to at least 25%, or at least 27%, or at least 30%, or at least 32%, or at least 35% at 1 week, 2 weeks, 3 weeks, 4 weeks, 5 weeks, or 6 weeks after a first administration of the EPO polypeptide, composition, nucleic acid, vector, expression system, or pharmaceutical composition.

Embodiment 103. The method of any one of embodiments 88 to 102, wherein the body weight of the companion animal species is maintained or increased compared to baseline following administration of the EPO polypeptide, composition, nucleic acid, vector, expression system, or pharmaceutical composition.

Embodiment 104. The method of embodiment 103, wherein the body weight of the companion animal species is maintained or increased at 1 week, 2 weeks, 3 weeks, 4 weeks, 5 weeks, or 6 weeks after a first administration of the EPO polypeptide, composition, nucleic acid, vector, expression system, or pharmaceutical composition.

Embodiment 105. The method of any one of embodiments 88 to 104, wherein the level of symmetric dimethylarginine or serum creatine renal biomarker is decreased compared to baseline following administration of the EPO polypeptide, composition, nucleic acid, vector, expression system, or pharmaceutical composition.

Embodiment 106. A method of expressing an EPO polypeptide in a target cell, comprising:
a) transferring a nucleic acid, vector, or expression system into the target cell, wherein the nucleic acid, vector, or expression system comprises:
i) a nucleic acid encoding the EPO polypeptide of any one of embodiments 1 to 41, and
ii) a regulatory sequence; and
b) culturing the cell under conditions supportive for expression of the EPO polypeptide.

Embodiment 107. A method of expressing an EPO polypeptide in a target cell, comprising:
a) transferring a nucleic acid, a vector, or an expression system into the target cell, wherein the nucleic acid, vector, or expression system comprises:
i) a nucleic acid encoding an EPO polypeptide having the amino acid sequence of SEQ ID NO: 2 or an EPO polypeptide having the amino acid sequence of SEQ ID NO: 13, and
ii) a regulatory sequence, wherein the regulatory sequence is not a constitutive promoter; and
b) culturing the cell under conditions supportive for expression of the EPO polypeptide.

Embodiment 108. The method of embodiment 106 or embodiment 107, wherein the regulatory sequence is an inducible regulatory sequence, such as a tetracycline response element or a hypoxia-inducible promoter; a tissue specific promoter; an enhancer; a silencer; or encodes a micro RNA or transcription factor.

Embodiment 109. The method of any one of embodiments 106 to 108, wherein the vector is a viral vector or a bacterial vector.

Embodiment 110. The method of any one of embodiments 106 to 109, wherein the vector is a retroviral vector, a herpesviral vector, an adenoviral vector, an adeno-associated viral vector, or a pox viral vector.

Embodiment 111. The method of any one of embodiments 106 to 110, wherein the cell is a cell of a companion animal species.

Embodiment 112. The method of any one of embodiments 106 to 111, wherein the cell is located in a living companion animal species.

Embodiment 113. The method of embodiment 111 or embodiment 112, wherein the companion animal species is a canine, feline, or equine.

Embodiment 114. An erythropoietin (EPO) polypeptide comprising:
a) at least one amino acid substitution at a position corresponding to a position selected from position 5, 8, 10, 11, 14, 15, 78, 96, 97, 99, 100, 103, 104, 107, 108, or 110 of SEQ ID NO: 13;
b) at least one amino acid substitution of SEQ ID NO: 9 that corresponds to a position selected from position 5, 8, 10, 11, 14, 15, 78, 96, 97, 99, 100, 103, 104, 107, 108, or 110 of SEQ ID NO: 13;
c) at least one amino acid substitution of SEQ ID NO: 10 that corresponds to a position selected from position 5, 8, 10, 11, 14, 15, 78, 96, 97, 99, 100, 103, 104, 107, 108, or 110 of SEQ ID NO: 13;
d) at least one amino acid substitution of SEQ ID NO: 11 that corresponds to position selected from position 5, 8, 10, 11, 14, 15, 78, 96, 97, 99, 100, 103, 104, 107, 108, or 110 of SEQ ID NO: 13; or
e) at least one amino acid substitution of SEQ ID NO: 12 that corresponds to a position selected from position 5, 8, 10, 11, 14, 15, 78, 96, 97, 99, 100, 103, 104, 107, 108, or 110 of SEQ ID NO: 13.

Embodiment 115. The EPO polypeptide of embodiment 114, wherein the at least one amino acid substitution is:
a) a substitution at a position corresponding to position 103 of SEQ ID NO: 13;
b) a substitution of SEQ ID NO: 9 that corresponds to position 103 of SEQ ID NO: 13;
c) a substitution of SEQ ID NO: 10 that corresponds to position 103 of SEQ ID NO: 13;

d) a substitution of SEQ ID NO: 11 that corresponds to position 103 of SEQ ID NO: 13; or e) a substitution of SEQ ID NO: 12 that corresponds to position 103 of SEQ ID NO: 13.

Embodiment 116. The EPO polypeptide of embodiment 114 or 115, wherein an alanine is substituted at a position corresponding to position 103 of SEQ ID NO: 13.

Embodiment 117. The EPO polypeptide of any one of embodiments 114 to 116, wherein the at least one amino acid substitution comprises substitution with an amino acid derivative.

Embodiment 118. The EPO polypeptide of any one of embodiments 114 to 117, wherein the EPO polypeptide comprises an amino acid sequence of SEQ ID NO: 16, SEQ ID NO: 17, SEQ ID NO: 18, or SEQ ID NO: 19.

Embodiment 119. A polypeptide comprising an amino acid sequence of SEQ ID NO: 16, SEQ ID NO: 17, SEQ ID NO: 18, or SEQ ID NO: 19.

Embodiment 120. An isolated nucleic acid encoding the EPO polypeptide of any one of embodiments 114 to 119.

Embodiment 121. A host cell comprising the nucleic acid of embodiment 120.

Embodiment 122. A method of producing a composition comprising EPO polypeptides comprising culturing the host cell of embodiment 121 and isolating the EPO polypeptides.

Embodiment 123. A pharmaceutical composition comprising the EPO polypeptide of any one of embodiments 114 to 119 and a pharmaceutically acceptable carrier.

Embodiment 124. The pharmaceutical composition of any one of embodiments 76 to 86, wherein the EPO polypeptide is the EPO polypeptide of any one of embodiments 114 to 119.

Embodiment 125. A polypeptide comprising an extracellular domain of a feline erythropoietin receptor (EPOR) polypeptide comprising the amino acid sequence of SEQ ID NO: 5, SEQ ID NO: 6, SEQ ID NO: 7, SEQ ID NO: 8, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32; and a heterologous polypeptide sequence.

Embodiment 126. A polypeptide comprising the amino acid sequence of SEQ ID NO: 23, SEQ ID NO: 24, SEQ ID NO: 25, SEQ ID NO: 26, SEQ ID NO: 29, SEQ ID NO: 30, SEQ ID NO: 31, or SEQ ID NO: 32; and a heterologous polypeptide sequence.

Embodiment 127. The polypeptide of embodiment 115 or embodiment 116 comprising the amino acid sequence of SEQ ID NO: 5, SEQ ID NO: 6, SEQ ID NO: 7, SEQ ID NO: 8, or SEQ ID NO: 22.

Embodiment 128. An isolated nucleic acid encoding the polypeptide of any one of embodiments 125 to 127.

Embodiment 129. A host cell comprising the nucleic acid of embodiment 128.

Embodiment 130. A method of producing a polypeptide comprising culturing the host cell of embodiment 129 and isolating the polypeptide.

Embodiment 131. A pharmaceutical composition comprising the polypeptide of any one of embodiments 126 to 127 and a pharmaceutically acceptable carrier.

Embodiment 132. A method of treating a subject having polycythemia, the method comprising administering to the subject a therapeutically effective amount of the EPO polypeptide of any one of embodiments 114 to 119, the polypeptide of any one of embodiments 125 to 127, the nucleic acid of embodiment 120 or embodiment 128, or the pharmaceutical composition of embodiment 123, embodiment 124, or embodiment 131.

Embodiment 133. The method of embodiment 132, wherein the EPO polypeptide, polypeptide, nucleic acid, or pharmaceutical composition is administered parenterally.

Embodiment 134. The method of embodiment 132 or embodiment 133, wherein the EPO polypeptide, the polypeptide, nucleic acid, or pharmaceutical composition is administered by an intramuscular route, an intraperitoneal route, an intracerebrospinal route, a subcutaneous route, an intra-arterial route, an intrasynovial route, an intrathecal route, or an inhalation route.

Embodiment 135. The method of any one of embodiments 132 to 132, wherein the subject is a companion animal species.

Embodiment 136. The method of embodiment 135, wherein the companion animal species is feline, canine, or equine.

Embodiment 137. The method of any one of embodiments 132 to 134, wherein the subject is a human.

Embodiment 138. The method of any one of embodiments 132 to 137, wherein the polycythemia is caused by a mutation in JAK2, overproduction and/or secretion of EPO from a tumor.

These and other aspects and various embodiments are described more fully below.

BRIEF DESCRIPTION OF THE DRAWINGS

FIG. 2A and FIG. 2B show IEF gels to demonstrate separation of various sialylation states. pI marker locations are indicated.

FIG. 4 shows sialic acid analysis as DMB-sialic acid using HPLC with a fluorescence detector.

FIG. 7 is a series of Western blots showing expression of fEPOR201-N-flag, fEPOR202-N-flag, fEPOR201_ECD-Fc, fEPOR202_ECD-Fc, and fEPOR203_ECD-Fc. FIG. 7A is a Western blot using anti-human Fc antibody to identify feline EPOR201-ECD-Fc (lane 1) and feline EPOR202-ECD-Fc (lane 2). FIG. 7B and FIG. 7C are Western blots using anti-flag antibody to identify feline EPOR201-N-flag (lanes 3 and 4) and feline EPOR202-N-flag (lanes 6 and 7) compared to an untransfected control (lane 5). FIG. 7D is a Coomassie stain of an SDS-PAGE of feline EPOR203-ECD-Fc (lane 9) and a molecular weight standard (lane 8).

DESCRIPTION OF CERTAIN SEQUENCES

Figure 1A:
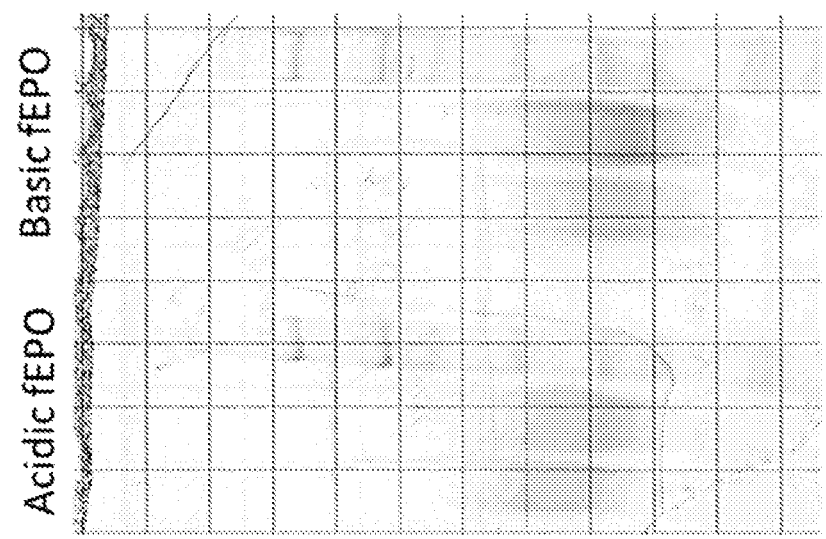
FIG. 1A shows isoelectric focusing (IEF) and FIG. 1B shows SDS-PAGE of isolated basic and acidic Analog 6-30 GV Mature fractions.

Table 1 provides a listing of certain sequences referenced herein.

TABLE 1

Description of Certain Sequences

| SEQ ID NO: | SEQUENCE | DESCRIPTION |
|---|---|---|
| 1 | MGSCECPALLLLLSLLLLPLGLPVLGAPPRLIC DSRVLERYILGAREAENVTMGCAEGCSFSENITV PDTKVNFYTWKRMDVGQQAVEVWQGLALLSE AILRGQALLANSSQPSETLQLHVDKAVSSLRSLTS LLRALGAQKEATSLPEATSAAPLRTFTVDTLCKL FRIYSNFLRGKLTLYTGEACRRGDR | Felis catus Erythropoietin (EPO) precursor form "wild-type feline EPO G44" |
| 2 | MGSCECPALLLLLSLLLLPLGLPVLGAPPRLIC DSRVLERYILEAREAENVTMGCAEGCSFSENITV PDTKVNFYTWKRMDVGQQAVEVWQGLALLSE AILRGQALLANSSQPSETLQLHVDKAVSSLRSLTS LLRALGAQKEATSLPEATSAAPLRTFTVDTLCKL FRIYSNFLRGKLTLYTGEACRRGDR | Felis catus EPO precursor form "wild-type feline EPO E44" |
| 3 | MGSCECPALLLLLSLLLLPLGLPVLGAPPRLIC DSRVLERYILGAREAENVTMGCNETCSFSENITV PDTKVNFYTWKRMDVGQQAVEVWQGLALLSE AILRGQALLANSSQVNETLQLHVDKAVSSLRSLT SLLRALGAQKEATSLPEATSAAPLRTFTVDTLCK LFRIYSNFLRGKLTLYTGEACRRGDR | Feline EPO Analog 6-30 G44V113 precursor form or "Analog 6-30 GV Precursor" |
| 4 | MGSCECPALLLLLSLLLLPLGLPVLGAPPRLIC DSRVLERYILEAREAENVTMGCNETCSFSENITV PDTKVNFYTWKRMDVGQQAVEVWQGLALLSE AILRGQALLANSSQVNETLQLHVDKAVSSLRSLT SLLRALGAQKEATSLPEATSAAPLRTFTVDTLCK LFRIYSNFLRGKLTLYTGEACRRGDR | Feline EPO Analog 6-30 E44V113 precursor form or "Analog 6-30 EV Precursor" |
| 5 | MDHLWAPLWPGVGSLCLLLAGAAW*AMDYKDD DDK*APPPNPLDPKFESKVNMVCMRAPEASACGS SERLEDLVCFWEEAASAGVGPDNYSFFYQLEGEP WKPCSLHQAPTARGAVRFWCSLPTADASSFVPL ELRVTAVSSGAPRYHRIIHINEVVLLDPPAGLLAR RADEGGHVVLRWLPPPGAPVASLIRYEVNISSGN VAGGAQKVEILDGRTECALSNLRGRTRYTFMVR ARMAEPSFGGFWSAWSEPASLLTASDLDPLILTL SLILVLILLLLAVLALLSHRRFTRTLKQKIWPGIPS PESEFEGLFTTHKGNFQLWLYQNEGCLWWSPCA PFAEDPPSPLEVLSERCWGATQAAEPGAEEGPLL EPLGSEHTQDTYLVLDKWLLPRNPPSEDLPRPDG SLDMVAMHKGSEASSCSSALSLKPGPEGALGAS FEYTILDPSSQLLRPRALPPELPPTPPHIKYLYLMV SDSGISTDYSSGGSQEAQGDSSTGPYLNPYENSLI PATETSPPSYVACS | Flag_feline EPOR201 full-length (fEPOR201-N-flag) |
| 6 | MDHLWAPLWPGVGSLCLLLAGAAW*AMDYKDD DDK*APPPNPLDPKFESKGKDGSVCRPPQWFLEGN AEERLEDLVCFWEEAASAGVGPDNYSFFYQLEG EPWKPCSLHQAPTARGAVRFWCSLPTADASSFV PLELRVTAVSSGAPRYHRIIHINEVVLLDPPAGLL ARRADEGGHVVLRWLPPPGAPVASLIRYEVNISS | Flag_feline EPOR202 full-length (fEPOR202-N-flag) |

TABLE 1 -continued

Description of Certain Sequences

| SEQ ID NO: | SEQUENCE | DESCRIPTION |
|---|---|---|
|  | GNVAGGAQKVEILDGRTECALSNLRGRTRYTFM VRARMAEPSFGGFWSAWSEPASLLTASDLDPLIL TLSLILVLILLLLAVLALLSHRRTLKQKIWPGIPSP ESEFEGLFTTHKGNFQLWLYQNEGCLWWSPCAP FAEDPPSPLEVLSERCWGATQAAEPGAEEGPLLE PLGSEHTQDTYLVLDKWLLPRNPPSEDLPRPDGS LDMVAMHKGSEASSCSSALSLKPGPEGALGASF EYTILDPSSQLLRPRALPPELPPTPPHIKYLYLMVS DSGISTDYSSGGSQEAQGDSSTGPYLNPYENSLIP ATETSPPSYVACS |  |
| 7 | MDHLWAPLWPGVGSLCLLLAGAAWAPPPNPLD PKFESKVNMVCMRAPEASACGSSERLEDLVCFW EEAASAGVGPDNYSFFYQLEGEPWKPCSLHQAP TARGAVRFWCSLPTADASSFVPLELRVTAVSSGA PRYHRIIHINEVVLLDPPAGLLARRADEGGHVVL RWLPPPGAPVASLIRYEVNISSGNVAGGAQKVEI LDGRTECALSNLRGRTRYTFMVRARMAEPSFGG FWSAWSEPASLLTASDLD*IEGRMD*PKSCDKTHTC PPCPAPELLGGPSVFLFPPKPKDTLMISRTPEVTC VVVDVSHEDPEVKFNWYVDGVEVHNAKTKPRE EQYNSTYRVVSVLTVLHQDWLNGKEYKCKVSN KALPAPIEKTISKAKGQPREPQVYTLPPSRDELTK NQVSLTCLVKGFYPSDIAVEWESNGQPENNYKT TPPVLDSDGSFFLYSKLTVDKSRWQQGNVFSCSV MHEALHNHYTQKSLSLSPGK | Feline EPOR201_ECD_ human Fc |
| 8 | MDHLWAPLWPGVGSLCLLLAGAAWAPPPNPLD PKFESKGKDGSVCRPPQWFLEGNAEERLEDLVCF WEEEAASAGVGPDNYSFFYQLEGEPWKPCSLHQA PTARGAVRFWCSLPTADASSFVPLELRVTAVSSG APRYHRIIHINEVVLLDPPAGLLARRADEGGHVV LRWLPPPGAPVASLIRYEVNISSGNVAGGAQKVE ILDGRTECALSNLRGRTRYTFMVRARMAEPSFG GFWSAWSEPASLLTASDLD*IEGRMD*PKSCDKTHT CPPCPAPELLGGPSVFLFPPKPKDTLMISRTPEVT CVVVDVSHEDPEVKFNWYVDGVEVHNAKTKPR EEQYNSTYRVVSVLTVLHQDWLNGKEYKCKVS NKALPAPIEKTISKAKGQPREPQVYTLPPSRDELT KNQVSLTCLVKGFYPSDIAVEWESNGQPENNYK TTPPVLDSDGSFFLYSKLTVDKSRWQQGNVFSCS VMHEALHNHYTQKSLSLSPGK | Feline EPOR202_ECD_ human Fc |
| 9 | APPRLICDSRVLERYLLEAKEAENITTGCAEHCSL NENITVPDTKVNFYAWKRMEVGQQAVEVWQGL ALLSEAVLRGQALLVNSSQPWEPLQLHVDKAVS GLRSLTTLLRALGAQKEAISPPDAASAAPLRTITA DTFRKLFRVYSNFLRGKLKLYTGEACRTGDR | Human EPO mature form |
| 10 | APPRLICDSRVLERYILEAREAENVTMGCAQGCS FSENITVPDTKVNFYTWKRMDVGQQALEVWQG LALLSEAILRGQALLANASQPSETPQLHVDKAVS SLRSLTSLLRALGAQKEAMSLPEEASPAPLRTFTV DTLCKLFRIYSNFLRGKLTLYTGEACRRGDR | Canis lupus EPO mature form |
| 11 | APPRLICDSRVLERYILEAREAENVTMGCAEGCS FGENVTVPDTKVNFYSWKRMEVEQQAVEVWQG LALLSEAILQGQALLANSSQPSETLRLHVDKAVS SLRSLTSLLRALGAQKEAISPPDAASAAPLRTFAV DTLCKLFRIYSNFLRGKLKLYTGEACRRGDR | Equus caballus EPO mature form |
| 12 | APPRLICDSRVLERYILGAREAENVTMGCAEGCS FSENITVPDTKVNFYTWKRMDVGQQAVEVWQG LALLSEAILRGQALLANSSQPSETLQLHVDKAVS SLRSLTSLLRALGAQKEATSLPEATSAAPLRTFTV DTLCKLFRIYSNFLRGKLTLYTGEACRRGDR | Felis catus EPO mature form "wild-type feline EPO G18" |
| 13 | APPRLICDSRVLERYILEAREAENVTMGCAEGCS FSENITVPDTKVNFYTWKRMDVGQQAVEVWQG LALLSEAILRGQALLANSSQPSETLQLHVDKAVS SLRSLTSLLRALGAQKEATSLPEATSAAPLRTFTV DTLCKLFRIYSNFLRGKLTLYTGEACRRGDR | Felis catus EPO mature form "wild-type feline EPO E18" |

TABLE 1 -continued

Description of Certain Sequences

| SEQ ID NO: | SEQUENCE | DESCRIPTION |
|---|---|---|
| 14 | APPRLICDSRVLERYILGAREAENVTMGCNETCS FSENITVPDTKVNFYTWKRMDVGQQAVEVWQG LALLSEAILRGQALLANSSQVNETLQLHVDKAVS SLRSLTSLLRALGAQKEATSLPEATSAAPLRTFTV DTLCKLFRIYSNFLRGKLTLYTGEACRRGDR | Feline EPO Analog 6-30 G18V87 mature form or "Analog 6-30 GV Mature" |
| 15 | APPRLICDSRVLERYILEAREAENVTMGCNETCS FSENITVPDTKVNFYTWKRMDVGQQAVEVWQG LALLSEAILRGQALLANSSQVNETLQLHVDKAVS SLRSLTSLLRALGAQKEATSLPEATSAAPLRTFTV DTLCKLFRIYSNFLRGKLTLYTGEACRRGDR | Feline EPO Analog 6-30 E18V87 mature form or "Analog 6-30 EV Mature" |
| 16 | APPRLICDSRVLERYLLEAKEAENITTGCAEHCSL NENITVPDTKVNFYAWKRMEVGQQAVEVWQGL ALLSEAVLRGQALLVNSSQPWEPLQLHVDKAVS GLASLTTLLRALGAQKEAISPPDAASAAPLRTITA DTFRKLFRVYSNFLRGKLKLYTGEACRTGDR | Human erythropoietin second site mutation R103A |
| 17 | APPRLICDSRVLERYILEAREAENVTMGCAEGCS FSENITVPDTKVNFYTWKRMDVGQQAVEVWQG LALLSEAILRGQALLANSSQPSETLQLHVDKAVS SLASLTSLLRALGAQKEATSLPEATSAAPLRTFTV DTLCKLFRIYSNFLRGKLTLYTGEACRRGDR | Felis catus Enthropoictin second site mutation R103A |
| 18 | APPRLICDSRVLERYILEAREAENVTMGCAQGCS FSENITVPDTKVNFYTWKRMDVGQQALEVWQG LALLSEAILRGQALLANASQPSETPQLHVDKAVS SLASLTSLLRALGAQKEAMSLPEEASPAPLRTFT VDTLCKLFRIYSNFLRGKLTLYTGEACRRGDR | Canis lupus erythropoietin second site mutation R103A |
| 19 | APPRLICDSRVLERYILEAREAENVTMGCAEGCS FGENVTVPDTKVNFYSWKRMEVEQQAVEVWQG LALLSEAILQGQALLANSSQPSETLRLHVDKAVS SLASLTSLLRALGAQKEAISPPDAASAAPLRTFAV DTLCKLFRIYSNFLRGKLKLYTGEACRRGDR | Equus cahallus erythropoietin second site mutation R103A |
| 20 | MDHLWAPLWPGVGSLCLLLAGAAWAPPPNPLD PKFESKXALLAARGPEELLCFTERLEDLVCFWEE AASAGVGPDNYSFFYQLEGEPWKPCSLHQAPTA RGAVRFWCSLPTADASSFVPLELRVTAVSSGAPR YHRIIHINEVVLLDPPAGLLARRADEGGHVVLRW LPPPGAPVASLIRYEVNISSGNVAGGAQKVEILDG RTECALSNLRGRTRYTFMVRARMAEPSFGGFWS AWSEPASLLTASDLDPLILTLSLILVLILLLLAVLA LLSHRRTLKQKIWPGIPSPESEFEGLFTTHKGNFQ LWLYQNEGCLWWSPCAPFAEDPPSPLEVLSERC WGATQAAEPGAEEGPLLEPLGSEHTQDTYLVLD KWLLPRNPPSEDLPRPDGSLDMVAMHKGSEASS CSSALSLKPGPEGALGASFEYTILDPSSQLLRPRA LPPELPPTPPHIKYLYLMVSDSGISTDYSSGGSQE AQGDSSTGPYLNPYENSLIPATETSPPSYVACS | Felis catus EPO receptor Sequence EPOR203 NCBI Reference Sequence: XP_019673378.1 |
| 21 | MDHLWAPLWPGVGSLCLLLAGAAWAPPPNPLD PKFESKAALLAARGPEELLCFTERLEDLVCFWEE AASAGVGPDNYSFFYQLEGEPWKPCSLHQAPTA RGAVRFWCSLPTADASSFVPLELRVTAVSSGAPR YHRIIHINEVVLLDPPAGLLARRADEGGHVVLRW LPPPGAPVASLIRYEVNISSGNVAGGAQKVEILDG RTECALSNLRGRTRYTFMVRARMAEPSFGGFWS AWSEPASLLTASDLDPLILTLSLILVLILLLLAVLA LLSHRRTLKQKIWPGIPSPESEFEGLFTTHKGNFQ LWLYQNEGCLWWSPCAPFAEDPPSPLEVLSERC WGATQAAEPGAEEGPLLEPLGSEHTQDTYLVLD KWLLPRNPPSEDLPRPDGSLDMVAMHKGSEASS CSSALSLRPGPEGALGASFEYTILDPSSQLLRPRA LPPELPPTPPHIKYLYLMVSDSGISTDYSSGGSQE AQGDSSTGPYLNPYENSLIPATETSPPSYVACS | Felis catus EPO receptor EPOR203_39A |

TABLE 1 -continued

Description of Certain Sequences

| SEQ ID NO: | SEQUENCE | DESCRIPTION |
|---|---|---|
| 22 | MDHLWAPLWPGVGSLCLLLAGAAWAPPPNPLD PKFESKAALLAARGPEELLCFTERLEDLVCFWEE AASAGVGPDNYSFFYQLEGEPWKPCSLHQAPTA RGAVRFWCSLPTADASSFVPLELRVTAVSSGAPR YHRIIHINEVVLLDPPAGLLARRADEGGHVVLRW LPPPGAPVASLIRYEVNISSGNVAGGAQKVEILDG RTECALSNLRGRTRYTFMVRARMAEPSFGGFWS AWSEPASLLTASDLDP*GGGS*PKSCDKTHTCPPCP APELLGGPSVFLFPPKPKDTLMISRTPEVTCVVVD VSHEDPEVKFNWYVDGVEVHNAKTKPREEQYN STYRVVSVLTVLHQDWLNGKEYKCKVSNKALP APIEKTISKAKGQPREPQVYTLPPSRDELTKNQVS LTCLVKGFYPSDIAVEWESNGQPENNYKTTPPVL DSDGSFFLYSKLTVDKSRWQQGNVFSCSVMHEA LHNHYTQKSLSLSPGK | Feline EPOR203_39A ECD_Fc |
| 23 | PPPNPLDPKFESKVNMVCMRAPEASACGSSERLE DLVCFWEEAASAGVGPDNYSFFYQLEGEPWKPC SLHQAPTARGAVRFWCSLPTADASSFVPLELRVT AVSSGAPRYHRIIHINEVVLLDPPAGLLARRADE GGHVVLRWLPPPGAPVASLIRYEVNISSGNVAGG AQKVEILDGRTECALSNLRGRTRYTFMVRARMA EPSFGGFWSAWSEPASLLTASDLD | Feline EPOR201 ECD |
| 24 | PPPNPLDPKFESKGKDGSVCRPPQWFLEGNAEER LEDLVCFWEEAASAGVGPDNYSFFYQLEGEPWK PCSLHQAPTARGAVRFWCSLPTADASSFVPLELR VTAVSSGAPRYHRIIHINEVVLLDPPAGLLARRA DEGGHVVLRWLPPPGAPVASLIRYEVNISSGNVA GGAQKVEILDGRTECALSNLRGRTRYTFMVRAR MAEPSFGGFWSAWSEPASLLTASDLD | Feline EPOR202 ECD |
| 25 | PPPNPLDPKFESKXALLAARGPEELLCFTERLEDL VCFWEEAASAGVGPDNYSFFYQLEGEPWKPCSL HQAPTARGAVRFWCSLPTADASSFVPLELRVTA VSSGAPRYHRIIHINEVVLLDPPAGLLARRADEG GHVVLRWLPPPGAPVASLIRYEVNISSGNVAGGA QKVEILDGRTECALSNLRGRTRYTFMVRARMAE PSFGGFWSAWSEPASLLTASDLDP | Feline EPOR203 ECD |
| 26 | PPPNPLDPKFESKAALLAARGPEELLCFTERLEDL VCFWEEAASAGVGPDNYSFFYQLEGEPWKPCSL HQAPTARGAVRFWCSLPTADASSFVPLELRVTA VSSGAPRYHRIIHINEVVLLDPPAGLLARRADEG GHVVLRWLPPPGAPVASLIRYEVNISSGNVAGGA QKVEILDGRTECALSNLRGRTRYTFMVRARMAE PSFGGR VSAWSEPASLLTASDLDP | Feline EPOR203_39A ECD |
| 27 | MDHLWAPLWPGVGSLCLLLAGAAWAPPPNPLD PKFESKVNMVCMRAPEASACGSSERLEDLVCRV EEAASAGVGPDNYSFFYQLEGEPWKPCSLHQAP TARGAVRFWCSLPTADASSFVPLELRVTAVSSGA PRYHRIIHINEVVLLDPPAGLLARRADEGGHVVL RWLPPPGAPVASLIRYEVNISSGNVAGGAQKVEI LDGRTECALSNLRGRTRYTFMVRARMAEPSFGG FWSAWSEPASLLTASDLDPLILTLSLILVLILLLLA VLALLSHRRFTRTLKQKIWPGIPSPESEFEGLFTT HKGNFQLWLYQNEGCLWWSPCAPFAEDPPSPLE VLSERCWGATQAAEPGAEEGPLLEPLGSEHTQD TYLVLDKWLLPRNPPSEDLPRPDGSLDMVAMHK GSEASSCSSALSLKPGPEGALGASFEYTILDPSSQ LLRPRALPPELPPTPPHIKYLYLMVSDSGISTDYSS GGSQEAQGDSSTGPY LNPYENSLIPATETSPPSYV ACS | Felis catus EPO receptor Sequence EPOR201 UniProtKB-M3X491 (M3X491_FELCA) |
| 28 | MDHLWAPLWPGVGSLCLLLAGAAWAPPPNPLD PKFESKGKDGSVCRPPQWFLEGNAEERLEDLVCF WEEAASAGVGPDNYSFFYQLEGEPWKPCSLHQA PTARGAVRFWCSLPTADASSFVPLELRVTAVSSG APRYHRIIHINEVVLLDPPAGLLARRADEGGHVV LRWLPPPGAPVASLIRYEVNISSGNVAGGAQKVE ILDGRTECALSNLRGRTRYTFMVRARMAEPSFG GFWSAWSEPASLLTASDLDPLILTLSLILVLILLLL | Felis catus EPO receptor Sequence EPOR202 |

TABLE 1 -continued

Description of Certain Sequences

| SEQ ID NO: | SEQUENCE | DESCRIPTION |
|---|---|---|
|  | AVLALLSHRRTLKQKIWPGIPSPESEFEGLFTTHK GNFQLWLYQNEGCLWWSPCAPFAEDPPSPLEVL SERCWGATQAAEPGAEEGPLLEPLGSEHTQDTY LVLDKWLLPRNPPSEDLPRPDGSLDMVAMHKGS EASSCSSALSLKPGPEGALGASFEYTILDPSSQLL RPRALPPELPPTPPHIKYLYLMVSDSGISTDYSSG GSQEAQGDSSTGPYLNPYENSLIPATETSPPSYVA CS |  |
| 29 | DPKFESKVNMVCMRAPEASACGSSERLEDLVCF WEEAASAGVGPDNYSFFYQLEGEPWKPCSLHQA PTARGAVRFWCSLPTADASSFVPLELRVTAVSSG APRYHRIIHINEVVLLDPPAGLLARRADEGGHVV LRWLPPPGAPVASLIRYEVNISSGNVAGGAQKVE ILDGRTECALSNLRGRTRYTFMVRARMAEPSFG GFWSAWSEPASLLT | Feline EPOR201 ECD (minimal) |
| 30 | DPKFESKGKDGSVCRPPQWFLEGNAEERLEDLV CFWEEAASAGVGPDNY SFFYQLEGEPWKPCSLH QAPTARGAVRFWCSLPTADASSFVPLELRVTAVS SGAPRYHRIIHINEVVLLDPPAGLLARRADEGGH VVLRWLPPPGAPVASLIRYEVNISSGNVAGGAQK VEILDGRTECALSNLRGRTRYTFMVRARMAEPSF GGFWSAWSEPASLLT | Feline EPOR202 ECD (minimal) |
| 31 | DPKFESKAALLAARGPEELLCFTERLEDLVCFWE EAASAGVGPDNYSFFYQLEGEPWKPCSLHQAPT ARGAVRFWCSLPTADASSFVPLELRVTAVSSGAP RYHRIIHINEVVLLDPPAGLLARRADEGGHVVLR WLPPPGAPVASLIRYEVNISSGNVAGGAQKVEIL DGRTECALSNLRGRTRYTFMVRARMAEPSFGGF WSAWSEPASLLT | Feline EPOR203 ECD (minimal) |
| 32 | MDHLWAPLWPGVGSLCLLLAGAAWAPPPNPLD PKFESKGKDGSVCRPPQXXXXTERLEDLVCFWE EAASAGVGPDNYSFFYQLEGEPWKPCSLHQAPT ARGAVRFWCSLPTADASSFVPLELRVTAVSSGAP RYHRIIHINEVVLLDPPAGLLARRADEGGHVVLR WLPPTOAPVASLIRYEVNISSGNVAGGAQKVEIL DGRTECALSNLRGRTRYTFMVRARMAEPSFGGF WSAWSEPASLLTASDLDPLILTLSLILVLILLLLAV LALLSHRRTLKQKIWPGIPSPESEFEGLFTTHKGN FQLWLYQNEGCLVVWSPCAPFAEDPPSPLEVLSE RCWGATQAAEPGAEEGPLLEPLGSEHTQDTYLV LDKWLLPRNPPSEDLPRPDGSLDMYAMHKGSEA SSCSSALSLKPGPEGALGASFEYTIEDPSSQELRPR ALPPELPPTPPHIKYLYLMVSDSGISTDYSSGGSQ EAQGDSSTGPYLNPYENSLIPATETSPPSYVACS | Felis catus EPO receptor Sequence UniProtKB-M3W333 (M3W333_FELCA) |

DETAILED DESCRIPTION OF THE INVENTIONS

The present disclosure provides structural evidence that wild-type feline EPO having a glycine at position 18 (EPO G18) in the mature form may have modified effect on the second receptor binding site and that a glutamic acid at position 18 (EPO E18) may have improved feline EPO second site binding activity. The present disclosure describes how E18 was identified as potentially interacting with at least three amino acids (R14, T15 and L97) at the second binding site of feline EPO. The second binding site is understood to facilitate EPO receptor dimerization.

The present disclosure provides analogs of wild-type feline EPO E44 precursor (SEQ ID NO: 2, where E44 corresponds to E18 in the mature EPO) and wild-type feline EPO E18 mature (SEQ ID NO: 13) polypeptides having one or more additional glycosylation sites. For example, amino acid locations of feline EPO suitable for introducing additional N-linked glycosylation sites (singly or in any combination) are provided. Methods of producing or purifying the feline EPO polypeptides, including acidic and basic fractions of feline EPO polypeptides, are also provided as are methods of treatment using feline EPO polypeptides. Formulations for single dose and/or multi dose pharmaceutical compositions of EPO polypeptides, including feline EPO polypeptides, are also described. Nucleic acids, vectors, expression systems encoding feline EPO polypeptides and methods of expressing those polypeptides, including controlled expression, by gene therapy methods are described.

EPO polypeptides having a mutation in the second binding site and methods of administering those EPO polypeptides or nucleic acids expressing those EPO polypeptides for the treatment of polycythemia in mammals are also described herein. EPO polypeptides having a mutation in the second binding site may maintain high affinity for the first EPO receptor yet have defects in EPO receptor dimerization. EPO polypeptides having a second-site mutation may prevent endogenous EPO from functioning by occupying EPO receptors. Also, described herein are polypeptides comprising an extracellular domain of feline EPO receptor and methods of administering those EPOR polypeptides or nucleic acids encoding those EPOR polypeptides for the treatment of polycythemia in mammals.

For the convenience of the reader, the following definitions of terms used herein are provided.

As used herein, numerical terms such as $K_d$ are calculated based upon scientific measurements and, thus, are subject to appropriate measurement error. In some instances, a numerical term may include numerical values that are rounded to the nearest significant figure.

As used herein, "a" or "an" means "at least one" or "one or more" unless otherwise specified. As used herein, the term "or" means "and/or" unless specified otherwise. In the context of a multiple dependent claim, the use of "or" when referring back to other claims refers to those claims in the alternative only.

Exemplary EPO Polypeptides

Novel feline EPO polypeptides are provided, for example, EPO polypeptides comprising the amino acid sequence of SEQ ID NO: 2 or SEQ ID NO: 13 except for the presence of at least one N-linked glycosylation site not present in SEQ ID NO: 2 or SEQ ID NO: 13.

"Amino acid sequence" means a sequence of amino acids in a protein, and includes sequences of amino acids in which one or more amino acids of the sequence have had their side-groups chemically modified, as well as those in which, relative to a known sequence, one or more amino acids have been replaced, inserted or deleted, without thereby eliminating a desired property, such as ability to bind EPO receptor. An amino acid sequence may also be referred to as a peptide, oligopeptide, or protein.

"Erythropoietin," "EPO," or "EPO polypeptide," as used herein, is a polypeptide comprising the entirety or a fragment of EPO.

For example, "EPO" refers to an EPO polypeptide from any vertebrate source, including mammals such as primates (e.g., humans and cynomolgus monkeys), rodents (e.g., mice and rats), and companion animals (e.g., dogs, cats, and equine), unless otherwise indicated. In some embodiments, EPO polypeptide comprises the amino acid sequence of SEQ ID NO: 1, SEQ ID NO: 2, SEQ ID NO: 3, SEQ ID NO: 4, SEQ ID NO: 9, SEQ ID NO: 10, SEQ ID NO: 10, SEQ ID NO: 11, SEQ ID NO: 12, SEQ ID NO: 13, SEQ ID NO: 14, or SEQ ID NO: 15.

"Erythropoietin receptor," "EPO receptor," or "EPOR," as used herein, is a polypeptide comprising the entirety or a portion of EPO receptor that binds to an EPO polypeptide.

For example, "EPOR" refers to an EPOR polypeptide from any vertebrate source, including mammals such as primates (e.g., humans and cynomolgus monkeys), rodents (e.g., mice and rats), and companion animals (e.g., dogs, cats, and equine), unless otherwise indicated. In some embodiments, EPOR comprises the amino acid sequence of SEQ ID NO: 5, SEQ ID NO: 6, SEQ ID NO: 7, SEQ ID NO: 8, SEQ ID NO: 20, SEQ ID NO: 21, SEQ ID NO: 22, SEQ ID NO: 23, SEQ ID N: 24, SEQ ID NO: 25, SEQ ID NO: 26, SEQ ID NO: 27, SEQ ID NO: 28, SEQ ID NO: 29, SEQ ID NO: 30, or SEQ ID NO: 31.

The term "companion animal species" or "companion animal" refers to an animal suitable to be a companion to humans. In some embodiments, a companion animal is a dog, cat, or horse. In some embodiments, a companion animal is a rabbit, ferret, guinea pig, or rodent, etc. In some embodiments, a companion animal is a cow or pig.

An "extracellular domain" ("ECD") is the portion of a polypeptide that extends beyond the transmembrane domain into the extracellular space. The term "extracellular domain," as used herein, may comprise a complete extracellular domain or may comprise a truncated extracellular domain missing one or more amino acids, that binds to its ligand. The composition of the extracellular domain may depend on the algorithm used to determine which amino acids are in the membrane. Different algorithms may predict, and different systems may express, different extracellular domains for a given protein.

An extracellular domain of an EPOR polypeptide may comprise a complete extracellular domain or a truncated extracellular domain of EPOR that binds EPO. In some embodiments, an extracellular domain of an EPOR polypeptide is an extracellular domain of an EPOR polypeptide derived from a companion animal species. For example, in some embodiments, an extracellular domain of an EPOR polypeptide is derived from canine EPOR, feline EPOR, equine EPOR, or human EPOR. In some embodiments, an extracellular domain of an EPOR polypeptide comprises the amino acid sequence of SEQ ID NO: 23, SEQ ID NO: 24, SEQ ID NO: 25, SEQ ID NO: 26, SEQ ID NO: 29, SEQ ID NO: 30, or SEQ ID NO: 31.

"Wild-type" refers to a non-mutated version of a polypeptide that occurs in nature, or a fragment thereof. A wild-type polypeptide may be produced recombinantly.

A "biologically active" entity, or an entity having "biological activity," is an entity having any function related to or associated with a metabolic or physiological process, and/or having structural, regulatory, or biochemical functions of a naturally-occurring molecule. A biologically active polypeptide or fragment thereof includes one that can participate in a biological reaction, including, but not limited to, a ligand-receptor interaction or antigen-antibody binding. The biological activity can include an improved desired activity, or a decreased undesirable activity. An entity may demonstrate biological activity when it participates in a molecular interaction with another molecule, when it has therapeutic value in alleviating a disease condition, when it has prophylactic value in inducing an immune response, when it has diagnostic and/or prognostic value in determining the presence of a molecule.

An "analog" is a polypeptide that differs from a reference polypeptide by single or multiple amino acid substitutions, deletions, and/or additions that substantially retains at least one biological activity of the reference polypeptide.

As used herein, "percent (%) amino acid sequence identity" and "homology" with respect to a polypeptide sequence are defined as the percentage of amino acid residues in a candidate sequence that are identical with the amino acid residues in the specific peptide or polypeptide sequence, after aligning the sequences and introducing gaps, if necessary to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or MEGALINE™ (DNASTAR) software. Those skilled in the art can determine appropriate parameters for measuring alignment, including any algorithms needed to achieve maximal alignment over the full length of sequences being compared.

In some embodiments, an analog has at least about 50% amino acid sequence identity, at least about 60% amino acid sequence identity, at least about 65% amino acid sequence identity, at least about 70% amino acid sequence identity, at least about 75% amino acid sequence identity, at least about 80% amino acid sequence identity, at least about 85% amino acid sequence identity, at least about 90% amino acid sequence identity, at least about 95% amino acid sequence identity, at least about 97% amino acid sequence identity, at least about 98% amino acid sequence identity, or at least about 99% amino acid sequence identity with the wild-type sequence polypeptide.

An amino acid substitution may include but is not limited to the replacement of one amino acid in a polypeptide with another amino acid. Exemplary substitutions are shown in Table 2. Amino acid substitutions may be introduced into a molecule of interest and the products screened for a desired activity, for example, retained/improved receptor binding, decreased immunogenicity, or improved pharmacokinetics.

TABLE 2

| Original Residue | Exemplary Substitutions |
|---|---|
| Ala (A) | Val; Leu; Ile |
| Arg (R) | Lys; Gln; Asn |
| Asn (N) | Gln; His; Asp; Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes with another class.

In some embodiments, the EPO polypeptide comprises the amino acid sequence of SEQ ID NO: 2 or SEQ ID NO: 13 except for the presence of at least one N-linked glycosylation site not present in SEQ ID NO: 2 or SEQ ID NO: 13. In some embodiments, the at least one N-linked glycosylation site comprises the sequence asparagine-xaa-serine, wherein xaa is any amino acid except proline. In some embodiments, the at least one N-linked glycosylation site comprises the sequence asparagine-xaa-threonine, wherein xaa is any amino acid except proline. In some embodiments, the at least one N-linked glycosylation site does not overlap with another N-linked glycosylation site.

In some embodiments, the EPO polypeptide comprises an N-linked glycosylation site at amino acid positions 47-49, 55-57, 56-58, 60-62, 61-63, 79-81, 82-84, 91-93, 92-94, 97-99, 98-100, 99-101, 112-114, 113-115, 114-116, 115-117, 116-118, 137-139, 140-142, 141-143, 142-144, 143-145, 144-146, 145-147, 146-148, 147-149, 148-150, 149-151, 150-152, 161-163, 162-164, 184-186, and/or 186-188 of SEQ ID NO: 2.

In some embodiments, the EPO polypeptide comprises an N-linked glycosylation site at amino acid positions 21-23, 29-31, 30-32, 34-36, 35-37, 53-55, 56-58, 65-67, 66-68, 71-73, 72-74, 73-75, 86-88, 87-89, 88-90, 89-91, 90-92, 111-113, 114-116, 115-117, 116-118, 117-119, 118-120, 119-121, 120-122, 121-123, 122-124, 123-125, 124-126, 135-137, 136-138, 158-160, and/or 162-164 of SEQ ID NO: 13.

In some embodiments, the EPO polypeptide comprises a valine at an amino acid position corresponding to position 113 of SEQ ID NO: 2.

In some embodiments, the EPO polypeptide comprises the amino acid sequence of SEQ ID NO: 4 or SEQ ID NO: 15.

In some embodiments, the EPO polypeptide comprises one or more amino acid modifications listed in Table 3, below.

TABLE 3

| | Amino acid substitutions for N-linked glycosylation sites | |
|---|---|---|
| Analog No. | Based on wt fEPO E44 precursor sequence (SEQ ID NO: 2) | Based on wt fEPO E18 mature sequence (SEQ ID NO: 13) |
| 1 | N47S49 | N21S23 |
| 2 | N47T49 | N21T23 |
| 3 | N55S57 | N29S31 |
| 4 | N55T57 | N29T31 |
| 5 | N56S58 | N30S32 |
| 6 | N56T58 | N30T32 |
| 7 | N60 | N34 |
| 8 | N60T62 | N34T36 |
| 9 | N61S63 | N35S37 |
| 10 | N61T63 | N35T37 |
| 11 | N79S81 | N53S55 |
| 12 | N79T81 | N53T55 |
| 13 | N82S84 | N56S58 |
| 14 | N82T84 | N56T58 |
| 15 | N91S93 | N65S67 |
| 16 | N91T93 | N65T67 |
| 17 | N92S94 | N66S68 |
| 18 | N92T94 | N66T68 |
| 19 | N97S99 | N71S73 |
| 20 | N97T99 | N71T73 |
| 21 | N98S100 | N72S74 |
| 22 | N98T100 | N72T74 |
| 23 | N99S101 | N73S75 |
| 24 | N99T101 | N73T75 |
| 25 | N112*X113 | N86*X87 |
| 26 | N112*X113T114 | N86*X87T88 |
| 27 | N113S115 | N87S89 |
| 28 | N113T115 | N87T89 |
| 29 | N114S116 | N88S90 |
| 30 | N114 | N88 |
| 31 | N115S117 | N89S91 |
| 32 | N115T117 | N89T91 |
| 33 | N116S118 | N90S92 |
| 34 | N116T118 | N90T92 |
| 35 | N137S139 | N111S113 |
| 36 | N137T139 | N111T113 |
| 37 | N140S142 | N114S116 |
| 38 | N140T142 | N114T116 |
| 39 | N141S143 | N115S117 |
| 40 | N141T143 | N115T117 |
| 41 | N142S144 | N116S118 |
| 42 | N142T144 | N116T118 |
| 43 | N143S145 | N117S119 |
| 44 | N143 | N117 |
| 45 | N144 | N118 |

TABLE 3-continued Amino acid substitutions for N-linked glycosylation sites

| Analog No. | Based on wt fEPO E44 precursor sequence (SEQ ID NO: 2) | Based on wt fEPO E18 mature sequence (SEQ ID NO: 13) |
|---|---|---|
| 46 | N144T146 | N118T120 |
| 47 | N145S147 | N119S121 |
| 48 | N145T147 | N119T121 |
| 49 | N146S148 | N120S122 |
| 50 | N146T148 | N120T122 |
| 51 | N147*X148S149 | N121*X122S123 |
| 52 | N147*X148T149 | N121*X122T123 |
| 53 | N148S150 | N122S124 |
| 54 | N148T150 | N122T124 |
| 55 | N149S151 | N123S125 |
| 56 | N149 | N123 |
| 57 | N150 | N124 |
| 58 | N150T152 | N124T126 |
| 59 | N161S163 | N135S137 |
| 60 | N161 | N135 |
| 61 | N162S164 | N136S138 |
| 62 | N162T164 | N136T138 |
| 63 | N184S186 | N158S160 |
| 64 | N184T186 | N158T160 |
| 65 | N186S188 | N162S164 |
| 66 | N186T188 | N162T164 |

*X indicates any amino acid except proline.

An "amino acid derivative," as used herein, refers to any amino acid, modified amino acid, and/or amino acid analogue, that is not one of the 20 common natural amino acids found in humans. Exemplary amino acid derivatives include natural amino acids not found in humans (e.g., seleno cysteine and pyrrolysine, which may be found in some microorganisms) and unnatural amino acids. Exemplary amino acid derivatives, include, but are not limited to, amino acid derivatives commercially available through chemical product manufacturers and distributors (e.g., sigmaaldrich.com/chemistry/chemistry-products.html?TablePage=16274965, accessed on May 6, 2017, which is incorporated herein by reference). One or more amino acid derivative maybe incorporated into a polypeptide at a specific location using translation systems that utilize host cells, orthogonal aminoacyl-tRNA synthetases derived from eubacterial synthetases, orthogonal tRNAs, and an amino acid derivative. For further descriptions, see, e.g., U.S. Pat. No. 9,624,485.

In some embodiments, an EPO polypeptide or other polypeptide described herein comprises an amino acid substitution with an amino acid derivative. In some embodiments, the amino acid derivative is an asparagine derivative, a serine derivative, a threonine derivative, or an alanine derivative.

"Glycosylated," as used herein, refers to a polypeptide having one or more glycan moieties covalently attached.

A "glycan" or "glycan moiety," as used herein, refers to monosaccharides linked glycosidically.

Glycans are attached to glycopeptides in several ways, of which N-linked to asparagine and O-linked to serine and threonine are the most relevant for recombinant therapeutic glycoproteins. N-linked glycosylation occurs at the consensus sequence Asn-Xaa-Ser/Thr, where Xaa can be any amino acid except proline.

"Sialylated," as used herein, refers to a polypeptide having one or more sialyic acid moieties covalently attached.

A variety of approaches for producing glycosylated and sialylated proteins have been developed. See, e.g., Savinova, et al., *Applied Biochem & Microbiol.* 51(8):827-33 (2015).

"PEGylated," as used herein, refers to a polypeptide having one or more polyethylene glycol (PEG) moieties associated or covalently or non-covalently attached.

In some embodiments, the EPO polypeptide is glycosylated. In some embodiments, the EPO polypeptide comprises at least one glycan moiety attached to an N-linked glycosylation site. In some embodiments, the EPO polypeptide is sialylated. In some embodiments, the EPO polypeptide is PEGylated. In some embodiments, the EPO polypeptide is PEGylated at a glycan. In some embodiments, the EPO polypeptide is PEGylated at a primary amine. In some embodiments, the EPO polypeptide is PEGylated at the N-terminal alpha-amine. In some embodiments, the EPO polypeptide is glycosylated, sialylated, and/or PEGylated.

Exemplary EPO Polypeptide Expression and Production

Polynucleotide sequences that encode all or part of an EPO polypeptide with or without a signal sequence are provided. If a homologous signal sequence (i.e., a signal sequence of wild-type EPO) is not used in the construction of the nucleic acid molecule, then another signal sequence may be used, for example, any one of the signal sequences described in PCT/US06/02951.

Typically, a nucleotide sequence encoding the polypeptide of interest, such as an EPO polypeptide or another polypeptide described herein, is inserted into an expression vector, suitable for expression in a selected host cell.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters or enhancers) that regulate the expression of the polypeptide of interest, or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A vector may be a DNA plasmid deliverable via non-viral methods (e.g., naked DNA, formulated DNA, or liposome), or via viral methods. In some embodiments, the vector is a viral vector, such as a retroviral vector, a herpesviral vector, an adenoviral vector, an adeno-associated viral vector, or a poxviral vector. The vector may be a bacterial vector.

The term "expression system," as used herein, refers to a combination of an expression vector and at least one additional vector. The combination may be deliverable via non-viral or via viral methods.

In some embodiments, the expression system comprises an expression vector and a vector comprising a regulatory sequence (e.g., a nucleic acid sequence encoding a transcription factor or microRNA).

Expression of an EPO or EPOR polypeptide described herein may be regulated to prevent excessive production of EPO or EPOR in vivo. Controlled expression may reduce immunogenicity, polycythemia (over production of red blood cells), or other negative effects. There are many known methods of controlling gene regulation in vitro and in vivo, such as tetracycline responsive systems, micro RNA regulated systems, or hypoxia-inducible systems (e.g., use of prolyl hydroxylase to activate hypoxia-inducible promoters or enhancers).

The term "regulatory sequence" (also referred to as a "regulatory region" or "regulatory element") refers to a nucleic acid sequence that facilitates and/or controls gene expression and/or protein expression, either directly or indirectly. A regulatory sequence may be a promoter, enhancer, silencer, or a nucleic acid sequence encoding a micro RNA (miRNA) or transcription factor. Regulatory sequences may increase or decrease gene expression and/or protein expression.

In some embodiments, a regulatory sequence binds regulatory proteins, such as transcription factors, to control gene expression and/or protein expression. In some embodiments, a regulatory sequence encodes a transcription factor that controls gene expression and/or protein expression. In some embodiments, a regulatory sequence encodes a miRNA that binds to a target mRNA to control protein expression.

In some embodiments, the regulatory sequence is a controllable regulatory sequence. In some embodiments, the regulatory sequence is an uncontrollable regulatory sequence, such as a constitutive promoter (e.g., a CMV promoter). In some embodiments, the regulatory sequence is a positive regulatory sequence, such as a promoter. In some embodiments, the regulatory sequence is a negative regulatory sequence, such as a silencer. In some embodiments, the regulatory sequence provides for transient, inducible (e.g., tetracycline-responsive promoter, or hypoxia-inducible promoter), and/or tissue-specific gene expression and/or protein expression.

In some embodiments, the regulatory sequence is operably linked to the nucleic acids encoding the EPO polypeptides (coding sequence) of the present disclosure. The regulatory sequence need not be contiguous with the coding sequence as long as they function to direct the expression of the encoded polypeptides. Thus, for example, intervening untranslated yet transcribed sequences may be present between a promoter sequence and a coding sequence and the promoter sequence may still be considered "operably linked" to the coding sequence.

In some embodiments, the regulatory sequence is not operably linked to the nucleic acids encoding the EPO polypeptides of the present disclosure. For example, the regulatory sequence may be a microRNA sequence or transcription factor expressed from the same vector or a different vector as the nucleic acids encoding the EPO polypeptides.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NS0 cells, PER.C6® cells (Crucell), 293 cells, and CHO cells, and their derivatives, such as 293-6E, DG-44, CHO-S, and CHO-K cells. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) encoding an amino acid sequence(s) provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated."

In some embodiments, the EPO polypeptide or another polypeptide described herein is isolated using chromatography, such as size exclusion chromatography, ion exchange chromatography, protein A column chromatography, hydrophobic interaction chromatography, CHT chromatography, and/or synthetic molecule conjugated resin chromatography (e.g., His tag affinity column chromatography). In some embodiments, the EPO polypeptide or another polypeptide described herein is isolated using Capto Butyl column chromatography, cation-exchange column chromatography, anion-exchange column chromatography, and/or mixed-mode column chromatography. In some embodiments, the EPO polypeptide or another polypeptide described herein is isolated using a combination of chromatography methods and/or columns.

In some embodiments, the method of production or isolation further comprises inactivating or removing any viruses.

The term "isoelectric point" or "pI," as used herein refers to the pH at which a molecule carries no net electrical charge and/or does not migrate further in an electric field, as determined by isoelectric focusing.

The term "range of isoelectric points," as used herein refers to the range of pHs at which a plurality of molecules carries no net electrical charge and/or do not migrate further in an electric field, as determined by isoelectric focusing.

In some embodiments, a composition comprises EPO polypeptides having a range of isoelectric points of from about 1 to about 3.5, of from about 1.5 to about 3.5, of from about 2 to about 3.5, of from about 2.5 to about 3.5, of from about 3 to about 3.5, of about 3.5 or less, or of about 3 or less, as determined by isoelectric focusing. In some embodiments, a composition comprises an acidic fraction of EPO polypeptides having a range of isoelectric points of from about 1 to about 3.5, of from about 1.5 to about 3.5, of from about 2 to about 3.5, of from about 2.5 to about 3.5, of from about 3 to about 3.5, of about 3.5 or less, or of about 3 or less, as determined by isoelectric focusing. In some embodiments, a composition comprises a high sialylation fraction of EPO polypeptides having a range of isoelectric points of from about 1 to about 3.5, of from about 1.5 to about 3.5, of from about 2 to about 3.5, of from about 2.5 to about 3.5, of from about 3 to about 3.5, of about 3.5 or less, or of about 3 or less, as determined by isoelectric focusing.

In some embodiments, a composition comprises EPO polypeptides having a range of isoelectric points of from about 3.5 to about 6, of from about 4 to about 6, of from about 4.5 to about 6, of from about 5 to about 6, of from about 5.5 to about 6, of from about 3.5 to about 5, of from about 4 to about 5, of from about 4.5 to about 5, of about 3.5 or greater, of about 4 or greater, or of about 4.5 or greater, as determined by isoelectric focusing. In some embodiments, a composition comprises a basic fraction of EPO polypeptides having a range of isoelectric points of from about 3.5 to about 6, of from about 4 to about 6, of from about 4.5 to about 6, of from about 5 to about 6, of from about 5.5 to about 6, of from about 3.5 to about 5, of from about 4 to about 5, of from about 4.5 to about 5, of about 3.5 or greater, of about 4 or greater, or of about 4.5 or greater, as determined by isoelectric focusing. In some embodiments, a composition comprises a low sialylation fraction of EPO polypeptides having a range of isoelectric points of from about 3.5 to about 6, of from about 4 to about 6, of from about 4.5 to about 6, of from about 5 to about 6, of from about 5.5 to about 6, of from about 3.5 to about 5, of from about 4 to about 5, of from about 4.5 to about 5, of about 3.5 or greater, of about 4 or greater, or of about 4.5 or greater, as determined by isoelectric focusing.

Exemplary EPO Polypeptide Affinity to EPOR

The term "affinity" means the strength of the sum total of noncovalent interactions between a single binding site of a molecule (for example, an antibody) and its binding partner (for example, an antigen). The affinity of a molecule X for its partner Y can generally be represented by the dissociation constant ($K_D$). Affinity can be measured by common methods known in the art, such as, for example, immunoblot, ELISA KD, KinEx A, biolayer interferometry (BLI), or surface plasmon resonance devices.

The terms "$K_D$," "$K_d$," "Kd" or "Kd value" as used interchangeably to refer to the equilibrium dissociation constant of an antibody-antigen interaction. In some embodiments, the $K_d$ of the antibody is measured by using biolayer interferometry assays using a biosensor, such as an Octet® System (Pall ForteBio LLC, Fremont, Calif.) according to the supplier's instructions. Briefly, biotinylated antigen is bound to the sensor tip and the association of antibody is monitored for ninety seconds and the dissociation is monitored for 600 seconds. The buffer for dilutions and binding steps is 20 mM phosphate, 150 mM NaCl, pH 7.2. A buffer only blank curve is subtracted to correct for any drift. The data are fit to a 2:1 binding model using ForteBio data analysis software to determine association rate constant ($k_{on}$), dissociation rate constant ($k_{off}$), and the $K_d$. The equilibrium dissociation constant ($K_d$) is calculated as the ratio of $k_{off}/k_{on}$. The term "kon" refers to the rate constant for association of an antibody to an antigen and the term "koff" refers to the rate constant for dissociation of an antibody from the antibody/antigen complex.

The term "binds" to a ligand or receptor is a term that is well understood in the art, and methods to determine such binding are also well known in the art. A molecule is said to exhibit "binding" if it reacts, associates with, or has affinity for a particular cell or substance and the reaction, association, or affinity is detectable by one or more methods known in the art, such as, for example, immunoblot, ELISA KD, KinEx A, biolayer interferometry (BLI), surface plasmon resonance devices, or etc.

"Surface plasmon resonance" denotes an optical phenomenon that allows for the analysis of real-time biospecific interactions by detection of alterations in protein concentrations within a biosensor matrix, for example using the BIAcore™ system (BIAcore International AB, a GE Healthcare company, Uppsala, Sweden and Piscataway, N.J.). For further descriptions, see Jonsson et al. (1993) *Ann. Biol. Clin.* 51: 19-26.

"Biolayer interferometry" refers to an optical analytical technique that analyzes the interference pattern of light reflected from a layer of immobilized protein on a biosensor tip and an internal reference layer. Changes in the number of molecules bound to the biosensor tip cause shifts in the interference pattern that can be measured in real-time. A nonlimiting exemplary device for biolayer interferometry is an Octet® system (Pall ForteBio LLC). See, e.g., Abdiche et al., 2008, *Anal. Biochem.* 377: 209-277.

To "reduce" or "inhibit" means to decrease, reduce, or arrest an activity, function, or amount as compared to a reference. In some embodiments, by "reduce" or "inhibit" is meant the ability to cause an overall decrease of 20% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control dose (such as a placebo) over the same period of time.

To "increase" or "stimulate" means to increase, improve, or augment an activity, function, or amount as compared to a reference. In some embodiments, by "reduce" or "inhibit" is meant the ability to cause an overall increase of 20% or greater. In some embodiments, by "increase" or "stimulate" is meant the ability to cause an overall increase of 50% or greater. In some embodiments, by "increase" or "stimulate" is meant the ability to cause an overall increase of 75%, 85%, 90%, 95%, or greater. In some embodiments, the amount noted above is stimulated or increased over a period of time, relative to a control dose (such as a placebo) over the same period of time.

A "reference" as used herein, refers to any sample, standard, or level that is used for comparison purposes. A reference may be obtained from a healthy or non-diseased sample. In some examples, a reference is obtained from a non-diseased or non-treated sample of a companion animal. In some examples, a reference is obtained from one or more healthy animals of a particular species, which are not the animal being tested or treated.

In some embodiments, administration of an EPO polypeptide or nucleic acid of the present invention may result in an increase of the hematocrit percent to increases to at least 25%, or at least 26%, or at least 27%, or at least 28%, or at least 29%, or at least 30%, or at least 32%, or at least 35%, or at least 38%, or at least 40%, or at least 42%, or at least 45%, or at least 48%.

Exemplary Pharmaceutical Compositions

The terms "pharmaceutical formulation" and "pharmaceutical composition" refer to a preparation which is in such form as to permit the biological activity of the active ingredient(s) to be effective, and which contains no additional components that are unacceptably toxic to a subject to which the formulation would be administered.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. Examples of pharmaceutically acceptable carriers include alumina; aluminum stearate; lecithin; serum proteins, such as human serum albumin, canine or other animal albumin; buffers such as phosphate, citrate, tromethamine or HEPES buffers; glycine; sorbic acid; potassium sorbate; partial glyceride mixtures of saturated vegetable fatty acids; water; salts or electrolytes, such as protamine sulfate, disodium hydrogen phosphate, potassium hydrogen phosphate, sodium chloride, zinc salts, colloidal silica, or magnesium trisilicate; polyvinyl pyrrolidone, cellulose-based substances; polyethylene glycol; sucrose; mannitol; or amino acids including, but not limited to, arginine.

In some embodiments, the pharmaceutically acceptable carrier has a pH of from about 6.2 to about 7, of from about 6 to about 7.2, of from about 6.4 to about 6.8, of about 6, or of about 7 and comprises sodium phosphate and sodium chloride. In some embodiments, the pharmaceutically acceptable carrier has a pH of from about 6.2 to about 7, of from about 6 to about 7.2, of about 6, of from about 6.4 to about 6.8, or of about 7 and comprises sodium citrate and sodium chloride.

In some embodiments, the pharmaceutically acceptable carrier comprises sodium phosphate, sodium chloride, and polysorbate 80. In some embodiments, the pharmaceutically acceptable carrier comprises sodium phosphate, sodium chloride, and polysorbate 20. In some embodiments, the pharmaceutically acceptable carrier comprises sodium citrate, sodium chloride, and polysorbate 20. In some embodiments, the pharmaceutically acceptable carrier comprises sodium citrate, sodium chloride, and polysorbate 80.

In some embodiments, the pharmaceutically acceptable carrier comprises sodium chloride at a concentration of from about 100 nM to about 180 nM, of from about 110 nM to about 170 nM, of from about 120 nM to about 160 nM, of from about 130 nM to about 150 nM, of about 140 nM, of from about 130 nM to about 160 nM, of from about 120 nM to about 150 nM, of about 100 nM, of about 110 nM, of about 120 nM, of about 130 nM, of about 140 nM, of about 150 nM, of about 160 nM, of about 170 nM, or of about 180 nM.

In some embodiments, the pharmaceutically acceptable carrier comprises sodium phosphate at a concentration of from about 100 nM to about 180 nM, of from about 110 nM to about 170 nM, of from about 120 nM to about 160 nM, of from about 130 nM to about 150 nM, of about 140 nM, of from about 130 nM to about 160 nM, of from about 120 nM to about 150 nM, of about 100 nM, of about 110 nM, of about 120 nM, of about 130 nM, of about 140 nM, of about 150 nM, of about 160 nM, of about 170 nM, or of about 180 nM.

In some embodiments, the pharmaceutically acceptable carrier comprises a polysorbate at a concentration of about 550 nM to about 750 nM, of about 570 nM to about 730 nM, of about 590 nM to about 720 nM, of about 600 nM to about 700 nM, of about, 620 nM to about 680 nM, of about 640 nM to about 660 nM, of about 650 nM, of about 570 nM to about 670 nM, of about 550 nM to about 650 nM, of about 650 nM to about 750 nM, of about 630 nm to about 700 nM, or of about 670 nM to about 600 nM. In some embodiments, the polysorbate is polysorbate 80. In some embodiments, the polysorbate is polysorbate 20.

In some embodiments, the pharmaceutically acceptable carrier comprises m-cresol or benzyl alcohol. In some embodiments, the concentration of m-cresol is about 0.2%, of from about 0.1% to about 0.3%, of from about 0.08% to about 0.25%, or of from about 0.05% to about 0.25%. In some embodiments, the concentration of benzyl alcohol is about 1%, of from about 0.5% to about 2%, of from about 0.2% to about 2.5%, of about 1% to about 5%, of about 0.5% to about 5%, or of about 1% to about 3%.

The pharmaceutical composition can be stored in lyophilized form; thus, in some embodiments, the preparation process includes a lyophilization step. The lyophilized composition is then reformulated, typically as an aqueous composition suitable for parenteral administration, prior to administration to the cat. In other embodiments, particularly where the protein is highly stable to thermal and oxidative denaturation, the pharmaceutical composition can be stored as a liquid, i.e., aqueous, composition, which may be administered directly, or with appropriate dilution, to the dog, cat, or horse. It can be reconstituted with sterile Water for Injection (WFI), and Bacteriostatic reagents such benzyl alcohol may be included. Thus, the invention provides pharmaceutical compositions in both solid and liquid form.

The pH of the pharmaceutical compositions typically will be in the range of from about pH 6 to pH 8 when administered, for example about 6, about 6.2, about 6.4, about 6.6, about 6.8, about 7, about 7.2. The formulations of the invention are sterile if they are to be used for therapeutic purposes. Sterility can be achieved by any of several means known in the art, including by filtration through sterile filtration membranes (e.g., 0.2 micron membranes). Sterility may be maintained with or without anti-bacterial agents.

The pharmaceutical formulations of the invention are useful in the methods of the invention for treating anemia associated conditions in companion animals, such as cats. For example, the methods described herein include administering a therapeutically effective dose of a nucleic acid or polypeptide of the disclosure to a cat. In many embodiments, the therapeutically effective dose is administered parenterally, for example by subcutaneous administration, intravenous infusion, intravenous bolus injection, or intramuscular injection.

Thus, in accordance with the methods of the invention, an EPO polypeptide or nucleic acid, other polypeptide or nucleic acid of the present invention, or a pharmaceutical composition is administered in a therapeutically effective dose to a feline, canine, equine, or human.

In some embodiments, the therapeutically effective dose is administered once per week for at least two or three consecutive weeks, and in some embodiments, this cycle of treatment is repeated two or more times, optionally interspersed with one or more weeks of no treatment. In other embodiments, the therapeutically effective dose is administered once per day for two to five consecutive days, and in some embodiments, this cycle of treatment is repeated two or more times, optionally interspersed with one or more days or weeks of no treatment.

Exemplary Uses of EPO and EPOR ECD Polypeptides

The EPO polypeptides comprising one or more additional N-glycosylation site(s) or pharmaceutical compositions comprising the EPO polypeptides disclosed herein may be useful for treating non-regenerative anemia. A non-regenerative anemia condition may be exhibited in a companion animal, including, but not limited to, canine, feline, or equine.

The EPO polypeptides comprising an amino acid substitution in the second binding site or pharmaceutical compositions comprising second site mutant EPO polypeptides disclosed herein may be useful for treating polycythemia.

The polypeptides comprising an extracellular domain of EPOR or pharmaceutical compositions comprising the EPOR ECD polypeptides disclosed herein may be useful for treating polycythemia.

As used herein, "treatment" is an approach for obtaining beneficial or desired clinical results. "Treatment" as used herein, covers any administration or application of a therapeutic for disease in a mammal, including a companion animal. For purposes of this disclosure, beneficial or desired clinical results include, but are not limited to, any one or more of: alleviation of one or more symptoms, diminishment of extent of disease, preventing or delaying spread of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also, encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

In some embodiments, an EPO polypeptide, nucleic acid, vector, expression system, or pharmaceutical compositions comprising it can be utilized in accordance with the methods herein to treat EPO deficient or EPO insensitivity-induced conditions. In some embodiments, an EPO polypeptide, nucleic acid, vector, expression system or pharmaceutical composition is administered to a companion animal, such as a canine, a feline, or equine, to treat EPO deficient or EPO insensitivity-induced conditions. In some embodiments, an EPO polypeptide, nucleic acid, vector, expression system, or pharmaceutical compositions is administered to a companion animal, such as a canine, a feline, or equine, to treat anemia.

A "therapeutically effective amount" of a substance/molecule, agonist or antagonist may vary according to factors such as the type of disease to be treated, the disease state, the severity and course of the disease, the type of therapeutic purpose, any previous therapy, the clinical history, the response to prior treatment, the discretion of the attending veterinarian, age, sex, and weight of the animal, and the ability of the substance/molecule, agonist or antagonist to elicit a desired response in the animal. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic or prophylactic result.

In some embodiments, an EPO or EPOR polypeptide, polypeptide, nucleic acid, vector, or expression system or pharmaceutical composition is administered parenterally, by subcutaneous administration, intravenous infusion, or intramuscular injection. In some embodiments, an EPO or EPOR polypeptide, polypeptide, nucleic acid, vector, expression system, or pharmaceutical composition is administered as a bolus injection or by continuous infusion over a period of time. In some embodiments, an EPO or EPOR polypeptide, polypeptide, nucleic acid, vector, expression system, or pharmaceutical composition is administered by an intramuscular, an intraperitoneal, an intracerebrospinal, a subcutaneous, an intra-arterial, an intrasynovial, an intrathecal, or an inhalation route.

An EPO or EPOR polypeptide described herein may be administered in an amount in the range of 0.0001 mg/kg body weight to 100 mg/kg body weight per dose. In some embodiments, an EPO or EPOR polypeptide may be administered in an amount in the range of 0.0005 mg/kg body weight to 50 mg/kg body weight per dose. In some embodiments, an EPO or EPOR polypeptide may be administered in an amount in the range of 0.001 mg/kg body weight to 10 mg/kg body weight per dose. In some embodiments, an EPO polypeptide may be administered in an amount in the range of from about 1 µg/kg body weight to about 10 µg/kg body weight, or about 1 µg/kg body weight to about 5 µg/kg body weight, or about 1 µg/kg body weight, or about 3 µg/kg body weight, or about 5 µg/kg body weight, or about 10 µg/kg body weight.

An EPO or EPOR polypeptide, nucleic acid, vector, expression system, or a pharmaceutical composition can be administered to a companion animal at one time or over a series of treatments. For example, an EPO or EPOR polypeptide, nucleic acid, vector, expression system, or pharmaceutical composition may be administered at least once, more than once, at least twice, at least three times, at least four times, or at least five times, or chronically use.

In some embodiments, the dose is administered once per week for at least two or three consecutive weeks, and in some embodiments, this cycle of treatment is repeated two or more times, optionally interspersed with one or more weeks of no treatment. In other embodiments, the therapeutically effective dose is administered once per day for two to five consecutive days, and in some embodiments, this cycle of treatment is repeated two or more times, optionally interspersed with one or more days or weeks of no treatment.

Administration "in combination with" one or more further therapeutic agents includes simultaneous (concurrent) and consecutive or sequential administration in any order. The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about a specified number of minutes. The term "sequentially" is used herein to refer to administration of two or more therapeutic agents where the administration of one or more agent(s) continues after discontinuing the administration of one or more other agent(s), or wherein administration of one or more agent(s) begins before the administration of one or more other agent(s). For example, administration of the two or more therapeutic agents are administered with a time separation of more than about a specified number of minutes. As used herein, "in conjunction with" refers to administration of one treatment modality in addition to another treatment modality. As such, "in conjunction with" refers to administration of one treatment modality before, during or after administration of the other treatment modality to the animal.

Provided herein are methods of using the EPO polypeptides and polynucleotides for detection, diagnosis and monitoring of an anemia condition. For example, anemia may be detected, diagnosed, or monitored by measuring hematocrit percentage (HCT %) using standard methods. Provided herein are methods of determining whether a companion animal will respond to EPO polypeptide. In some embodiments, the method comprises detecting whether the animal has cells that express EPOR using an EPO polypeptide. In some embodiments, the method of detection comprises contacting the sample with an EPO polypeptide or polynucleotide and determining whether the level of binding differs from that of a reference or comparison sample (such as a control). In some embodiments, the method may be useful to determine whether the antibodies or polypeptides described herein are an appropriate treatment for the subject animal.

In some embodiments, the sample is a biological sample. The term "biological sample" means a quantity of a substance from a living thing or formerly living thing. In some embodiments, the biological sample is a cell or cell/tissue lysate. In some embodiments, the biological sample includes, but is not limited to, blood, (for example, whole blood), plasma, serum, urine, synovial fluid, and epithelial cells.

Various methods known in the art for detecting specific ligand-receptor binding can be used. Exemplary immunoassays which can be conducted include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (MA). An indicator moiety, or label group, can be attached to the subject antibodies and is selected so as to meet the needs of various uses of the method which are often dictated by the availability of assay equipment and compatible immunoassay procedures. Appropriate labels include, without limitation, radionuclides (for example $^{125}$I, $^{131}$I, $^{35}$S, $^{3}$H, or $^{32}$P), enzymes (for example, alkaline phosphatase, horseradish peroxidase, luciferase, or p-galactosidase), fluorescent moieties or proteins (for example, fluorescein, rhodamine, phycoerythrin, GFP, or BFP), or luminescent moieties (for example, Qdot™ nanoparticles supplied by the Quantum Dot Corporation, Palo Alto, Calif). General techniques to be used in performing the various immunoassays noted above are known to those of ordinary skill in the art.

For purposes of diagnosis, the polypeptide including EPO or EPOR can be labeled with a detectable moiety including but not limited to radioisotopes, fluorescent labels, and various enzyme-substrate labels know in the art. Methods of conjugating labels to a protein are known in the art.

The following examples illustrate particular aspects of the disclosure and are not intended in any way to limit the disclosure.

EXAMPLES

Example 1

Identification of N-Linked Glycosylation Sites for Feline EPO

Wild-type feline EPO has three N-linked glycosylation sites—at amino acid positions 50-52, 64-66, and 109-111 of wild-type feline EPO G44 precursor form (SEQ ID NO: 1 or "wild-type feline EPO G44") and at amino acid positions 24-26, 38-40, and 83-85 of wild-type G18 feline EPO mature form (SEQ ID NO: 12 or "wild-type feline EPO G18").

Additional N-linked glycosylation sites may be introduced into wild-type feline EPO amino acid sequences. For example, one, two, three, four, five, or six additional N-linked glycosylation sites may be introduced into wild-type feline EPO amino acid sequences. The N-linked glycosylation site may have a consensus sequence of Asn-Xaa-Ser/Thr, where Xaa is any amino acid except proline. Addition of one or more glycosylation sites may increase the molecular size of a feline EPO molecule, provide more sialylation sites, and/or improve the half-life of the molecule in an animal's serum.

Table 4 lists amino acid substitutions of wild-type feline EPO G44 that may be used to generate one or more additional N-linked glycosylation sites.

TABLE 4

| | Amino acid substitutions for N-linked glycosylation sites | |
|---|---|---|
| Analog No. | Based on wt feline EPO G44 sequence (SEQ ID NO: 1) | Based on wt feline EPO G18 sequence (SEQ ID NO: 12) |
| 1 | N47S49 | N21S23 |
| 2 | N47T49 | N21T23 |
| 3 | N55S57 | N29S31 |
| 4 | N55T57 | N29T31 |

TABLE 4-continued

| | Amino acid substitutions for N-linked glycosylation sites | |
|---|---|---|
| Analog No. | Based on wt feline EPO G44 sequence (SEQ ID NO: 1) | Based on wt feline EPO G18 sequence (SEQ ID NO: 12) |
| 5 | N56S58 | N30S32 |
| 6 | N56T58 | N30T32 |
| 7 | N60 | N34 |
| 8 | N60T62 | N34T36 |
| 9 | N61S63 | N35S37 |
| 10 | N61T63 | N35T37 |
| 11 | N79S81 | N53S55 |
| 12 | N79T81 | N53T55 |
| 13 | N82S84 | N56S58 |
| 14 | N82T84 | N56T58 |
| 15 | N91S93 | N65S67 |
| 16 | N91T93 | N65T67 |
| 17 | N92S94 | N66S68 |
| 18 | N92T94 | N66T68 |
| 19 | N97S99 | N71S73 |
| 20 | N97T99 | N71T73 |
| 21 | N98S100 | N72S74 |
| 22 | N98T100 | N72T74 |
| 23 | N99S101 | N73S75 |
| 24 | N99T101 | N73T75 |
| 25 | N112*X113 | N86*X87 |
| 26 | N112*X113T114 | N86*X87T88 |
| 27 | N113S115 | N87S89 |
| 28 | N113T115 | N87T89 |
| 29 | N114S116 | N88S90 |
| 30 | N114 | N88 |
| 31 | N115S117 | N89S91 |
| 32 | N115T117 | N89T91 |
| 33 | N116S118 | N90S92 |
| 34 | N116T118 | N90T92 |
| 35 | N137S139 | N111S113 |
| 36 | N137T139 | N111T113 |
| 37 | N140S142 | N114S116 |
| 38 | N140T142 | N114T116 |
| 39 | N141S143 | N115S117 |
| 40 | N141T143 | N115T117 |
| 41 | N142S144 | N116S118 |
| 42 | N142T144 | N116T118 |
| 43 | N143S145 | N117S119 |
| 44 | N143 | N117 |
| 45 | N144 | N118 |
| 46 | N144T146 | N118T120 |
| 47 | N145S147 | N119S121 |
| 48 | N145T147 | N119T121 |
| 49 | N146S148 | N120S122 |
| 50 | N146T148 | N120T122 |
| 51 | N147*X148S149 | N121*X122S123 |
| 52 | N147*X148T149 | N121*X122T123 |
| 53 | N148S150 | N122S124 |
| 54 | N148T150 | N122T124 |
| 55 | N149S151 | N123S125 |
| 56 | N149 | N123 |
| 57 | N150 | N124 |
| 58 | N150T152 | N124T126 |
| 59 | N161S163 | N135S137 |
| 60 | N161 | N135 |
| 61 | N162S164 | N136S138 |
| 62 | N162T164 | N136T138 |
| 63 | N184S186 | N158S160 |
| 64 | N184T186 | N158T160 |
| 65 | N186S188 | N162S164 |
| 66 | N186T188 | N162T164 |

*X indicates any amino acid except proline.

Example 2

Expression of Feline EPO with Additional N-Linked Glycosylation Sites

The nucleotide sequence encoding a EPO polypeptide having additional N-linked glycosylation sites compared to wild-type feline EPO G44 precursor form was chemically synthesized. Specifically, the sequence encoded "Analog 6-30 GV Precursor" (SEQ ID NO: 3), which has a glycine at position 44, a valine substitution at position 113, and two additional N-linked glycosylation sites at positions 56-58 (N56T58) and 114-116 (N114) of wild-type feline EPO precursor.

The nucleotide sequence was inserted into an expression vector and transfected into CHO DG-44 host cells. The CHO DG-44 cells were selected for high yield and stability of expression of the EPO polypeptide, using a DHFR gene on the expression vector and methotrexate-mediated gene amplification, as is known in the art. The mature form of the EPO polypeptide, named "Analog 6-30 GV Mature" (SEQ ID NO: 14) was secreted into the culture media.

Example 3

Isolation of Feline EPO

Cell lines expressing feline EPO polypeptides may be cultured until sufficient quantities of the EPO polypeptide are produced. The polypeptide may be isolated by one or more of various steps, including Capto Butyl column chromatography, cation-exchange (CEX) column chromatography, anion-exchange (AEX) column chromatography, or other chromatographic methods. Other chromatographic methods may include ion exchange column chromatography, hydrophobic interaction column chromatography, mixed mode column chromatography (e.g., CHT and/or ultimodal mode column chromatography, such as CaptoMMC). Low pH or other viral inactivation and viral removal steps may be applied. The isolated EPO polypeptide may be admixed with excipients, and sterilized by filtration to prepare a pharmaceutical composition of the invention. The pharmaceutical composition may be administered to a cat with anemia in a dose sufficient to stimulate hematopoietic activity.

When cell viabilities dropped below 95%, the supernatant was harvested by clarifying the conditioned media. For example, a combination of chromatography steps was used to purify Analog 6-30 GV Mature polypeptide (SEQ ID NO: 14). Media from CHO cells expressing the EPO polypeptide was collected and conditioned with the addition of sodium chloride (NaCl) such that the media would have an NaCl concentration of greater than 1 M NaCl so that the EPO polypeptide could bind to a Capto Butyl column (GE Healthcare Life Sciences) by hydrophobic interaction chromatography (HIC). EPO is understood to bind to a Capto Butyl column at a pH of about 5.75 to about 8.5 with about 1 to about 2.5 M NaCl. The conditioned media was clarified by centrifugation and filtration and loaded onto the Capto Butyl column. Bound EPO polypeptide was eluted from the column with 30% isopropanol at a pH of about 5.6.

The host cell proteins fractionated away were analyzed using CHO host cell protein analysis ELISA kit (Catalog No. CM015; Cygnus Technologies). At least about 95% of host cell proteins were fractionated away from EPO proteins by this purification method.

The eluate from the Capto Butyl column was loaded directly onto an SP cation-exchange (CEX) column (GE Healthcare Life Sciences) as a subtraction chromatography step. Under this loading condition of 30% isopropanol at a pH of about 5.6, EPO polypeptides flow through the SP CEX column while host cell proteins should bind.

The flow-through from the SP CEX column was loaded directly onto a Capto Q anion-exchange (AEX) column (GE Healthcare Life Sciences), which binds EPO polypeptides in 30% isopropanol at a pH of about 5.6. A pH 4 wash was added to remove a fraction of basic EPO polypeptides while a fraction acidic EPO polypeptides remained with the solid phase. The EPO polypeptide acidic fraction was eluted with 0.15 M NaCl at pH 4 and the eluate kept at pH 4 for greater than 90 minutes at ambient temperature to inactivate viruses. This step also increased the concentration of the EPO polypeptide acidic fraction.

The eluate containing the EPO polypeptide acidic fraction was loaded directly onto an SP CEX column (GE Healthcare Life Sciences) to fractionate away any residual endotoxin and basic EPO polypeptide fraction, along with further concentrating the EPO polypeptide acidic fraction. The EPO polypeptide acidic fraction was eluted with 0.5 M NaCl at pH 4 and the eluate kept at pH 4 for greater than 90 minutes at ambient temperature to inactivate viruses.

Tangential flow filtration (TFF) may be used to concentrate the acidic and basic fractions EPO polypeptide fractions. A gel filtration step using Sperdex200 may be performed to remove any aggregates and as a buffer exchange to the desired buffer (e.g. a formulation buffer as described below). A nanofiltration step may be performed to remove any residual viral contaminants.

Example 4

EPO Buffer Formulations

Thermostability of feline EPO in various buffer formulations was analyzed. Buffers containing 20 mM sodium citrate or 20 mM sodium phosphate at pH 6.2 and pH 7 were considered. Sodium chloride at a final concentration of 140 mM was used in all buffers. Polysorbate 80 and 20 were compared. Bacteriostatic reagents benzyl alcohol and m-cresol were also compared. The melting temperature (Tm) of feline EPO Analog 6-30 GV Mature at a concentration of 6 µg/µL in each buffer was measured by differential scanning fluorescence technique from 20° C. to 95° C. Table 5 lists Tm values of feline EPO in the various buffers tested.

TABLE 5

| Formulation Designation | Buffer Formulation | Melting temperature (Tm ° C.) |
|---|---|---|
| A1 | 20 mM sodium citrate 140 mM sodium chloride pH 6.2 | 55 |
| A2 | A1 + 650 nM polysorbate 80 | 54 |
| A3 | A1 + 650 nM polysorbate 20 | 52 |
| A4 | A2 + 1% benzyl alcohol | 42 |
| A5 | A2 + 0.2% m-cresol | 50 |
| A6 | A3 + 1% benzyl alcohol | no peak* |
| A7 | A3 + 0.2% m-cresol | 35 |
| B1 | 20 mM sodium citrate 140 mM sodium chloride pH 7 | 50 |
| B2 | B1 + 650 nM polysorbate 80 | 51 |
| B3 | B1 + 650 nM polysorbate 20 | 50 |
| B4 | B2 + 1% benzyl alcohol | no peak* |

TABLE 5-continued

| Formulation Designation | Buffer Formulation | Melting temperature (Tm ° C.) |
|---|---|---|
| B5 | B2 + 0.2% m-cresol | 45 |
| B6 | B3 + 1% benzyl alcohol | no peak* |
| B7 | B3 + 0.2% m-cresol | 40 |
| C1 | 20 mM sodium phosphate 140 mM sodium chloride pH 6.2 | 51 |
| C2 | C1 + 650 nM polysorbate 80 | 53 |
| C3 | C1 + 650 nM polysorbate 20 | 50 |
| C4 | C2 + 1% benzyl alcohol | 38 |
| C5 | C2 + 0.2% m-cresol | 35 |
| C6 | C3 + 1% benzyl alcohol | 50 |
| C7 | C3 + 0.2% m-cresol | 43 |
| D1 | 20 mM sodium phosphate 140 mM sodium chloride pH 7 | 51 |
| D2 | D1 + 650 nM polysorbate 80 | 53 |
| D3 | D1 + 650 nM polysorbate 20 | 51 |
| D4 | D2 + 1% benzyl alcohol | 38 |
| D5 | D2 + 0.2% m-cresol | 40 |
| D6 | D3 + 1% benzyl alcohol | 34 |
| D7 | D3 + 0.2% m-cresol | 40 |

*No peak indicates that no distinct melting point was observed.

Formulations A1, A2, A3, B1, B2, B3, C1, C2, and C3, which do not contain antibacterial agents and have a Tm of 50° C. or above may be more desirable for single dosing. Among the formulations containing antibacterial agents, Formulations A5 and C6, which have a Tm of 50° C. appear to be more desirable for multi-dosing.

Example 5

Characterization of Analog 6-30 GV Mature

Feline EPO Analog 6-30 GV Mature (SEQ ID NO: 14) isolated using the method of Example 3 was characterized.

Figure 1B:
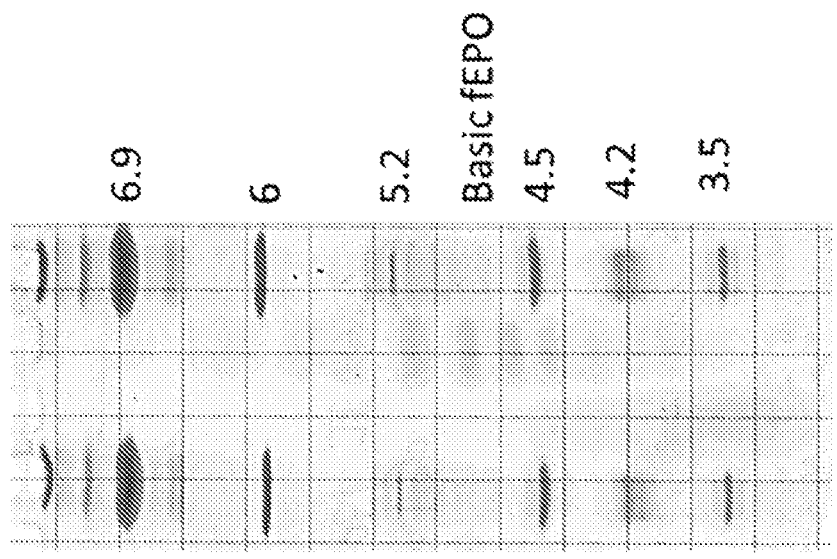

Basic and acidic Analog 6-30 GV Mature fractions were visualized through isoelectric focusing (IEF) (FIG. 1A and FIG. 2) and sodium dodecyl sulfate-polyacrylamide gel electrophoresis (SDS-PAGE) gel (FIG. 1B).

Figure 3:
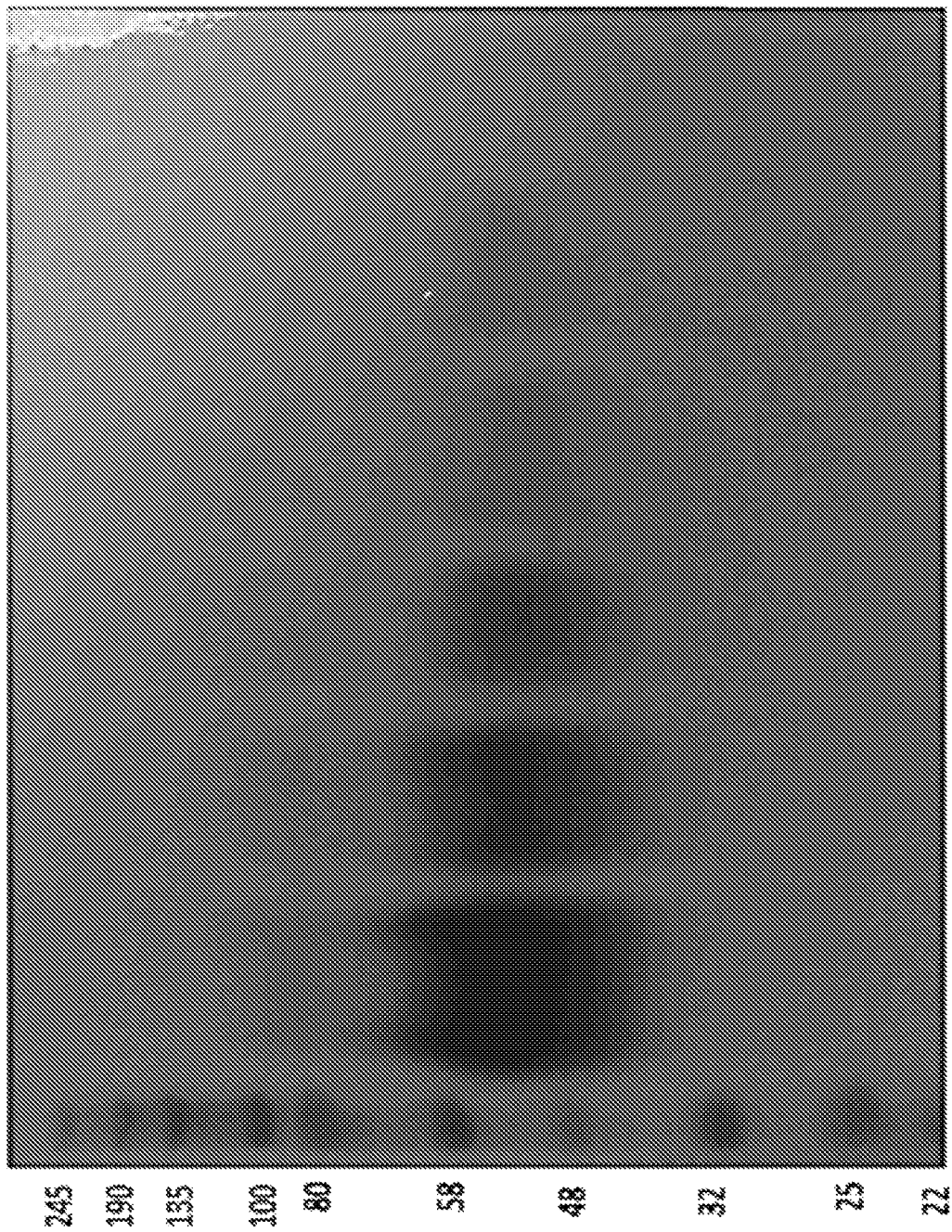
FIG. 3 shows a Western blot of isolated feline EPO Analog 6-30 GV Mature (SEQ ID NO: 14). Lane 1: molecular weight marker; Lanes 2-6: isolated Analog 6-30 GV Mature at 1 μg, 0.5 μg, 0.2 μg, 0.1 μg, and 0.05 μg, respectively.

For the Western analysis, serial dilutions of an acidic fraction of Analog 6-30 GV Mature (1 µg, 0.5 µg, 0.2 µg, 0.1 µg, and 0.05 µg) were separated by SDS-PAGE, transferred to a PVDF membrane, and the membrane probed with a rabbit anti-human EPO polyclonal antibody (Catalog No. AB-386-NA, R&D Systems) at a 1:1000 dilution (FIG. 3). The antibody was specific to the N-terminal 19 amino acids of human EPO, which are the same N-terminal 19 amino acids of feline EPO. The molecular weight of glycosylated wild-type feline EPO mature form is likely about 34 kDa. Based on FIG. 3, the molecular weight of Analog 6-30 GV Mature appears to be about 50-55 kDa. The additional glycosylation appears to have contributed to the increase in molecular size.

Figure 4A:
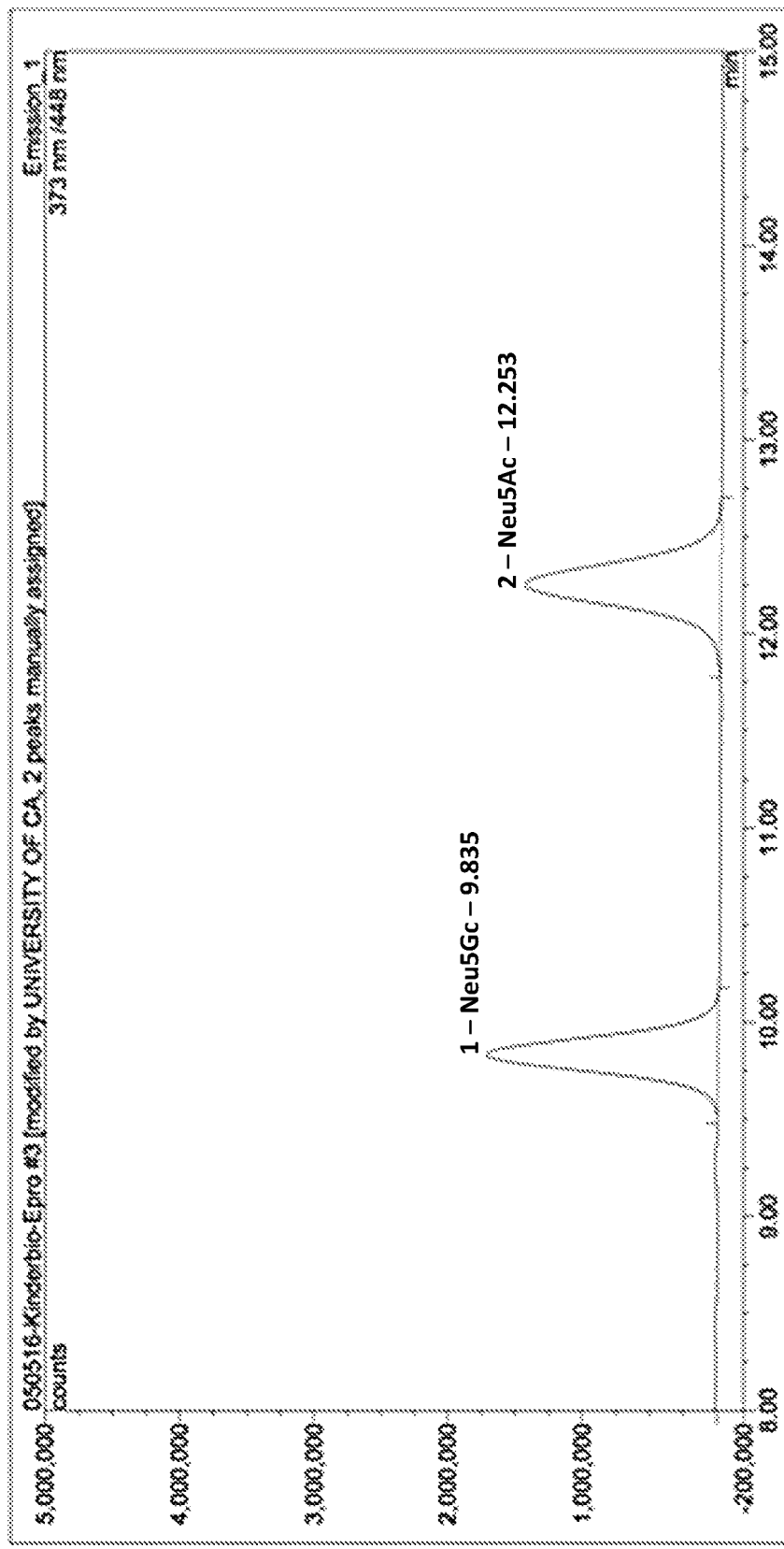
FIG. 4A shows sialic acid analysis of a commercial standard of Neu5Gc/Neu5A at a known concentration.
Figure 4B:
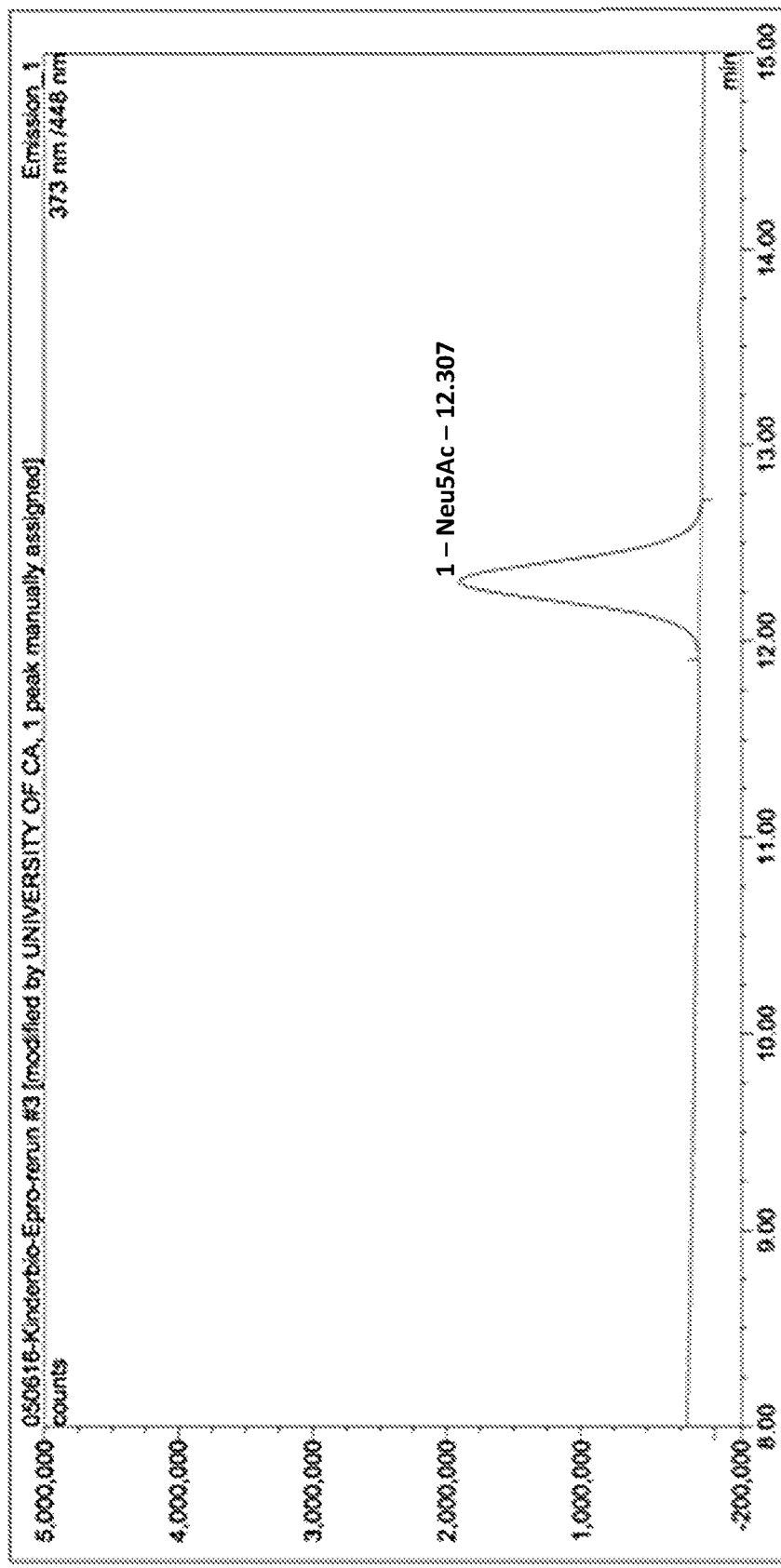
FIG. 4B shows sialic acid analysis of isolated Analog 6-30 GV Mature.

Sialylated glycosylation on a protein may enhance its in vivo pharmacokinetics. Common sialic acids that are expressed as terminal units on all vertebrate glycans typically include N-glycolylneuraminic acid (Neu5Gc) and N-acetylneuraminic acid (Neu5Ac). Sialic acid analysis of Analog 6-30 GV Mature was performed. Briefly, an acidic fraction of Analog 6-30 GV Mature was treated with 2 M acetic acid at 80° C. for 3 hours after which the acetic acid was removed under vacuum centrifuge. The treated EPO sample was filtered through a 3K spin filtering unit to remove unhydrolyzed proteins. The flow-through sample was reacted with DMB reagent. An injection amount of 0.04 µg was profiled by high-performance liquid chromatography (HPLC) using a C18 column and a fluorescence detector. N-acetylneuraminic acid was identified as the predominant form of sialic acid present on Analog 6-30 GV Mature expressed by the transfected CHO DG44 cells. No detectable N-glycolylneuraminic acid was identified (FIG. 4).

The N-terminal sequence of Analog 6-30 GV Mature was confirmed by Edman sequencing. Briefly, isolated Analog 6-30 GV Mature was separated by SDS-PAGE and transferred to a PVDF membrane (BioRad). The protein band was isolated from the membrane and subjected to N-terminal sequencing using Edman degradation at the Molecular Structure Facility at University of California, Davis. The N-terminal sequence was identified as Ala Pro Xaa Arg Leu Ile Xaa Asp Ser Arg Val, which corresponds to the N-terminal sequence of SEQ ID NO: 14.

Isolated Analog 6-30 GV Mature (SEQ ID NO: 14) was treated with N-Glycanase® (PNGase F) (Catalog No. GKE-5006A, ProZyme, CA) using the manufacturer's instructions to remove N-linked glycans. The deglycosylation process was monitored by SDS-PAGE until a 19 kD band was visualized, indicating the polypeptide was deglycosylated. The sequences of fragments of the deglycosylated Analog 6-30 GV Mature sample were analyzed using tandem mass spectrometry at Scripps Center for Metabolomics and Mass Spectrometry in California. The sequence of Analog 6-30 Mature was confirmed by mapping 77% of the peptide sequence (data not shown).

Example 6

Effect of Sialylation of Feline EPO on In Vitro Activity

The in vitro activity of an acidic fraction and a basic fraction of isolated Analog 6-30 GV Mature were compared by TF-1 cell proliferation assay. TF-1 cells are factor-dependent human erythroleukemic cells. EPO is one of the factors that promotes TF-1 cell proliferation. The acidic (or high sialyation) fraction had an isoelectric point range of about 2 to about 3.5 and the basic (or low sialyation) fraction had an isoelectric point range of about 3.5 to about 5.

Figure 5:
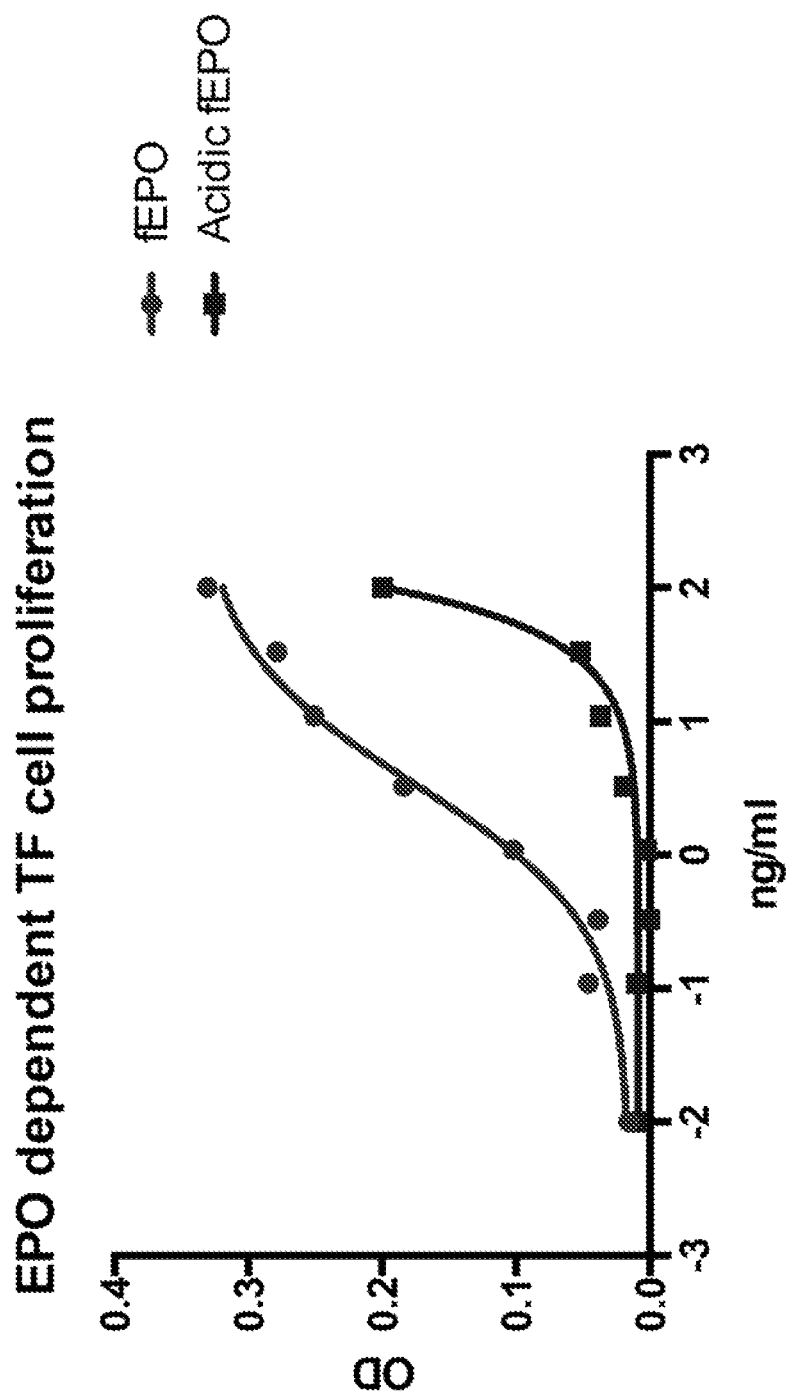
FIG. 5 shows results of a TF-1 cell proliferation assay demonstrating that high sialylation feline EPO (acidic fraction) has lower activity compared to lower sialylation feline EPO (basic fraction).

For the proliferation assay, TF-1 cells (ATCC CRL-2003) were cultivated in RPMI 1640 (Irvine Catalog No. 9160) supplemented with 10% (v/v) Fetal Bovine Serum, 2 mM L-glutamine, 100 units/mL Penicillin, 100 µg/mL Streptomycin, and 2 ng/mL rhGM-CSF (R&D Systems Catalog No. 215-GM). Before treatment with either acidic fraction or basic fraction of Analog 6-30 GV Mature, the TF-1 cells were seeded in a 96-flat well plate at $2 \times 10^5$ cells per mL and allowed to attach overnight. The next morning, the cells were treated with different concentrations of acidic and basic fractions of Analog 6-30 GV Mature. Following incubation for 48 hours, MTT reagent (Catalog No. CGD1, Sigma-Aldrich) was added to the cells for another 48-72 hours, according to the manufacturer's instructions. The insoluble purple reaction product was then dissolved with isopropanol, and the plate was read at 570 and 690 nm. The proliferation intensity was measured as a difference in optical density between 570 nm and 690 nm (ΔOD) with the background corrected. The acidic fraction of isolated Analog 6-30 GV Mature demonstrated lower potency than the basic fraction in the cell-based functional assay (FIG. 5), suggesting that higher sialyation leads to lower activity.

Example 7

Effect of Sialylation on Pharmacokinetics

A pharmacokinetics study in cats involving a single injection of a 10 μg/kg dose of a basic fraction of isolated Analog 6-30 GV Mature or a 10 μg/kg dose of an acid fraction of isolated Analog 6-30 GV Mature was conducted. The basic (or low sialylation) fraction investigated had an isoelectric point range of about 4 to about 6 and the acidic fraction had an isoelectric point range of about 2 to about 3.5. Two cats were injected subcutaneous with the basic fraction and 11 cats were injected with the acidic fraction (4 cats via intravenous injection; 4 cats via subcutaneous injection, and 3 cats via intramuscular injection).

Figure 6A:
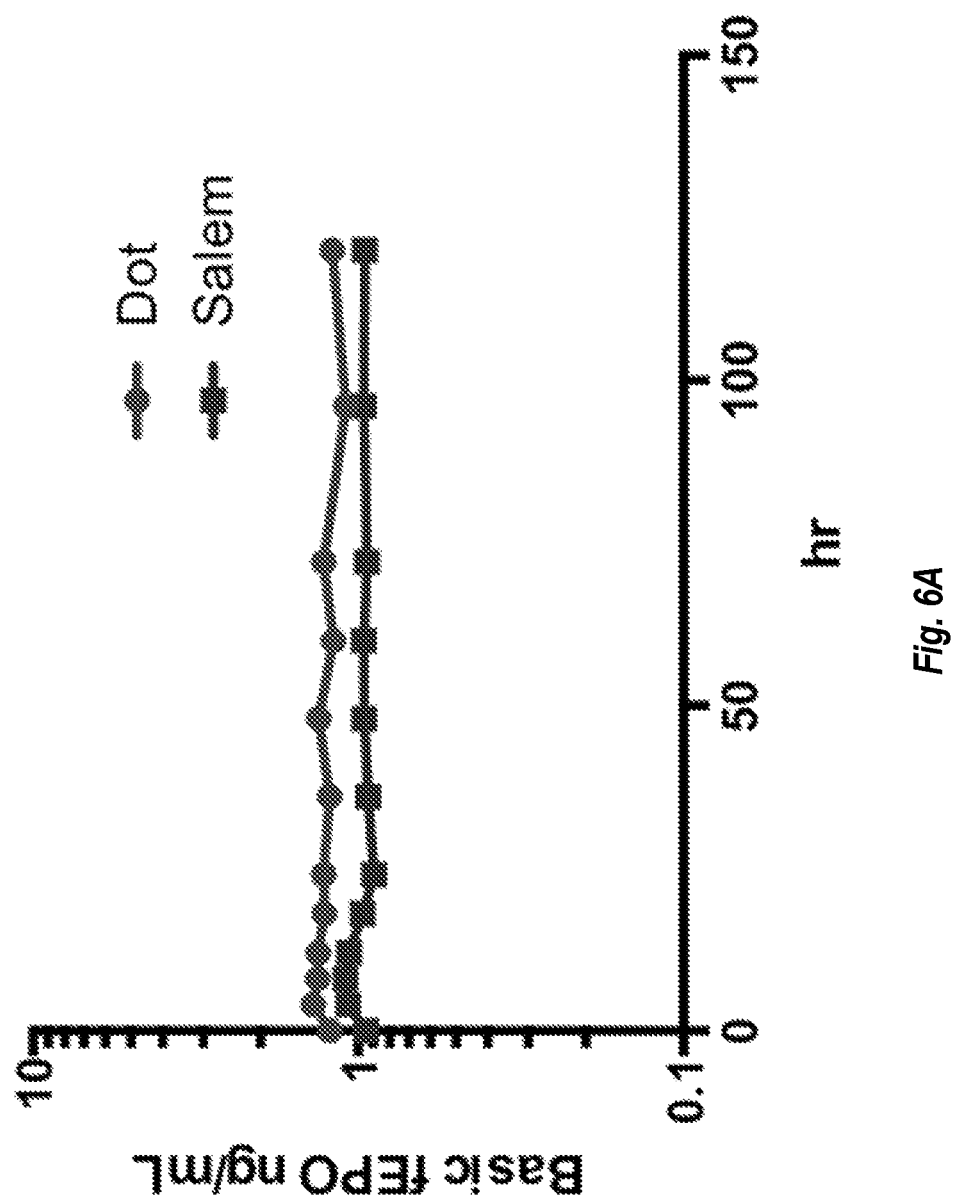
FIG. 6A shows the pharmacokinetic (PK) profile of low sialylation Analog 6-30 GV Mature (basic fraction) in two cats (Dot and Salem) following subcutaneous (SQ) injection.
Figure 6B:
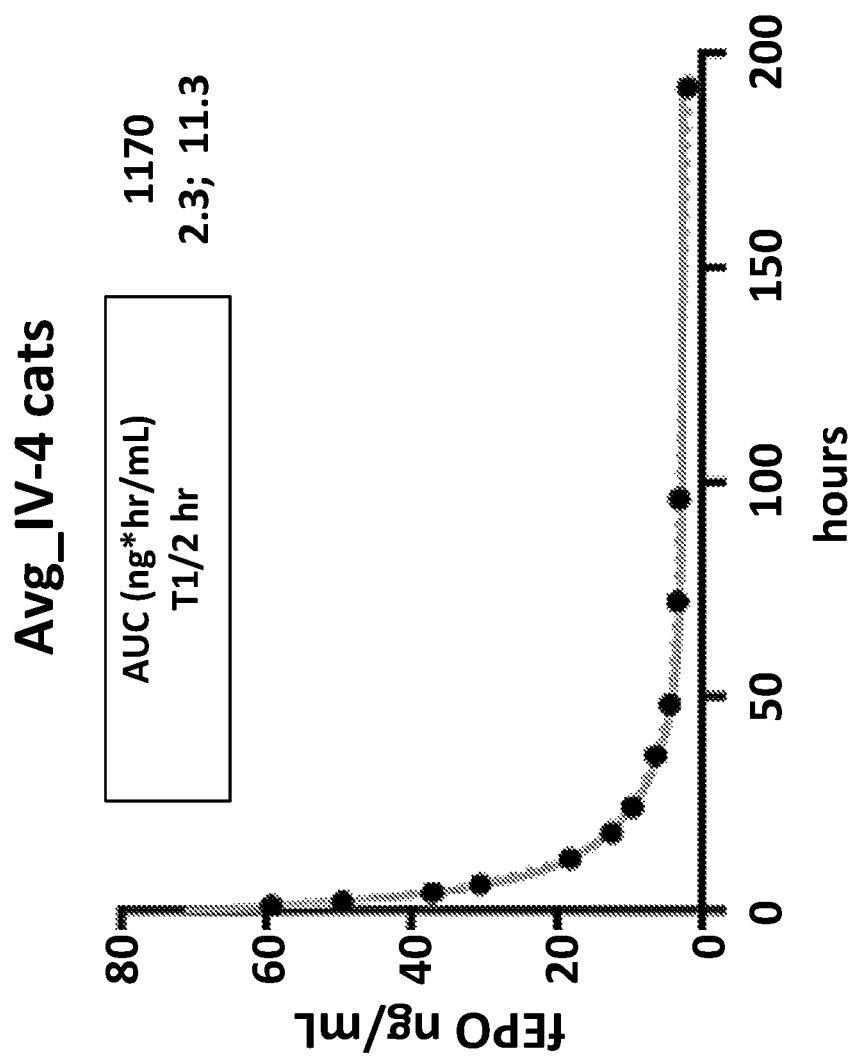
FIG. 6B shows the average PK profile and parameters of high sialylation Analog 6-30 GV Mature (acidic fraction) in four cats following intravenous (IV) injection.
Figure 6C:
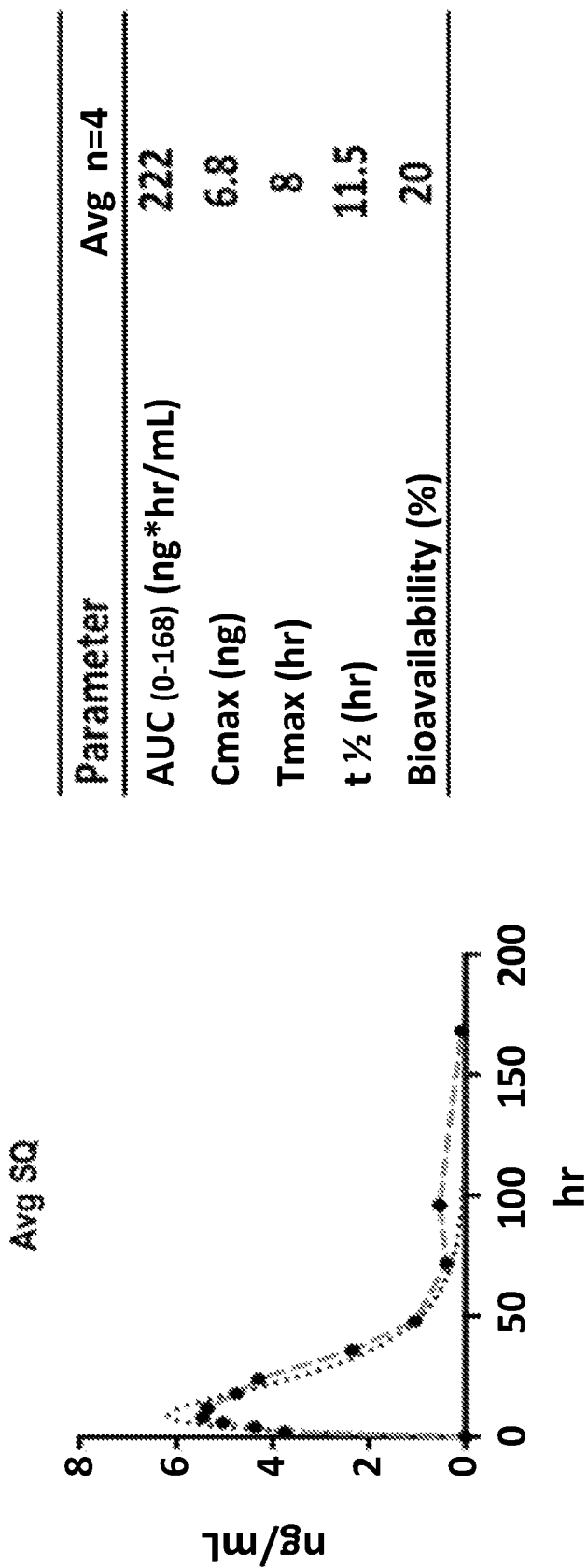
FIG. 6C shows the average PK profile and parameters of high sialylation Analog 6-30 GV Mature (acidic fraction) in four cats following subcutaneous (SQ) injection.
Figure 6D:
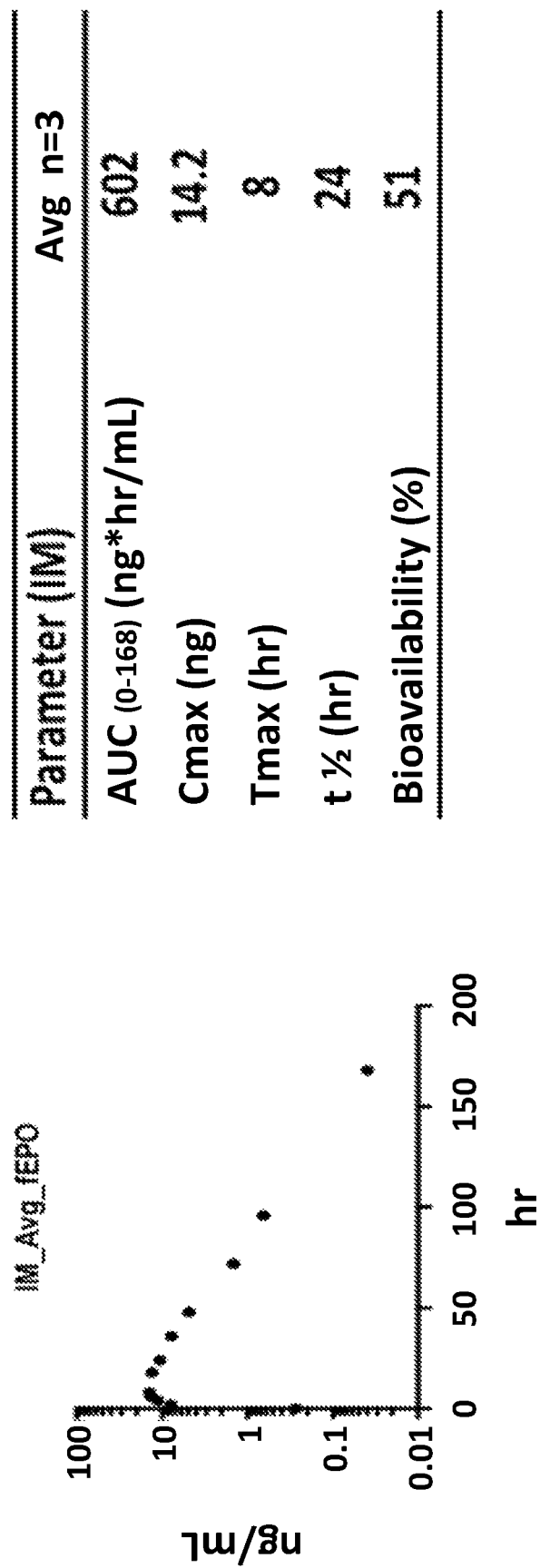
FIG. 6D shows the average PK profile and parameters of high sialylation Analog 6-30 GV Mature (acidic fraction) in three cats following intramuscular (IM) injection.

EPO concentrations from serum before injection (Time 0) and at various time points after injection were analyzed by ELISA. A sample of the basic faction of isolated Analog 6-30 GV Mature was used in the ELISA as a reference with a detection limit of 0.4 ng/mL. Very little EPO was detected over time in the serum of cats injected subcutaneous with the basic fraction of isolated Analog 6-30 GV Mature, suggesting a very short half-life of the low sialylated form (FIG. 6A). EPO concentration in the serum of cats injected with the acid fraction of isolated Analog 6-30 GV Mature by intravenous, subcutaneous, and intramuscular administration is shown in FIG. 6B, FIG. 6C, and FIG. 6D, respectively. Pharmacokinetic parameters calculated as mean values are listed in Table 6, below.

TABLE 6

| Route of Administration | Pharmacokinetic parameter (mean) | | | | |
|---|---|---|---|---|---|
| | AUC (ng*hr/mL) | $T_{1/2}$ (hrs) | $C_{max}$ (ng) | $T_{max}$ (hrs) | Bioavailability* (%) |
| Intravenous | 1170 | 11.3 | | | 100 |
| Subcutaneous | 222 | 11.5 | 6.8 | 8 | 20 |
| Intramuscular | 602 | 24 | 14.2 | 8 | 51 |

*Bioavailability is calculated based on an assumption of 100% bioavailability in the IV group.

High sialylation of Analog 6-30 GV Mature appears to have enhanced the pharmacokinetics of the polypeptide in vivo, but to have reduced its potency in an in vitro cell-based functional assay (Example 6). While the pharmacokinetics of feline EPO may be enhanced in vivo with high sialylation, the tradeoff may be lower affinity and activity. And while low sialylated feline EPO may have better affinity and activity, it likely exhibits a shorter half-life.

Example 8

Expression of Feline EPO Receptor

Several feline EPO receptor (EPOR) proteins having a single transmembrane domain result from alternatively-spliced mRNA sequences originating from differences in the nucleotide sequences of exon 3. The amino acid sequences of two EPOR proteins were obtained from the National Center for Biotechnology Information (NCBI) database: UniProtKB-M3X491 M3X491_FELCA (SEQ ID NO: 27) and UniProtKB—M3W333 M3W333_FELCA (SEQ ID NO: 32). The amino acid sequence of M3X491_FELCA is also designated as Feline EPOR201 (fEPOR201) herein. The amino acids at positions 50-53 of M3W333, however, were not known and are represented in the database by an "X." Using three-dimensional protein structure analysis, the amino acid sequence for M3W333 was modified and amino acids inserted at positions 50-53 to yield fEPOR202 (SEQ ID NO: 28).

Nucleotide sequences encoding soluble, extracellular domains of feline EPOR201 and EPOR202 (SEQ ID NOs: 23 and 24, respectively) fused to human Fc (SEQ ID NOs: 7 and 8, respectively) were synthesized, cloned into a mammalian expression vector, and expressed in CHO cells. Supernatant from the cell pellet was analyzed by SDS-PAGE and Western blot using anti-Fc antibody as a probe, demonstrating that both fEPOR201_ECD-Fc and fEPOR202_ECD-Fc can be recombinantly expressed (FIG. 7A). Extracellular domains of EPOR201 and EPOR202 comprising the amino acid sequence of SEQ ID NOs 29 and 30, respectively, may also be used.

Nucleotide sequences encoding full-length feline EPOR201 and EPOR202 with an N-terminal flag tag (SEQ ID NOs: 5 and 6, respectively) were synthesized and cloned in a mammalian expression vector. Each expression vector was transfected into CHO cells and a stable pool cells from each transfection was selected. Lysate from the cell pellet was analyzed by SDS-PAGE and Western blot using anti-flag antibody as a probe, demonstrating that both fEPOR201-N-flag and fEPOR202-N-flag can be recombinantly expressed (FIG. 7B and FIG. 7C). Feline full length EPOR expression cell line can be used for feline EPO binding assay or functional assay with or without proper modifications. Both EPOR201proteins (SEQ ID NOs: 5 and 7) were isolated using standard Protein A chromatography.

Example 9

Analog 6-30 GV Mature Binding to Feline EPO Receptor

The binding of Analog 6-30 GV Mature (SEQ ID NO: 12) to fEPOR201_ECD-Fc (SEQ ID NO: 7) and fEPOR202_ECD-Fc (SEQ ID NO: 8) was tested separately. The binding analysis was performed as follows. Briefly, fEPOR201_ECD-Fc and fEPOR202_ECD-Fc were biotinylated using EZ-Link NHS-LC-biotin (Catalog No. 21336, Thermo Scientific). The free unreacted biotin was removed by dialysis. Biotinylated fEPOR201_ECD-Fc and fEPOR202_ECD-Fc were captured on streptavidin sensor tips (Catalog No. 18-509, ForteBio).

The association of five different concentrations (150, 50, 17, 5.6, and 1.9 nM) of Analog 6-30 GV Mature was monitored for ninety seconds. Dissociation was monitored for 600 seconds. A buffer only blank curve was subtracted to correct for any drift. The data were fit to a 1:1 binding model using ForteBio™ data analysis software to determine the $k_{on}$ (association rate constant), $k_{off}$ (dissociation rate constant) and the $K_d$ (dissociation constant). The binding statistics fell within acceptable parameters (Chi-squared less than or equal to 3.0; R-squared greater than or equal to 0.9). The buffer for dilutions and all binding steps was: 200 mM phosphate, 150 mM NaCl, 0.02% Tween-20, 0.05% sodium azide, and 0.1 mg BSA, pH7.4. The $K_d$ of Analog 6-30 GV Mature and fEPOR201_ECD-Fc (SEQ ID NO: 7) was $4 \times 10^{-10}$ M and the $K_d$ of Analog 6-30 GV Mature and fEPOR202_ECD-Fc (SEQ ID NO: 8) was $1.7 \times 10^{-10}$ M.

Example 10

Comparison of Analog 6-30 GV Mature and Human EPO Binding to Human EPO Receptor

The binding of Analog 6-30 GV Mature and recombinant human EPO (Catalog No. E5627, Sigma-Aldrich) to human EPO receptor (EPOR) was compared. Briefly, extracellular domain of human EPOR (Catalog No. 963-ER-050, R&D Systems) was biotinylated. The free unreacted biotin was removed from biotinylated human EPOR by extensive dialysis. Biotinylated human EPOR was captured on streptavidin sensor tips. The association of five different concentrations (20, 6.7, 2.2, 0.74, and 0.25 nM) of either Analog 6-30 GV Mature or human EPO with human EPOR was monitored for ninety seconds. Dissociation was monitored for 600 seconds. A buffer only blank curve was subtracted to correct for any drift. The data were fit to a 1:1 binding model using ForteBio™ data analysis software to determine the $k_{on}$ (association rate constant), $k_{off}$ (dissociation rate constant), and the $K_d$ (dissociation constant). The binding statistics fell within acceptable parameters (Chi-squared less than or equal to 3.0; R-squared greater than or equal to 0.9). The buffer for dilutions and all binding steps was 200 mM phosphate, 150 mM NaCl, 0.02% Tween-20, 0.05% sodium azide, and 0.1 mg BSA, pH 7.4. The $K_d$ of human EPO and human EPOR was $1.07 \times 10^{-10}$ M and the $K_d$ of Analog 6-30 GV Mature and human EPOR was $9.76 \times 10^{-11}$ M. Analog 6-30 GV Mature and human EPO appear to have similar binding affinity to human EPOR.

Example 11

Comparison of Analog 6-30 GV Mature and Human EPO Proliferative Effect on TF-1 Cells EPO polypeptides have two EPO receptor binding sites. In vitro binding assays, like the assay described in Example 10, largely reflect first site binding kinetics since second site binding is understood to be weak (~500- to 1000-fold less affinity compared to first site) in humans. See Philo, J. S., et al., Dimerization of the extracellular domain of the erythropoietin (EPO) receptor by EPO: one high-affinity and one low-affinity interaction. Biochemistry 35, 1681-91 (1996). EPO-dependent cell proliferation assays, like the assay described in this example, can assess EPO activity as it relates to the integrity of the first binding site as well as the second binding site.

The proliferative effect of Analog 6-30 GV Mature on TF-1 cells expressing human EPOR was compared to that of recombinant human EPO (Catalog No E5627, Sigma-Aldrich). For the proliferation assay, TF-1 cells were cultivated in RPMI 1640 (Irvine Catalog No. 9160) supplemented with 10% (v/v) Fetal Bovine Serum, 2 mM L-glutamine, 100 units/mL Penicillin, 100 µg/mL Streptomycin, and 2 ng/mL rhGM-CSF (R&D Systems Catalog No. 215-GM). Before treatment with either Analog 6-30 GV Mature or recombinant human EPO, the TF-1 cells were seeded in a 96-flat well plate at $2 \times 10^5$ cells per mL and allowed to attach overnight. The next morning, the cells were treated with different concentrations of Analog 6-30 GV Mature or recombinant human EPO. Following incubation for 48 hours, MTT reagent was added to the cells for another 48-72 hours, according to the manufacturer's instructions. The insoluble purple reaction product was then dissolved with isopropanol, and the plate was read at 570 and 690 nm. The proliferation intensity was measured as a difference in optical density between 570 nm and 690 nm (40D) with the background corrected.

Figure 8:
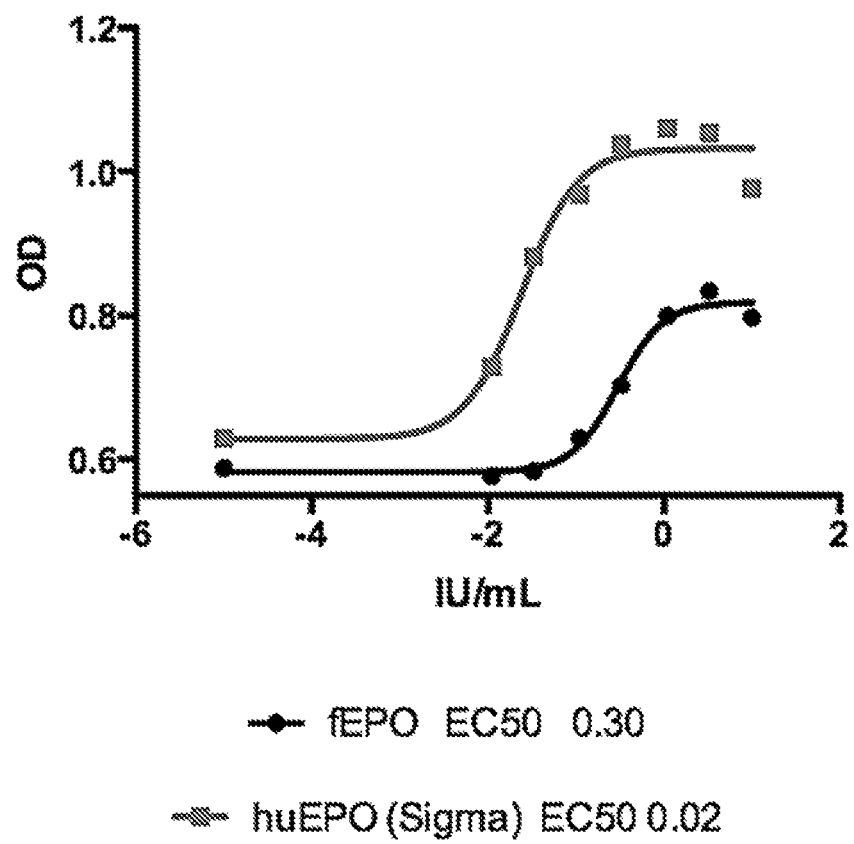
FIG. 8 shows results of a TF-1 cell proliferation assay of recombinant human EPO and Analog 6-30 GV Mature and calculated $EC_{50}$ values.

Proliferation response of TF-1 cells to Analog 6-30 GV Mature and recombinant human EPO is shown in FIG. 8. The concentration of EPO polypeptide that gives half-maximal response ($EC_{50}$) was determined for each proliferation curve. Unexpectedly, the similar affinity of Analog 6-30 GV Mature and recombinant human EPO to human EPOR (as measured in Example 10) did not appear to translate to a similar EC50 between the two EPO polypeptides based on this MTT assay. The EC50 for Analog 6-30 GV Mature (0.3 IU/mL) was an order of magnitude higher than the EC50 for recombinant human EPO (0.02 IU/mL), suggesting a lower proliferation activity for Analog 6-30 GV Mature compared to recombinant human EPO.

Example 12

Protein Structure Analysis of Feline EPO

To identify possible reasons for the decreased proliferative effect of Analog 6-30 GV Mature compared to recombinant human EPO, the structure of the second receptor binding site of wild-type feline EPO G18 and human EPO were compared.

First, the three-dimensional structure of feline EPO G18 and human EPO were obtained through protein structure modeling understood by persons in the art. Based on the location of the second binding site of human EPO, the second binding site of wild-type feline EPO G18 was identified. Next, the interface residues of the second receptor binding sites of wild-type feline EPO G18 and human EPO were compared and found unlikely to have affected second site binding of wild-type feline EPO G18. Then, amino acid residues at the interior of the second binding site of wild-type feline EPO G18 were considered. Unexpectedly, glycine (G) at position 18 was identified at the interior of the second binding site. In addition, empty volume in the protein structure was observed around G18.

Figure 9:
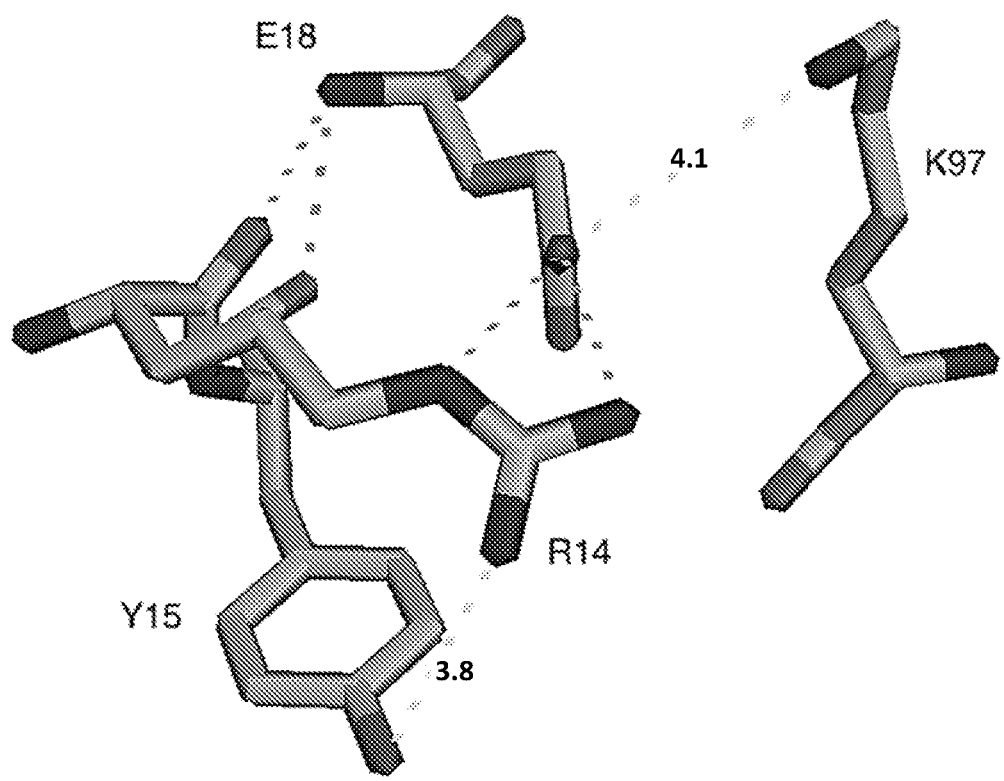
FIG. 9 shows proposed interactions between E18 and R14, Y15 and K97 of feline EPO.

This led to the investigation of the protein structure of wild-type feline EPO E18. Wild-type feline EPO E18 had been characterized as a variant and any difference in biological function (e.g., proliferative effect, etc.) between wild-type feline EPO G18 and EPO E18 was unclear. Based on this protein structure analysis, unlike G18, E18 appeared to form hydrogen bonds with R14 and hydrogen/Van der Waals forces with Y15. E18 appeared to also interact with K97. See FIG. 9. R14, Y15, and K97 are located at the interface of the second binding site and may be directly involved in maintaining second receptor binding.

In addition, the amino acid sequences of other mammalian species were considered and all of those considered were found to share not only E18, but also R14, Y15, and K97. All four amino acids (R14, Y15, E18 and K97) are conserved in human, dog, horse, Cynomolgus monkey, Rhesus monkey, mouse, rat, sheep, and pig.

Based on this analysis, G18 of Analog 6-30 GV Mature may have affected its second site binding and have attributed to its decreased proliferative effect.

Example 13

Expression and Isolation of Analog 6-30 EV

Upon discovering that E18 may be important for second site binding, studies involving analogs of wild-type feline EPO E18 were conducted. A nucleotide sequence encoding an EPO polypeptide having additional N-linked glycosylation sites compared to wild-type feline EPO E44 precursor form was chemically synthesized. Specifically, the sequence encoded "Analog 6-30 EV Precursor" (SEQ ID NO: 4), which has a glutamic acid at position 44, a valine substitution at position 113, and two additional N-linked glycosylation sites at positions 56-58 (N56T58) and 114-116 (N114) of wild-type feline EPO E44 precursor.

The nucleotide sequence was inserted into an expression vector and transfected into CHO DG-44 host cells. The CHO DG-44 cells were selected for high yield and stability of expression of the EPO polypeptide, using a DHFR gene on the expression vector and methotrexate-mediated gene amplification, as is known in the art. The mature form of the EPO polypeptide, named "Analog 6-30 EV Mature" (SEQ ID NO: 15) was secreted into the culture media. Analog 6-30 EV Mature was isolated according to the method described in Example 3.

Example 14

N-Linked Glycosylation Sites for Feline EPO E44

Wild-type feline EPO E44 precursor form (SEQ ID NO: 2 or "wild-type feline EPO E44") has three N-linked glycosylation sites at amino acid positions 50-52, 64-66, and 109-111, which correspond to amino acid positions 24-26, 38-40, and 83-85 of wild-type feline EPO E44 mature form (SEQ ID NO: 13 or "wild-type feline EPO E18").

Additional N-linked glycosylation sites may be also introduced into wild-type feline EPO E44 and wild-type feline EPO E18 amino acid sequences. For example, one, two, three, four, five, or six additional N-linked glycosylation sites may be introduced into wild-type feline EPO E44/E18 amino acid sequences. The N-linked glycosylation site may have a consensus sequence of Asn-Xaa-Ser/Thr, where Xaa is any amino acid except proline. Addition of one or more glycosylation sites may increase the molecular size of a feline EPO molecule, provide more sialylation sites, and/or improve the half-life of the molecule in an animal's serum.

Table 7 lists amino acid substitutions of wild-type feline EPO E44 and E18 that may be used to generate one or more additional N-linked glycosylation sites.

TABLE 7

| | Amino acid substitutions for N-linked glycosylation sites | |
|---|---|---|
| Analog No. | Based on wt feline EPO E44 sequence (SEQ ID NO: 2) | Based on wt feline EPO E18 sequence (SEQ ID NO: 13) |
| 1 | N47S49 | N21S23 |
| 2 | N47T49 | N21T23 |
| 3 | N55S57 | N29S31 |
| 4 | N55T57 | N29T31 |
| 5 | N56S58 | N30S32 |
| 6 | N56T58 | N30T32 |
| 7 | N60 | N34 |
| 8 | N60T62 | N34T36 |
| 9 | N61S63 | N35S37 |
| 10 | N61T63 | N35T37 |
| 11 | N79S81 | N53S55 |
| 12 | N79T81 | N53T55 |
| 13 | N82S84 | N56S58 |
| 14 | N82T84 | N56T58 |
| 15 | N91S93 | N65S67 |
| 16 | N91T93 | N65T67 |
| 17 | N92S94 | N66S68 |
| 18 | N92T94 | N66T68 |
| 19 | N97S99 | N71S73 |
| 20 | N97T99 | N71T73 |
| 21 | N98S100 | N72S74 |
| 22 | N98T100 | N72T74 |
| 23 | N99S101 | N73S75 |
| 24 | N99T101 | N73T75 |
| 25 | N112*X113 | N86*X87 |
| 26 | N112*X113T114 | N86*X87T88 |
| 27 | N113S115 | N87S89 |
| 28 | N113T115 | N87T89 |
| 29 | N114S116 | N88S90 |
| 30 | N114 | N88 |
| 31 | N115S117 | N89S91 |
| 32 | N115T117 | N89T91 |
| 33 | N116S118 | N90S92 |
| 34 | N116T118 | N90T92 |
| 35 | N137S139 | N111S113 |
| 36 | N137T139 | N111T113 |
| 37 | N140S142 | N114S116 |
| 38 | N140T142 | N114T116 |
| 39 | N141S143 | N115S117 |
| 40 | N141T143 | N115T117 |
| 41 | N142S144 | N116S118 |
| 42 | N142T144 | N116T118 |
| 43 | N143S145 | N117S119 |
| 44 | N143 | N117 |
| 45 | N144 | N118 |
| 46 | N144T146 | N118T120 |
| 47 | N145S147 | N119S121 |
| 48 | N145T147 | N119T121 |
| 49 | N146S148 | N120S122 |
| 50 | N146T148 | N120T122 |
| 51 | N147*X148S149 | N121*X122S123 |
| 52 | N147*X148T149 | N121*X122T123 |
| 53 | N148S150 | N122S124 |
| 54 | N148T150 | N122T124 |
| 55 | N149S151 | N123S125 |
| 56 | N149 | N123 |
| 57 | N150 | N124 |
| 58 | N150T152 | N124T126 |
| 59 | N161S163 | N135S137 |
| 60 | N161 | N135 |
| 61 | N162S164 | N136S138 |
| 62 | N162T164 | N136T138 |
| 63 | N184S186 | N158S160 |
| 64 | N184T186 | N158T160 |
| 65 | N186S188 | N162S164 |
| 66 | N186T188 | N162T164 |

*X indicates any amino acid except proline.

Example 15

Analog 6-30 EV Mature and Analog 6-30 GV Mature Binding to EPOR

Binding of an acidic (high sialylation) fraction of Analog 6-30 EV Mature (SEQ ID NO: 15), an acidic (high sialylation) fraction of Analog 6-30 GV Mature (SEQ ID NO:14) having an isoelectric point range of about 2 to about 3.5, and a basic (low sialylation) fraction of Analog 6-30 GV Mature having an isoelectric point range of about 4 to about 5 to human EPOR-Fc (Catalog No. 963-ER-050, R&D Systems) was tested by ELISA.

A 96-well plate was coated with a mouse anti-EPO specific antibody (Catalog No. MAB287, clone 9C21D11, R&D Systems) to capture the EPO polypeptides. The EPO-bound wells were incubated with human EPOR-Fc at a concentration of 200 ng/mL and the bound EPOR was detected by anti-human Fc HRP conjugated antibody. The ELISA was performed a second time, but the three samples of EPO polypeptides were first treated with neuraminidase to remove the sialic acid. The resulting EC50s are listed in Table 8, below.

TABLE 8

| Feline EPO analog | EC50 | |
| --- | --- | --- |
| | ELISA 1 | ELISA 2* |
| Analog 6-30 EV Mature (acidic fraction) | 45 ng/mL | 20 ng/mL |
| Analog 6-30 GV Mature (acidic fraction) | 100 ng/mL | 18 ng/mL |
| Analog 6-30 GV Mature (basic fraction) | 35 ng/mL | 31 ng/mL |

*EPO samples were neuraminidase-treated prior to performing ELISA 2.

The acidic (high sialylation) fraction of Analog 6-30 GV Mature exhibited a higher EC50 value compared to the basic (low sialylation) fraction, suggesting reduced receptor binding affinity with the acidic fraction. This result was consistent with the binding assay results of Example 6 comparing an acidic and basic fraction of Analog 6-30 GV Mature. When sialic acid residues were removed for the second ELISA, the EC50 values for Analog 6-30 EV Mature and Analog 6-30 GV Mature were generally similar, suggesting similar binding affinities for EPO receptor.

Example 16

Proliferative Effect of Analog 6-30 EV Mature and Analog 6-30 GV Mature

The integrity of first and second receptor binding sites of Analog 6-30 EV Mature (SEQ ID NO: 15) and Analog 6-30 GV Mature (SEQ ID NO: 14) were compared by a TF-1 cell proliferation assay as described in Example 11. In this assay, two samples were tested: 1) Analog 6-30 EV Mature and 2) a mixture of 50% Analog 6-30 EV Mature and 50% Analog 6-30 GV Mature.

Figure 10:
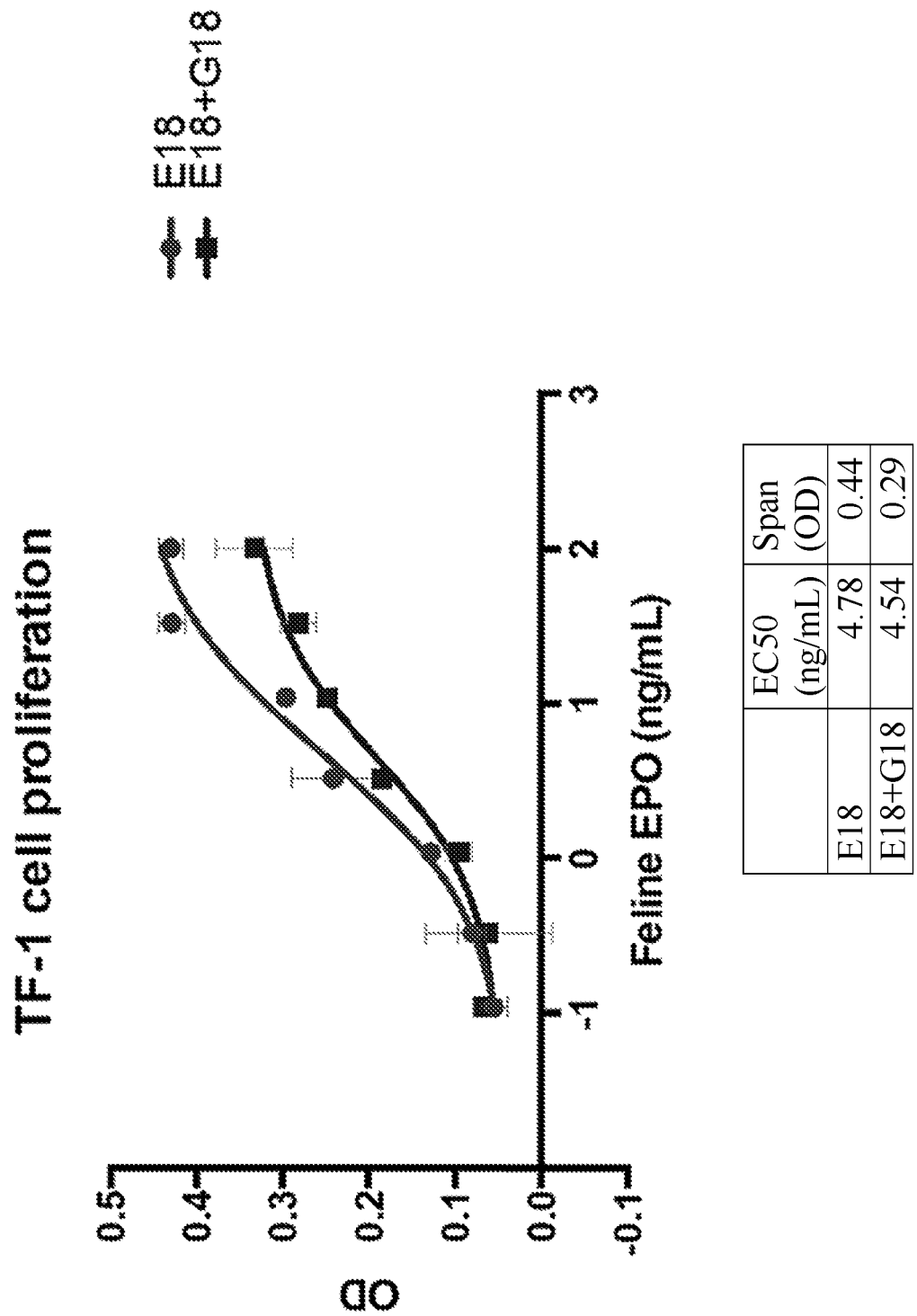
FIG. 10 shows results of a TF-1 cell proliferation assay of Analog 6-30 EV Mature and a 50/50 mixture of Analog 6-30 EV Mature and Analog 6-30 GV Mature.

TF-1 cells were treated with different concentrations of samples 1 and 2 and MTT reagent was used to measure proliferation. The reaction product was dissolved with isopropanol and the plate read at 570 and 690 nm. The proliferation intensity was measured as a difference in optical density between 570 nm and 690 nm (ΔOD) with the background corrected. Proliferation response of TF-1 cells to Samples 1 and 2 are shown in FIG. 10.

The concentration of EPO polypeptide that gives half-maximal response (EC5o) was determined for each proliferation curve. The EC50s for Sample 1 (4.78 ng/mL) and Sample 2 (4.54 ng/mL) were similar, suggesting that it is likely that the presence of 50% Analog 6-30 GV Mature in Sample 2 did not affect the EC50. However, Analog 6-30 GV Mature appeared to reduce the span or proliferation signal of Sample 2 (ΔOD=0.29) when compared to Sample 1 (ΔOD=0.44). The reduction in proliferation activity between the two samples suggests that G18 attenuates second site binding activity.

Example 17

EPO Second Site Mutants

EPO having a defect in the second binding site (or a "site 2 defect") may be used to antagonize endogenous EPO activity. For example, EPO with a defect in second site binding may compete for EPO receptor binding and block signaling, thus prevent new red blood cell generation. Thus, EPO with second site mutation(s) may be agent to treat disease such as certain forms of polycythemia (elevated red blood cell counts) due to excess EPO production, such as a condition caused by tumors (e.g., kidney tumors) that secrete excess EPO or inherited disorders of overproduction of EPO.

In cases where the endogenous EPO receptor is hypersensitive, or self-activating, administration of EPO having a defect in the second binding site may block the mutant receptor. At high dose, EPO having a site 2 defect may kill the target cells, when needed, to form excessive 1:1 ratio of EPO:receptor complex and/or reduce red blood cell formation.

One or more second site mutations of human EPO, feline EPO, or canine EPO are selected from an amino acid substitution at a position corresponding to position L(5), D(8), R(10), V(11), R(14), Y(15), Q(78), D(96), K(97), V(99), S(100), R(103), S(104), T/S (107), L(108), or R(110) of a wild-type feline EPO polypeptide. For example, R(103) can be mutated to Ala or other amino acid to disrupt second site activity.

Example 18

Sialic Acid Characterization of Analog 6-30 EV Mature

The sialic acid content of an acidic fraction of Analog 6-30 EV Mature (SEQ ID NO: 15) was analyzed and compared to that of an acidic fraction of Analog 6-30 GV Mature (SEQ ID NO: 14), which had approximately 20 sialic acid molecules per polypeptide. The IEF profiles of Analog 6-30 EV Mature and Analog 6-30 GV Mature were similar suggesting that the E analog had a similar sialic acid content to the G analog. N-acetylneuraminic acid was identified as the predominant form of sialic acid present on both analogs.

Sialic acid analysis was performed as follows. Sialic acid was released from Analog 6-30 EV Mature (SEQ ID NO: 15) by mixing 30 µL of sample with 4 µL of glacial acetic acid. The mixture was incubated at 80° C. for 2 hours. Free sialic acid was labeled with fluorescence dye 1,2-diamino-4,5-methylenoxybenzene (DMB). The florescence labelling was performed by mixing 20 µL of the DMB-thionite solution with 5 µL of the free sialic acid samples. The mixture was incubated at 50° C. for 3 hours. The reaction was stopped by adding 75 µL of distilled, deionized water. The DMB labeled sialic acid was analyzed by HPLC using either a Zorbax SB-C18 column (5µ, 4.6×150 mm) or Extend C18 column (5µ, 4.6×150 mm) (Agilent Technologies), with isocratic mobile phase containing 7% methanol, 9% acetonitrile, and 84% water. All the neuraminic acids, e.g., Neu5Gc (NGNA); Neu5Ac (NANA); Neu5,7Ac2; Neu5,Gc9Ac; Neu5,9Ac2; and Neu5,7(8),9Ac are base line resolved in 30 minutes.

Example 19

Feline EPO E18 Binding to Feline EPOR

A predicted protein sequence for an alternatively-spliced variant of feline EPOR (fEPOR203 (SEQ ID NO: 27)) was obtained from the NCBI database as Accession No. XP_0196733781 The amino acid at position 39 was not known and is represented in the database by an "X." Three-dimensional protein structural modeling was performed and placement of alanine at position 39 of EPOR203 (SEQ ID NO: 21) was determined to maintain the right N-terminal protein conformation.

A soluble, extracellular domain of EPOR203 was identified (EPOR203_39A ECD; SEQ ID NO: 26) and the nucleotide sequence encoding a signal sequence, EPOR203_39A ECD, a linker, and human Fc (EPOR203_39A_ECD_Fc; SEQ ID NO: 22) was synthesized, cloned into a mammalian expression vector, and expressed in HEK or CHO cells. EPOR203_39A_ECD_Fc was purified from the cell culture supernatant by Protein A affinity column chromatography and formulated in PBS at neutral pH. FIG. 7D shows a Coomassie stain of SDS-PAGE analysis of feline EPOR203-ECD-Fc. An extracellular domain of EPOR203 comprising the amino acid sequence of SEQ ID NO: 31 may also be used.

Example 20

Analog 6-30 EV Mature Binding to Feline EPO Receptor

Figure 11:
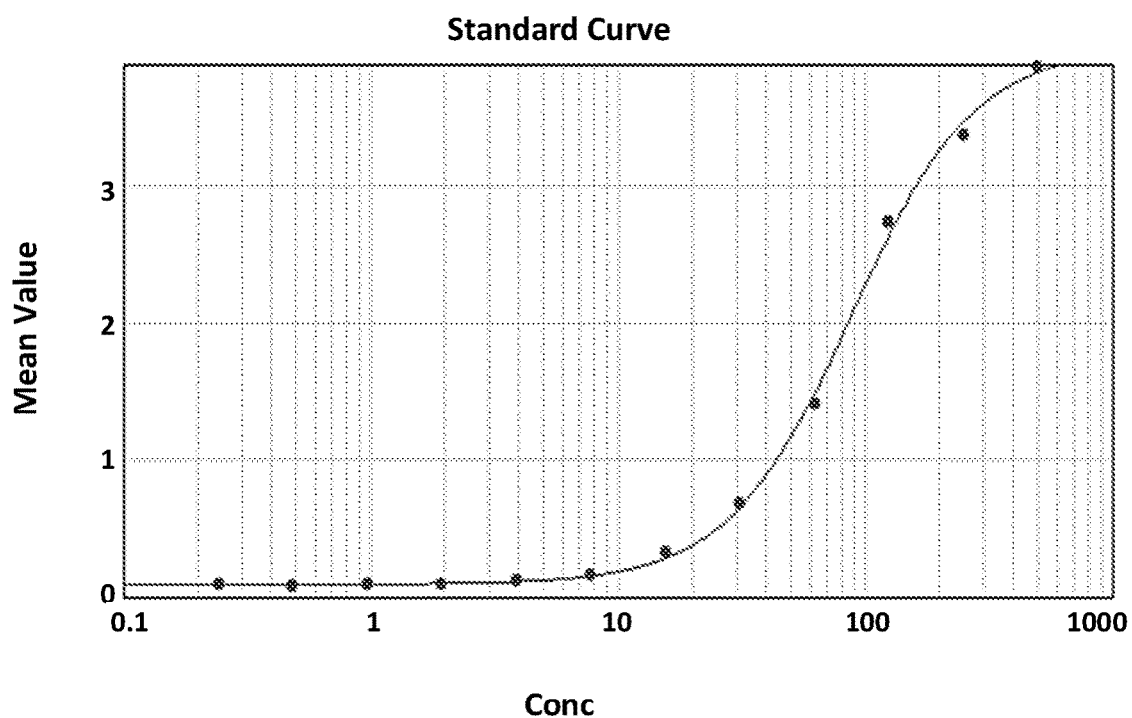
FIG. 11 shows an ELISA binding assay between Feline Analog 6-30 EV Mature (SEQ ID NO: 15) and Feline EPOR203_39A_ECD_Fc (SEQ ID NO: 26). The four parameters represented are A: minimum value; D: maximum value; C: point of inflection; and D: Hill's slope of the curve.

The binding of Analog 6-30 EV Mature (SEQ ID NO: 15) to feline EPOR203_39A_ECD_Fc (SEQ ID NO: 26) was assessed using an ELISA-based assay in duplicate. A MaxiSorp 96-well plate was coated overnight with anti-human EPO antibody (4 µg/mL) at refrigeration temperature (2-8° C.) and blocked with 5% BSA in PBS for 1 hour at room temperature. Analog 6-30 EV Mature was prepared in 2-fold serial dilutions starting with a concentration of 500 ng/mL in 1% BSA-PBST (0.05% Tween-20) buffer. Dilutions of Analog 6-30 EV Mature (100 µL) were transferred to each well and incubated at room temperature for 2 hours. Feline EPOR203_39A_ECD_Fc (200 ng/mL in 1% BSA-PBST buffer) was added to each well and binding allowed to proceed for 1 hour at room temperature. A rabbit anti-human Fc antibody and horseradish peroxidase (HRP) conjugate (0.2 µg/mL) was used for detection and left in the wells for 1 hour at room temperature. 3,3,5,5'-Tetramethylbenzidine (TMB) was applied to the wells as the HRP substrate and kept in the well for 5 to 7 minutes for signal development. Binding between Analog 6-30 EV Mature (SEQ ID NO: 15) and feline EPOR203_39A_ECD_Fc was demonstrated. The mean detection signal was plotted against Analog 6-30 EV Mature concentration and curve fit analysis performed (FIG. 11).

Example 21

Administration of Analog 6-30 EV Mature to Normal Cats

A single dose of Analog 6-30 EV Mature (SEQ ID NO: 15) at 1 µg/kg (n=5), 3 µg/kg (n=5), or 10 µg/kg (n=5), Analog 6-30 GV Mature (SEQ ID NO: 14) at 10 µg/kg (n=4), or PBS was administered subcutaneously to normal cats. Absolute reticulocyte percentages were measured as an indicator of EPO bioactivity. In brief, EPO binds to EPO receptor on erythroid cells and the dimerization of the receptor activates the JAK2 pathway and signaling of erythropoiesis. Erythroid cells differentiate into reticulocytes, then red blood cells. Thus, an increase in EPO bioactivity and erythropoiesis is evidenced by an increase in the percentage of absolute reticulocytes.

Figure 12:
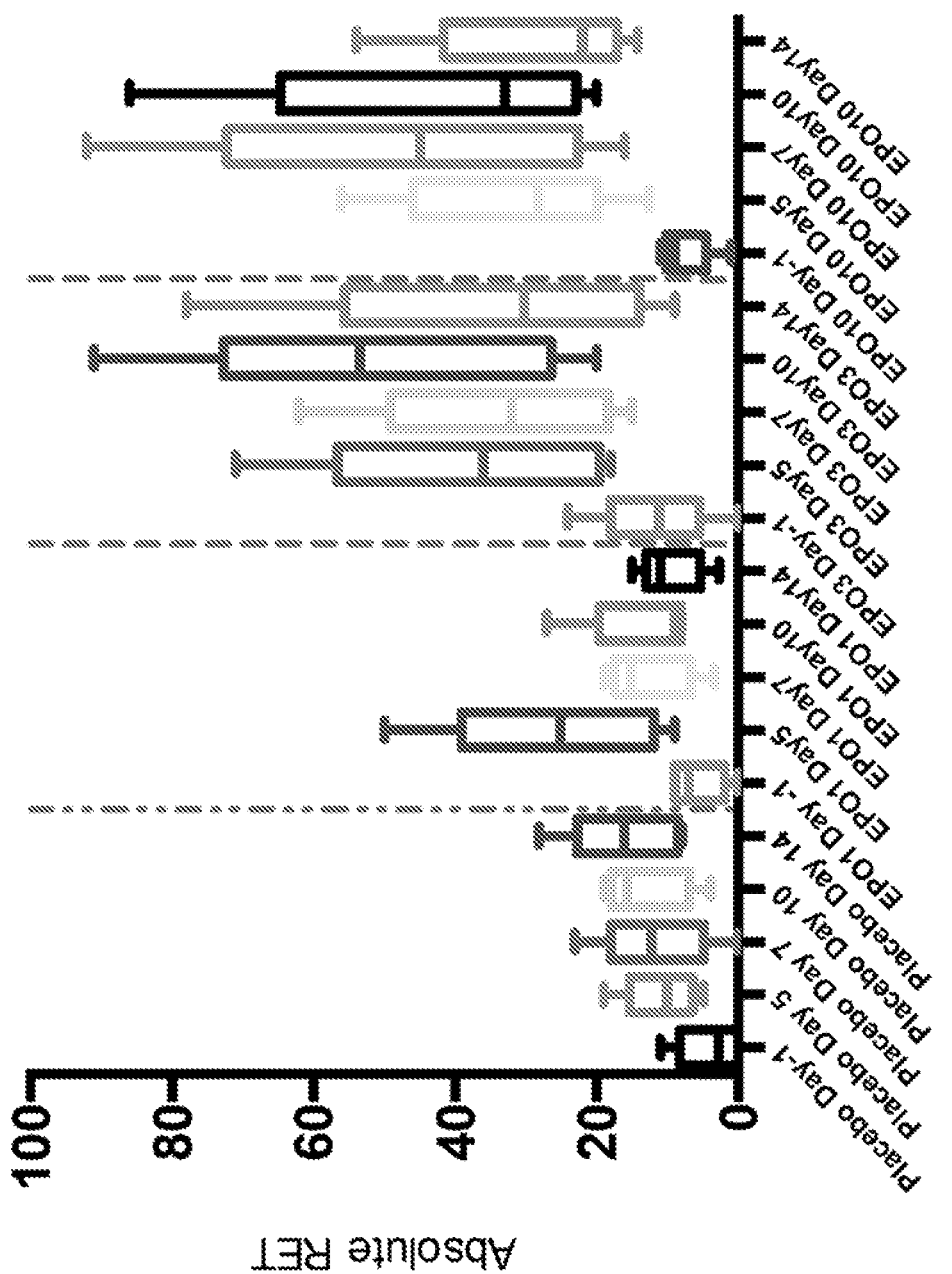
FIG. 12 is a graph showing the absolute reticulocyte percentage in cats at 1 day prior to and at 5, 7, 10, and 14 days after administration of placebo or Feline Analog 6-30 EV Mature (SEQ ID NO: 15) at one of three dose levels (1 µg/kg ("EPO1;" n=5), 3 µg/kg ("EPO3;" n=5), or 10 µg/kg ("EPO10;" n=5)).
Figure 13:
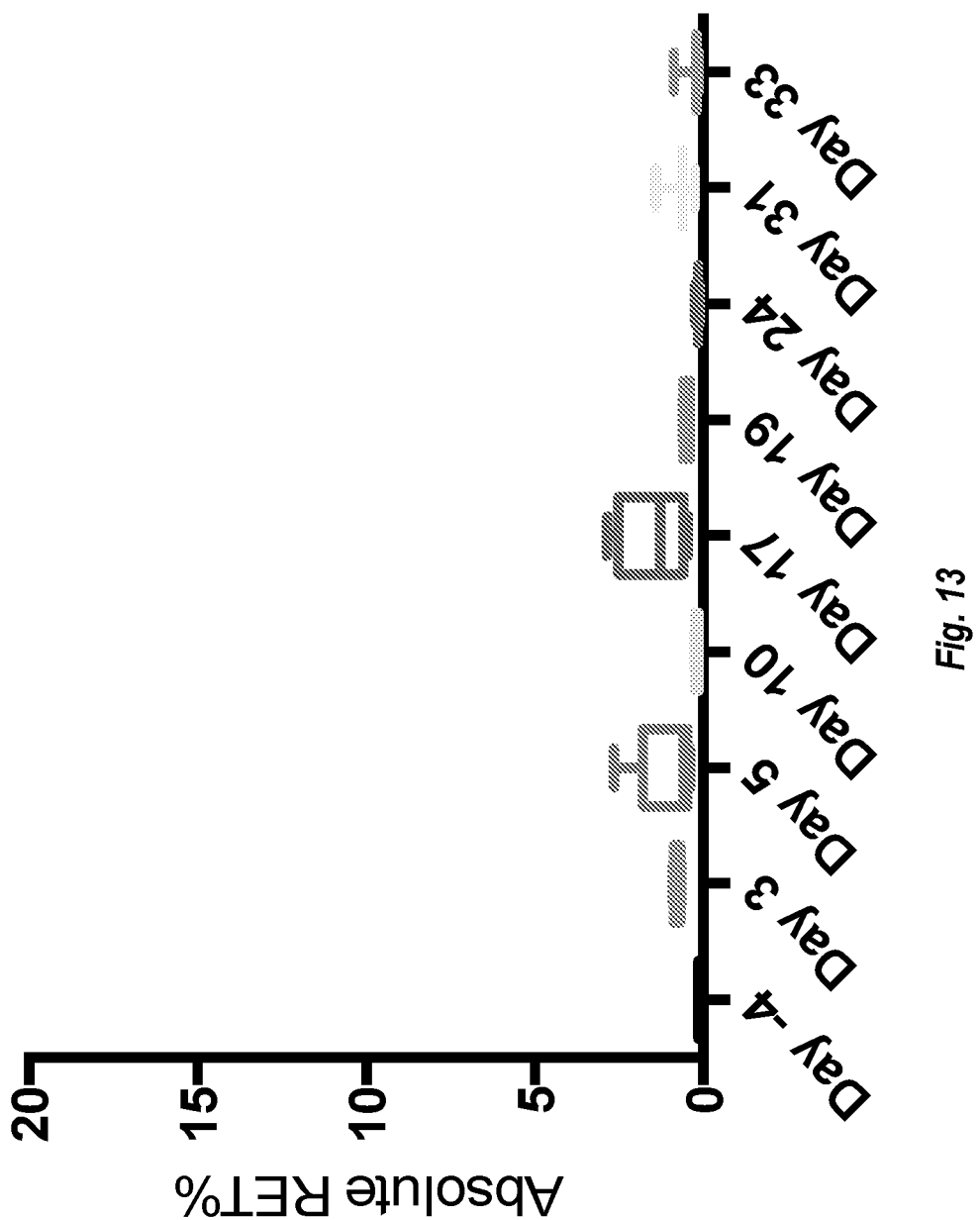
FIG. 13 is a graph showing the absolute reticulocyte percentage in cats at 4 days prior to and at 3, 5, 10, 17, 19, 24, 31, and 33 days after administration of Feline Analog 6-30 GV Mature (SEQ ID NO: 14; 10 µg/kg; n=4).

FIG. 12 shows the mean absolute reticulocyte percentage in cats at 1 day before dosing and at day 5, 7, 10, and 14 after subcutaneous administration of placebo or Analog 6-30 EV Mature or PBS (n=4). FIG. 13 shows the mean absolute reticulocyte percentage in cats at 4 days before dosing and at day 3, 5, 10, 17 19, 24, 31, and 33 after subcutaneous administration of Analog 6-30 GV. An increase in erythropoiesis was demonstrated in the groups treated with Analog 6-30 EV Mature, but not in the group treated with Analog 6-30 GV Mature.

Example 22

Efficacy Study of Analog 6-30 EV Mature in Anemic Cats

An open-label, historical controlled (compared cats' post-treatment and pre-treatment data), pilot efficacy study was conducted to evaluate the effectiveness of Analog 6-30 EV Mature (SEQ ID NO: 15) on red blood cells (RBC), reticulocytes, and Quality of Life (QoL) in client-owned cats with International Renal Interest Society (IRIS) Stage 3 Chronic Kidney Disease (CKD) and anemia. Safety was also evaluated by the collation of any adverse events (AE) and the presence of neutralizing antibodies. Preliminary data from two cats that completed the study showed an improvement of anemia (i.e., increased hematocrit percentage (HCT %)), suggested an improvement in the symmetric dimethylarginine (SDMA) and serum creatinine renal biomarker tests specific to kidney function, and showed maintenance or improvement in body weight.

Cats with IRIS Stage 3 CKD and anemia that met all the following eligibility criteria were enrolled:

Inclusion Criteria

The cat:
1. Is manageable and cooperative with study procedures
2. Has rapidly progressive CKD with a 25% increase in fasting serum creatinine between two consecutive evaluations
3. Is at least 1 year of age on Day 0 and is: any gender; intact or neutered; non-pregnant, non-lactating; any breed and any weight
4. Has IRIS Stage 3 CKD, defined as:
   a) A Screening Visit fasting serum creatinine of 2.9-5.0 mg/dL and a previous medical history of serum creatinine of 2.9-5.0 mg/dL within 6 months of Day 0 (fasting or unfasted); and
   b) Urine specific gravity (USG)<1.035
5. Has non-regenerative anemia and a 15-30% HCT
6. Is receiving standard of care therapy for CKD Exclusion Criteria The cat:
1. Resides mostly outdoors (>60% of each day is spent outside)
2. Has rapidly progressive CKD with a 25% increase in fasting serum creatinine between two consecutive evaluations
3. Has ever been treated with an erythropoietin stimulating agent 4. Has been administered whole or packed red blood cells within 6 weeks of Day 0;
5. Has a urinary tract infection (UTI) with the following exception: cats with a UTI may be enrolled post-treatment with the appropriate antibiotic therapy (based on culture/sensitivity) for 3 weeks and repeat negative culture
6. Has any of the following diseases/conditions:
   Neoplasia
   Liver disease
   Feline leukemia virus (FeLV)
   Feline immunodeficiency virus (FIV)
   Diabetes mellitus (DM)
   Hyperthyroidism
   Hematocrit <15%
   Systemic blood pressure >160 mmHg
7. Requires a new prescription or a prescription change (dose or dose frequency) to an existing concurrent medication or therapy for CKD two weeks before Day 0.

Two cats were administered Analog 6-30 EV Mature (SEQ ID NO: 15) subcutaneously twice at a starting dose of 3 µg/kg approximately 7-10 days apart, and followed for six weeks. Cats were concurrently administrated iron dextran.

The following data was collected and/or evaluated at all visits (scheduled or unscheduled): physical examination with a medical history, quality of life (vitality, comfort, and emotional wellbeing), appetite, activity (Vetrax activity sensor affixed to a neck collar), blood pressure, and owner diary of observed events. At initial Screening and Week 6 Visits, hematology, biochemistry, urinalysis with urine protein to creatinine ratio, and SDMA assessments were made. Urine culture±sensitivity was assessed at baseline and as needed throughout the study. Hematocrit was assessed in-house at all scheduled and unscheduled visits.

The baseline hematocrit improved from a baseline of 22.8% to a maximum of 35.9% (at Week 4) in Cat WEX-201 (Table 9) and from a baseline 26.6% to a maximum of 35.5% (at Week 2) in Cat LUN-201 (Table 10). Since the anemia (HCT) improved in both cats following the second dose of Analog 6-30 EV Mature, additional doses were not administered during the study; however, the decline in HCT by Week 6 in WEX-201 and Week 5 in LUN-201 suggests further treatment may be administered to maintain the HCT.

The SDMA renal biomarker test improved (i.e., reduced) from 30 to 14 µg/dL in Cat WEX-201 (Table 9) and from 29 to 17 µg/dL in Cat LUN-201 (Table 10). The body weight was either maintained (LUN-201; Table 10) or improved (WEX-201; Table 9) during the study.

TABLE 9

WEX-201 Data

| VISIT | Hematocrit (%) | Dose (3 µg/kg) administered | BW (kg) | SDMA (ug/dL) | Serum creatinine (mg/dL) |
|---|---|---|---|---|---|
| Screening | 22.8 | N/A | 3.9 | 30 | 3.4 |
| Day 0 | 27.9 | Yes | 4 | N/A | N/A |
| Unscheduled | 26 | No | 3.8 | N/A | N/A |
| Week 1 | 23.5 | Yes | 4 | N/A | N/A |
| Week 2 | 31.2 | No | 4.5 | N/A | N/A |
| Week 3 | 35 | No | 4.3 | N/A | N/A |
| Week 4 | 35.9 | No | 4.3 | N/A | N/A |
| Week 5 | 35 | No | 4.3 | N/A | N/A |
| Week 6 | 17 | N/A | 4.5 | 14 | 1.3 |

TABLE 10

LUN-201 Data

| VISIT | Hematocrit (%) | Dose (3 µg/kg) administered | BW (kg) | SDMA (ug/dL) | Serum creatinine (mg/dL) |
|---|---|---|---|---|---|
| Screening | 26.6 | N/A | 3.1 | 29 | 3.3 |
| Day 0 | 25.9 | Yes | 3.1 | N/A | N/A |
| Week 1 | 30.8 | Yes | 3.1 | N/A | N/A |
| Week 2 | 35.5 | No | 3.0 | N/A | N/A |
| Week 3 | 33.0 | No | 3.2 | N/A | N/A |
| Week 4 | 32.7 | No | 3.1 | N/A | N/A |
| Week 5 | 30.6 | No | 3.1 | N/A | N/A |
| Week 6 | 29.6 | N/A | 3.1 | 17 | 2.0 |

The trend for improved SDMA and serum creatinine renal biomarkers observed in the cats suggests improved renal function post-treatment with Analog 6-30 EV Mature. It is not uncommon for cats with late stage CKD and anemia to experience clinically relevant comorbidities that result in undesired weight loss. Treatment with Analog 6-30 EV Mature was effective to either increase (WEX-201) or maintain (LUN-201) body weight.

The invention claimed is:

1. An erythropoietin (EPO) polypeptide comprising the amino acid sequence of SEQ ID NO: 13 except for the presence of at least one N-linked glycosylation site not present in SEQ ID NO: 13, wherein the N-linked glycosylation site consists of the sequence asparagine-xaa-serine or asparagine-xaa-threonine, wherein xaa is any amino acid except proline, and wherein one N-linked glycosylation site does not overlap with another N-linked glycosylation site, and wherein each of the at least one N-linked glycosylation site is present at a position selected from the group consisting of positions 21-23, 29-31, 34-36, 35-37, 53-55, 56-58, 65-67, 66-68, 71-73, 72-74, 73-75, 86-88, 87-89, 111-113, 114-116, 115-117, 116-118, 117-119, 118-120, 119-121, 120-122, 121-123, 122-124, 123-125, 135-137, 136-138, 158-160, and 162-164 of SEQ ID NO: 13.

2. The EPO polypeptide of claim 1, wherein the EPO polypeptide is glycosylated.

3. The EPO polypeptide of claim 1, wherein the EPO polypeptide is PEGylated.

4. The EPO polypeptide of claim 1 comprising a valine at the position corresponding to position 87 of SEQ ID NO: 13.

5. The EPO polypeptide of claim 4, wherein the EPO polypeptide is glycosylated.

6. The EPO polypeptide of claim 4, wherein the EPO polypeptide is PEGylated.

7. A pharmaceutical composition comprising the EPO polypeptide of claim 1 and a pharmaceutically acceptable carrier.

8. A method of delivering an EPO polypeptide to a companion animal species comprising administering the EPO polypeptide of claim 1 parenterally.

9. A method of treating a companion animal species having anemia comprising administering to the companion animal species a therapeutically effective amount of the EPO polypeptide of claim 1.

10. The method of claim 9, wherein the companion animal species has a baseline hematocrit percentage of from about 15% to about 30% prior to the administration of the EPO polypeptide.

* * * * *